(12) United States Patent
Strand

(10) Patent No.: US 9,422,575 B2
(45) Date of Patent: Aug. 23, 2016

(54) POLYDNAVIRUS DELIVERY CONSTRUCTS

(75) Inventor: Michael Strand, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 145 days.

(21) Appl. No.: 14/241,135

(22) PCT Filed: Aug. 27, 2012

(86) PCT No.: PCT/US2012/052476
§ 371 (c)(1),
(2), (4) Date: May 7, 2014

(87) PCT Pub. No.: WO2013/032999
PCT Pub. Date: Mar. 7, 2013

(65) Prior Publication Data
US 2014/0302609 A1    Oct. 9, 2014

Related U.S. Application Data

(60) Provisional application No. 61/527,899, filed on Aug. 26, 2011.

(51) Int. Cl.
| | |
|---|---|
| *C12N 15/85* | (2006.01) |
| *C12N 15/86* | (2006.01) |
| *C07K 14/005* | (2006.01) |

(52) U.S. Cl.
CPC ............. *C12N 15/86* (2013.01); *C07K 14/005* (2013.01); *C12N 2710/00011* (2013.01); *C12N 2710/00043* (2013.01)

(58) Field of Classification Search
None
See application file for complete search history.

(56) References Cited

U.S. PATENT DOCUMENTS 5,965,399 A * 10/1999 Chatterjee .......... C07K 14/4703
435/194
6,143,565 A   11/2000 Dougherty et al.

OTHER PUBLICATIONS

Annaheim M., Lanzrein B. 2007. Genome organization of the Chelonus inanitus polydnavirus: excision sites, spacers, and abundance of proviral and excised segments. J. Gen. Virol. 8: 450-457.
Beck M., Strand M. R. 2003. RNA interference silences Microplitis demolitor bracovirus genes and implicates glc1.8 in disruption of adhesion in infected host cells. Virology 314: 521-535.
Beck M. H., Strand M. R. 2005. Glc1.8 from Microplitis demolitor bracovirus induces a loss of adhesion and phagocytosis in insect high five and S2 cells. J. Virol. 79: 1861-1870.
Beck M. H., Strand M. R. 2007. A novel polydnavirus protein inhibits the insect prophenoloxidase activation pathway. Proc. Natl. Acad. Sci. U. S. A. 104: 19267-19272.
Beck M. H., Inman R. B., Strand M. R. 2007. Microplitis demolitor bracovirus genome segments vary in abundance and are individually packaged in virions. Virology 359: 179-189.
Beck M. H., et al. The encapsidated genome of Microplitis demolitor bracovirus integrates into the host Pseudoplusia includens. J Virol. 2011 85(22):11685-96.
Bezier A., et al. 2009. Polydnaviruses of braconid wasps derive from an ancestral nudivirus. Science 323: 926-930.
Bitra K., Zhang S., Strand M. R. 2011. Transcriptomic profiling of Microplitis demolitor bracovirus reveals host, tissue, and stage-specific patterns of activity. J. Gen. Virol. 92: 2060-2071.
Bossin H., et al. 2003. Junonia coenia densovirus-based vectors for stable transgene expression in Sf9 cells: influence of the densovirus sequences on genomic integration. J. Virol. 77: 11060-11071.
Burke G. R., Strand M. R. 2012. Deep sequencing identifies viral and wasp genes with potential roles in replication of microplitis demolitor bracovirus. J. Virol. 86(6): 3293-3306.
Daya S., Cortez N., Berns K. I. 2009. Adeno-associated virus site-specific integration is mediated by proteins of the nonhomologous end-joining pathway. J. Virol. 83: 11655-11664.
Desjardins C. A., et al. 2008. Comparative genomics of mutualistic viruses of Glyptapanteles parasitic wasps. Genome Biol. 9: R183.
Doucet D., et al. 2007. In vitro integration of an ichnovirus genome segment into the genomic DNA of lepidopteran cells. J. Gen. Virol. 88: 105-113.
Dupuy C., Huguet E., Drezen J.-M. 2006. Unfolding the evolutionary history of polydnaviruses. Virus Res. 117: 81-89.
Fleming JG. 1992. Polydnaviruses: mutualists and pathogens. Annu. Rev. Entomol. 37: 401-425.
Fleming JG, Summers MD. Polydnavirus DNA is integrated in the DNA of its parasitoid wasp host. roc Natl Acad Sci U S A. 1991 88(21):9770-4.
Gunderson-Rindal D., Dougherty E. M. 2000. Evidence for integration of Glyptapanteles indiensis polydnavirus DNA into the chromosome of Lymantria dispar in vitro. Virus Res. 66: 27-37.
Gunderson-Rindal D. E., Lynn D. E. 2003. Polydnavirus integration in lepidopteran cells in vitro. J. Insect Physiol. 49: 453-462.
Gunderson-Rindal D., et al. Transformation of lepidopteran and coleopteran insect cell lines by Glyptapanteles indiensis polydnavirus DNA. In Vitro Cell Dev Biol Anim. 1999 35(2):111-4.
Johnson J. A., et al. 2010. The UGA-CiE1 cell line from Chrysodeixis includens exhibits characteristics of granulocytes and is permissive to infection by two viruses. Insect Biochem. Mol. Biol. 40: 394-404.
Kim M. K., Sisson G., Stoltz D. 1996. Ichnovirus infection of an established gypsy moth cell line. J. Gen. Virol. 77: 2321-2328.

(Continued)

*Primary Examiner* — Michelle S Horning
(74) *Attorney, Agent, or Firm* — Meunier Carlin & Curfman LLC

(57) ABSTRACT

Provided herein are methods of producing a genetically modified cell by introducing a polydnavirus delivery construct to a target cell. The polydnavirus delivery construct can comprise an exogenous nucleic acid to form a genetically modified cell comprising the exogenous nucleic acid. Also provided are polydnavirus delivery constructs comprising an exogenous nucleic acid, as well as polydnavirus virions and genetically modified cells comprising the same. Further provided are in vitro methods of identifying a transformed cell. The methods comprise introducing a vector comprising a nucleotide sequence encoding a glc polypeptide to an adherent cell and cultivating the cell under conditions that allow for the expression of the glc polypeptide. Expression of the glc polypeptide results in a transformed cell that is identified by a loss of adherency.

15 Claims, 23 Drawing Sheets

(56) References Cited

OTHER PUBLICATIONS

Kotin R. M., Linden R. M., Berns K. I. 1992. Characterization of a preferred site on human chromosome 19q for integration of adeno-associated virus DNA by non-homologous recombination. EMBO J. 11: 5071-5078.

Linden M. R., Ward P., Giraud C. C., Winocour E., Berns K. I. 1996. Site-specific integration by adeno-associated virus. Proc. Natl. Acad. Sci. U. S. A. 93: 11288-11294.

Lu Z., Beck M. H., Jiang H., Wang Y., Strand M. R. 2008. The viral protein Egf1.0 is a dual activity inhibitor of prophenoloxidase activating proteinases 1 and 3 from Manduca sexta. J. Biol. Chem. 283: 21325-21333.

McKelvey T. A., et al. 1996. Transformation of gypsy moth cell lines by infection with Glyptapanteles indiensis polydnavirus. Biochem. Biophys. Res. Commun. 224: 764-770.

Ochman H., Ayala F. J., Hartl D. L. 1993. Use of polymerase chain reaction to amplify segments outside boundaries of known sequences. Methods Enzymol. 218: 309-321.

Pennachio F., Strand M. R. 2006. Evolution of developmental strategies in parasitic Hymenoptera. Annu. Rev. Entomol. 51: 233-258.

Philpott N. J., et al. 2002. Efficient integration of recombinant adeno-associated virus DNA vectors requires a p5-rep sequence in cis. J. Virol. 76: 5411-5421.

Pruijssers A. J., Strand M. R. 2007. PTP-H2 and PTP-H3 from Microplitis demolitor bracovirus localize to focal adhesions and are antiphagocytic in insect immune cells. J. Virol. 81: 1209-1219.

Pruijssers A. J., et al. 2009. Infection by a symbiotic polydnavirus induces wasting and inhibits metamorphosis of the moth Pseudoplusia includens. J. Exp. Biol. 212: 2998-3006.

Stoltz D. B. 1993. The polydnavirus life cycle, p. 167-187 in Thompson S. N., Federici B. A., Beckage N. E., editors. (ed.), Parasites and pathogens of insects, vol. 1 Parasites. Academic Press, San Diego, CA.

Stoltz D. B., Guzo D., Cook D. 1986. Studies of polydnavirus transmission. Virology 155: 120-131.

Strand M. R. 1990. Characterization of larval development in Pseudoplusia includens (Lepidoptera, Noctuidae). Ann. Entomol. Soc. Am. 83: 538-544.

Strand M. R. 1994. Microplitis demolitor polydnavirus infects and expresses in specific morphotypes of Pseudoplusia includens haemocytes. J. Gen. Virol. 75: 3007-3020.

Strand M. R. 2009. The interactions between polydnavirus-carrying parasitoids and their lepidopteran hosts, p. 321-336 in Goldsmith M. R., Marec F., editors. (ed.), Molecular biology and genetics of the Lepidoptera. CRC Press, Boca Raton, FL.

Strand M. R. 2010. Polydnaviruses, p. 171-197 in Asgari S., Johnson K. N., editors. (ed.), Insect virology. Caister Academic Press, Norwich, United Kingdom.

Strand M. R., Noda T. 1991. Alterations in the haemocytes of Pseudoplusia includens after parasitism by Microplitis demolitor. J. Insect Physiol. 37: 839-850.

Strand M. R., Pech L. L. 1995. Microplitis demolitor polydnavirus induces apoptosis of a specific haemocyte morphotype in Pseudoplusia includens. J. Gen. Virol. 76: 283-291.

Strand M. R., McKenzie D. I., Grassl V., Dover B. A., Aiken J. M. 1992. Persistence and expression of Microplitis demolitor PDV in Pseudoplusia includens. J. Gen. Virol. 73: 1627-1635.

Strand M. R., Witherell R. A., Trudeau D. 1997. Two Microplitis demolitor PDV mRNAs expressed in hemocytes of Pseudoplusia includens contain a common cysteine-rich domain. J. Virol. 71: 2146-2156.

Suderman R. J., Pruijssers A. J., Strand M. R. 2008. Protein tyrosine phosphatase-H2 from a polydnavirus induces apoptosis of insect cells. J. Gen. Virol. 89: 1411-1420.

Theilmann D. A., Summers M. D. 1986. Molecular analysis of Campoletis sonorensis virus DNA in the lepidopteran host Heliothis virescens. J. Gen. Virol. 67: 1961-1969.

Trudeau D., Witherell R. A., Strand M. R. 2000. Characterization of two novel Microplitis demolitor PDV mRNAs expressed in Pseudoplusia includens haemocytes. J. Gen. Virol. 81: 3049-3058.

Volkoff A.-N., et al. 2001. Persistent expression of a newly characterized Hyposoter didymator polydnavirus gene in long-term infected lepidopteran cell lines. J. Gen. Virol. 82: 963-969.

Webb B. A., Strand M. R. 2005. The biology and genomics of polydnaviruses, p. 323-360 in Gilbert L. I., Iatrou K., Gill S. S., editors. (ed.), Comprehensive molecular insect science, vol. 6 Elsevier, San Diego, CA.

Webb B. A., et al. 2006. Polydnavirus genomes reflect their dual roles as mutualists and pathogens. Virology 347: 160-174.

Whitfield J. B. 2002. Estimating the age of the polydnavirus/braconid wasp symbiosis. Proc. Natl. Acad. Sci. U. S. A. 99: 7508-7513.

Yang C. C., et al. 1997. Cellular recombination pathways and viral terminal repeat hairpin structures are sufficient for adeno-associated virus integration in vitro and in vivo. J. Virol. 71: 9231-9247.

Zuker M. 2003. Mfold Web server for nucleic acid folding and hybridization prediction. Nucleic Acids Res. 31: 3406-3415.

International Search Report of Related Application No. PCT/US2012/052476, mailed Apr. 4, 2013.

\* cited by examiner

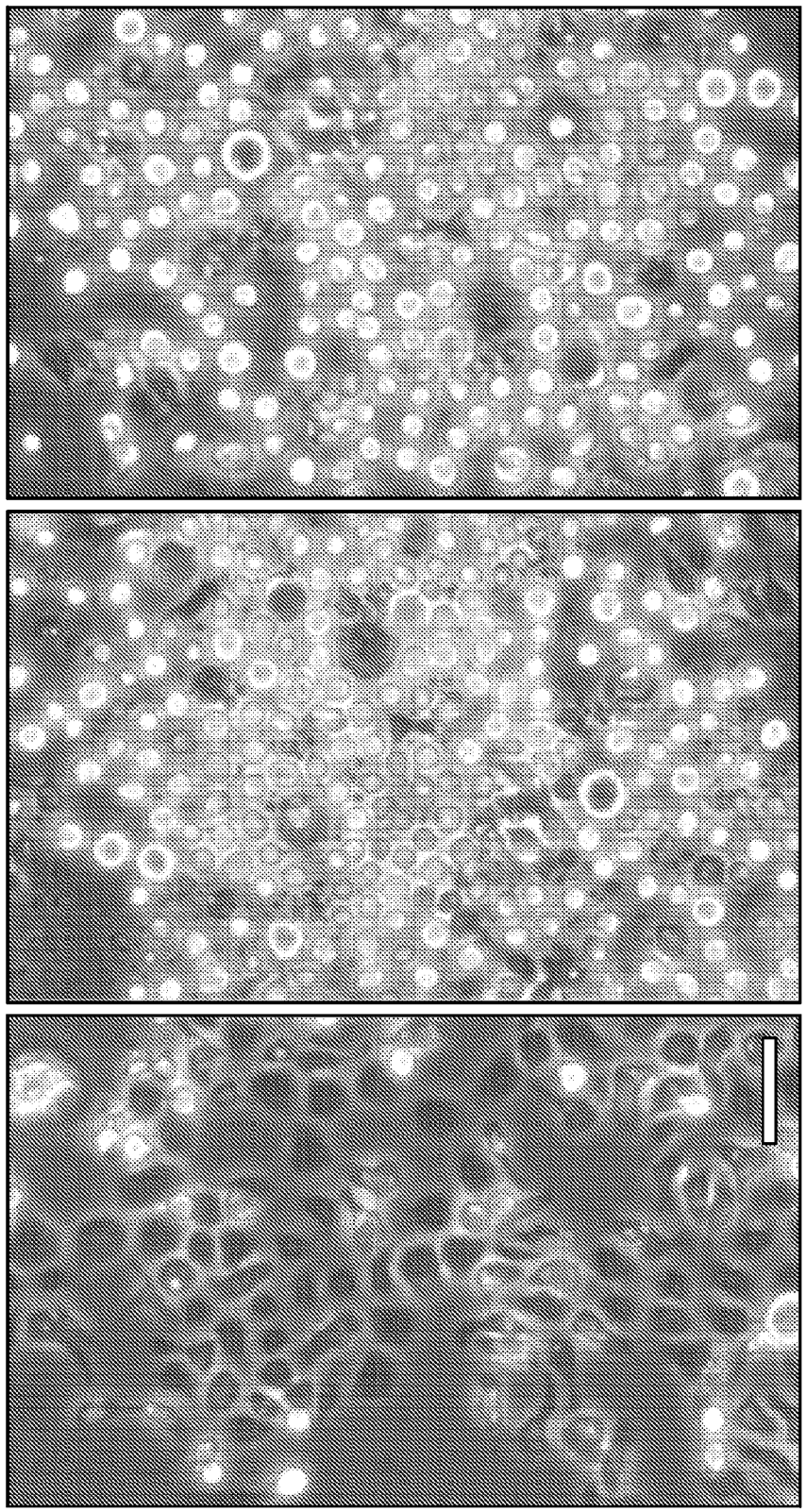

FIG. 4A

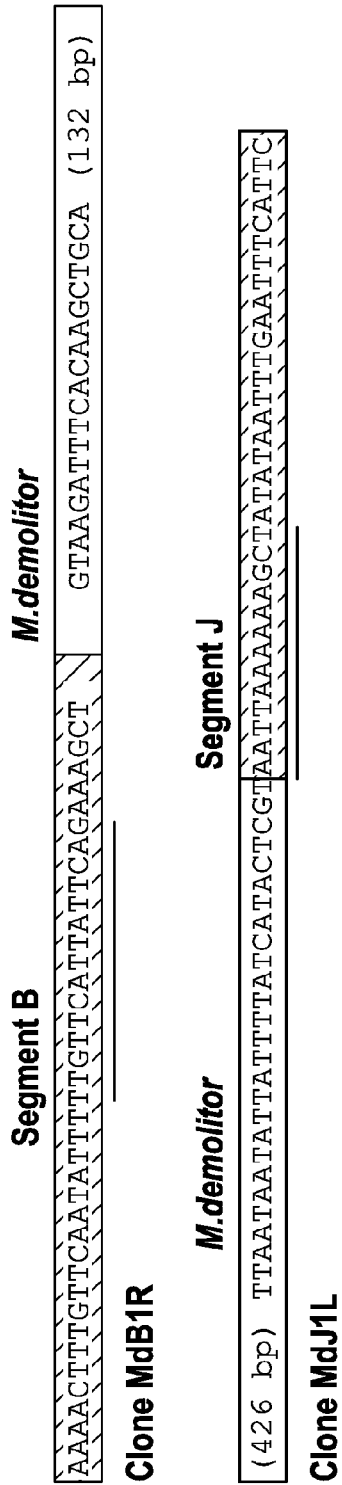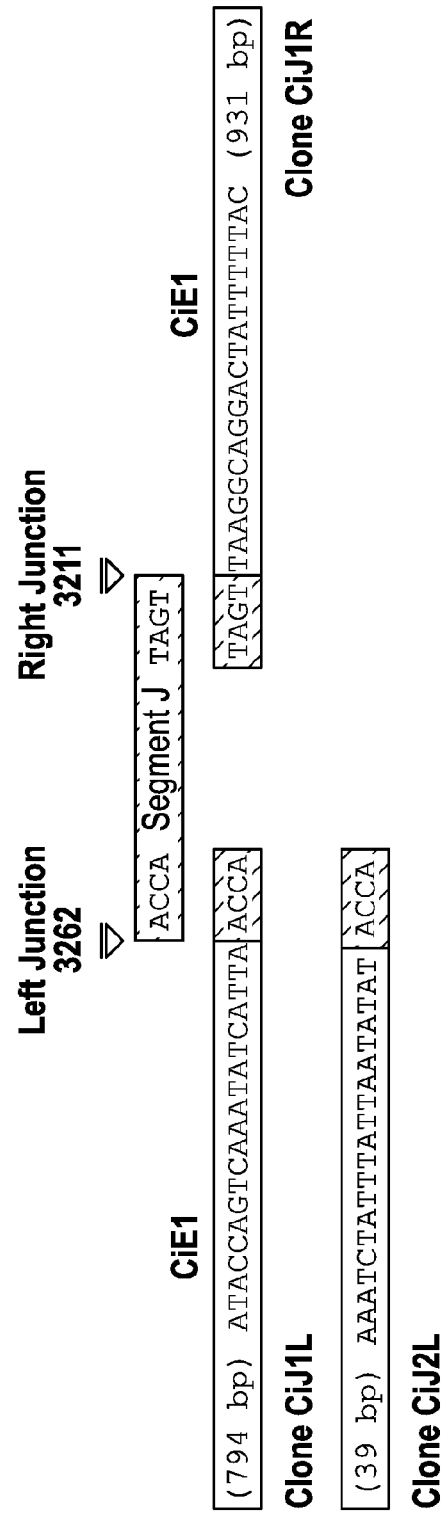
FIG. 4C
FIG. 5A

Segment J

(3182) GAA AATTTCTTGATGG GTTG AGTAAACGATTCTCAGTTTTGTATGAG
                                                          A
                                                          T
(3291) CTG TTAAAGAACTACC TCAG CCAGCTGGAATCAATTAAACATACCCC

Segment C

(2644) GAAATTTTC CCTGACGA GA TCGCC ACGAGCCAGAACAGTTTGTTCGAAG
                                                          A
                                                          /
(2755) CTTTAAAAG GGACTGCT AC GATAC CCTAGT GGATCA TCCGAAATTGTTCATTACATACCTT

FIG. 8A

POLYDNAVIRUS DELIVERY CONSTRUCTS

CROSS-REFERENCE TO RELATED APPLICATIONS

This application claims benefit of U.S. Provisional Application No. 61/527,899, filed Aug. 26, 2011, which is hereby incorporated herein by reference in its entirety.

STATEMENTS REGARDING FEDERALLY FUNDED RESEARCH

This invention was made with government funding under Grant No. 2009035020-5250 from the United States Department of Agriculture and Grant No. IOS0749450 from the National Science Foundation. The government has certain rights in this invention.

BACKGROUND

Transgenic approaches for introducing exogenous DNA into genomes is useful in making genetically modified cells. Transposon-based vectors are used for germline transformation of insects. Transposon insertion usually requires only a few specific base pairs at the target locus, which are spread randomly within the genome. Thus, transposition is undirected and transgenes embed themselves in diverse chromosomal locations. Because of cis-regulatory elements and other factors, transposon-mediated insertion of transgenes also commonly experience position effects, which result in variable expression and stability. The efficiency of germline transformation using transposon-based vectors is often quite low.

SUMMARY

Provided herein are methods of producing a genetically modified cell by introducing a polydnavirus delivery construct to a target cell. The method can be performed in vitro, e.g. on an isolated cell, or in vivo, e.g., to a cell in an animal. The polydnavirus delivery construct can comprise an exogenous nucleic acid, which is introduced into the target cell to form a genetically modified cell comprising the exogenous nucleic acid. The exogenous nucleic acid is optionally integrated into the cell's genomic DNA. Therefore, the method can further involve introducing to the cell an integrase, or a nucleic acid encoding an integrase, that is suitable for integrating the exogenous nucleic acid into genomic DNA of the target cell. For example, the integrase can be a parasitoid wasp integrase.

Also provided herein are polydnavirus delivery constructs containing an exogenous nucleic acid and genetically modified cells containing the disclosed polydnavirus delivery constructs. Also provided are polydnavirus virions containing the polydnavirus delivery constructs encapsidated with polydnavirus capsid proteins. Also provided are cells containing polydnavirus delivery constructs and nucleic acids encoding polydnavirus capsid proteins operably linked to expression control sequences. Activation of the expression control sequence results in encapsidation of the polydnavirus delivery constructs and production of are polydnavirus virions.

In vitro methods of identifying a transformed cell are provided herein. The methods comprise introducing a vector to an adherent cell. The vector can comprise a nucleotide sequence encoding a Glc polypeptide. The adherent cell is cultured under conditions that allow for expression of the Glc polypeptide. Expression of the Glc polypeptide results in a transformed cell, wherein the transformed cell is identified by a loss of adherency. Also provided are vectors comprising a nucleotide sequence encoding a Glc polypeptide.

The details of one or more embodiments are set forth in the accompanying drawings and the description below. Other features, objects, and advantages will be apparent from the description and drawings, and from the claims.

DESCRIPTION OF DRAWINGS

FIG. 1A shows a phase contrast micrograph of uninfected CiE1 cells. Note that cells are strongly adhered to and spread on the surface of culture plates. Scale bar equals 100 µm. FIG. 1B shows a phase contrast micrograph of CiE1 cells 72 hours post infection by MdBV. FIG. 1C shows a phase contrast micrograph of CiE1 cells 8 months post-infection by 609 MdBV. Inspection of FIG. 1B shows that most cells are rounded and that numerous small blebs are present due to apoptosis while FIG. 1C shows that most cells remain rounded but few blebs are present.

FIG. 3 shows MdBV genomic segments B, C, and J are integrated in adult male *M. demolitor* and CiE1 cells 21 days post-infection with MdBV.

FIG. 4 shows a wasp excision/integration motif (WIM) identifies the site of integration of MdBV genomic segments B, C, and J in *M. demolitor* but not CiE1 cells. FIG. 4A shows an alignment of the predicted WIM on selected MdBV genomic segments. The location of the motif on each segment is indicated to the left. Identical nucleotides are indicated in black. The dark line above and below the alignment indicates the predicted site of integration of the corresponding proviral DNA in *M. demolitor*. Seg. B (SEQ ID NO:5); Seg. C (SEQ ID NO:6); Seq. E (SEQ ID NO:7); Seg. G (SEQ ID NO:8); Seg. H (SEQ ID NO:9); Seg. J (SEQ ID NO:10); Seg. K (SEQ ID NO:11); Seg. L (SEQ ID NO:12); Seg. M (SEQ ID NO:13); Seg. o (SEQ ID NO:14). FIG. 4C shows schematics illustrating the right segment B-*M. demolitor* junction sequence (SEQ ID NO:17) and left segment J-*M. demolitor* junction sequence (SEQ ID NO:18) cloned by inverse PCR. The MdBV sequence is highlighted in black and the *M. demolitor* genomic sequence is highlighted in white. Note that the right boundary border for segment B is identified by the tetramer AGCT while the right boundary for segment J is identified by the tetramer AATT as underlined in FIG. 4A. The cloned and analyzed *M. demolitor* sequence flanking segment B is 132 bp while the sequence for segment J is 426 bp.

FIG. 5 shows that inverse PCR clones confirm that MdBV segments J and C integrate into the genome of CiE1 cells. FIG. 5A shows a schematic illustrating the two left (COIL (SEQ ID NO:19), CiJ2L (SEQ ID NO:20)) and one right (CiJ1R) (SEQ ID NO:21) segment J-CiE1 junction sequences cloned by inverse PCR. Each junction clone is aligned with segment J linearized at nt 3262 (left) and 3211 (right). The MdBV sequence in each junction clone is highlighted in black and CiE1 genomic sequence is highlighted in white. Note that the segment J boundary for both left clones corresponds to nt 3262 and the tetramer ACCA, while the boundary for the right junction clone corresponds to nt 3211 and the tetramer TAGT. The analyzed CiE1 sequences for the two left junction clones are 794 and 39 bp long respectively, while the CiE1 sequence for the right junction clone is 931 bp.

FIG. 6 shows PCR-based integration assays and inverse PCR clones that confirm MdBV segments integrate into the genome of parasitized *P. includens*.

FIG. 7 shows that integration of MdBV genomic DNAs is non-random.

FIG. 8 shows MdBV genomic DNAs contain similar host integration motifs (HIMs). FIG. 8A shows predicted stem-loop structures for the segment J (SEQ ID NO:30) and C (SEQ ID NO:31) HIMs generated by Mfold. Gray highlights nts that form the base of the stem, black highlights the tetramers that identify the boundary site of integration of each segment into host cells, and white highlights the predicted loop domain that is deleted with integration into the host genome.

FIG. 11B is a low-magnification image of calyx cells from a stage 3 pupa. Note the enlarged nucleus (N) for the calyx cell in the center of the image. Arrows indicate regions in the nucleus where MdBV particles are being assembled in proximity to virogenic stroma. Bar=1.5 µm. FIG. 11C is a high-magnification image of a calyx cell nucleus from a stage 3 pupa. The arrow indicates a region where both empty viral envelopes and envelopes containing a capsid are visible, while below this region are an abundance of mature virions (V). Bar=100 nm. FIG. 11D is a high-magnification image of a lysed calyx cell from a stage 4 pupa. The nuclear membrane of the cell has deteriorated, resulting in release of mature virions (V) and dense nuclear chromatin (NC). Bar=500 nm. FIG. 11E is a low-magnification image from a day 1 adult showing densely packed MdBV virions in the calyx lumen (CL) that is adjacent to an *M. demolitor* egg (EG). Bar=1 µm.

DETAILED DESCRIPTION

Provided herein are methods of producing a genetically modified cell. The methods comprise introducing a polydnavirus delivery construct to the cell. The method can be performed in vitro, e.g. on an isolated cell, or in vivo, e.g., to a cell in an animal. The polydnavirus delivery construct can comprise an exogenous nucleic acid to form a genetically modified cell comprising the exogenous nucleic acid. Optionally, the polydnavirus delivery construct integrates into the genome of the cell. Also provided are genetically modified cells produced by any of the methods described herein.

The disclosed method can involve introducing to the cell an integrase, or a nucleic acid encoding an integrase, that is suitable for integrating the exogenous nucleic acid into genomic DNA of the target cell. For example, the integrase can be a parasitoid wasp integrase as identified from the integrated proviral genome of *Microplitis demolitor* bracovirus (GenBank accession numbers JO913492 through JO979916 and JR139425 through JR139430).

Figure 8B:
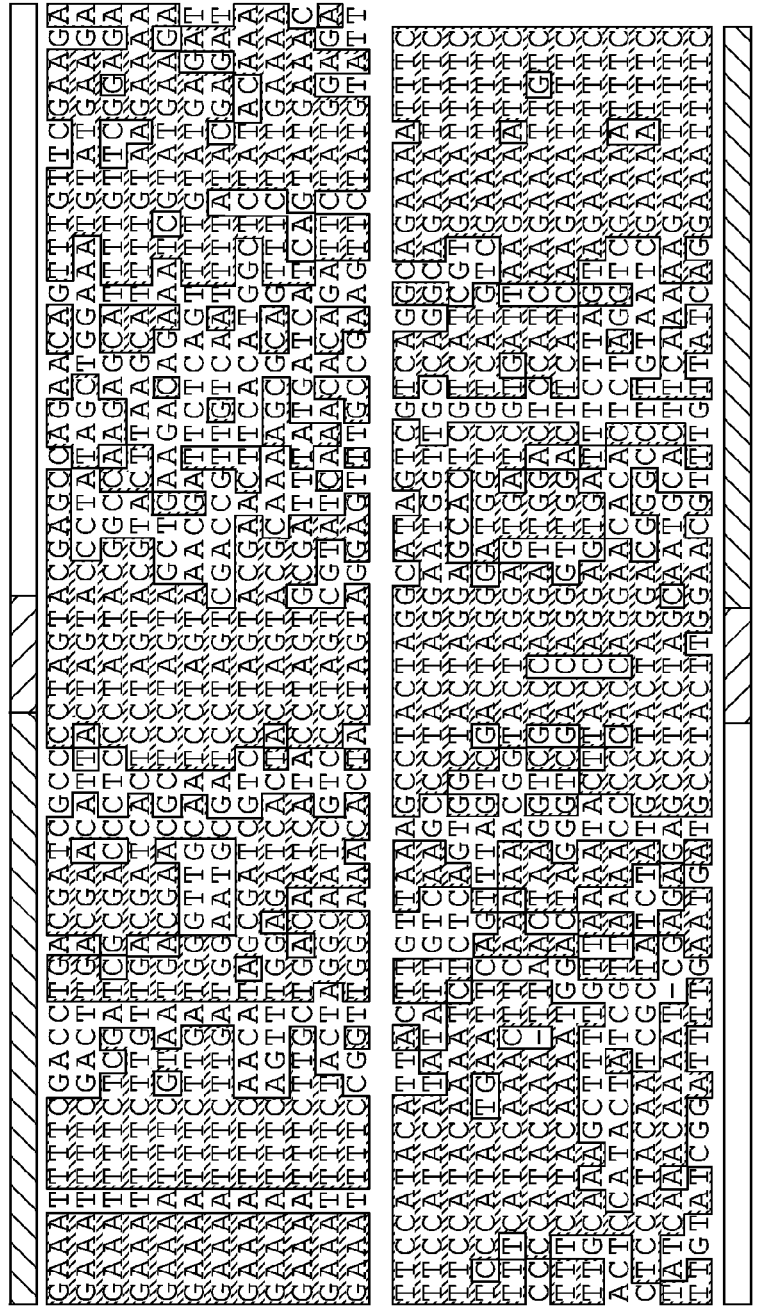
FIG. 8B shows a sequence alignment of the HIMs from selected MdBV genomic segments. The position of the motif on each segment is indicated to the left. Identical nucleotides are indicated in black. The gray, black, and white lines above and below the alignment correspond to the stem and loop regions shown in FIG. 8A. Seg. C (SEQ ID NO:32); Seg. O (SEQ ID NO:33); Seg. F (SEQ ID NO:34); Seg. I (SEQ ID NO:35); Seg. G (SEQ ID NO:36); Seg. J (SEQ ID NO:37); Seg. N (SEQ ID NO:38); Seg. B (SEQ ID NO:39); Seg. E (SEQ ID NO:40); Seg. K (SEQ ID NO:41); Seg. H (SEQ ID NO:42); Seg. L (SEQ ID NO:43).
Figure 9:
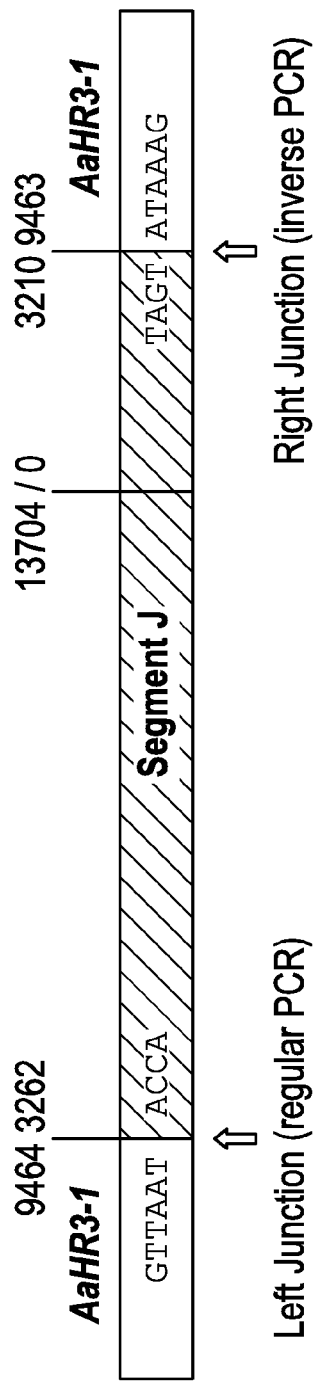
FIG. 9 shows a schematic demonstrating the left and right insertion site junctions (shown in SEQ ID NO:46 and SEQ ID NO:47, respectively) generated by inverse PCR for segment J in AaG2 cells from *A. aegypti*. Host sequence analysis identified the location of the junction as the 3′ untranslated region (UTR) of the AaHR3-1 gene.
Figure 10:
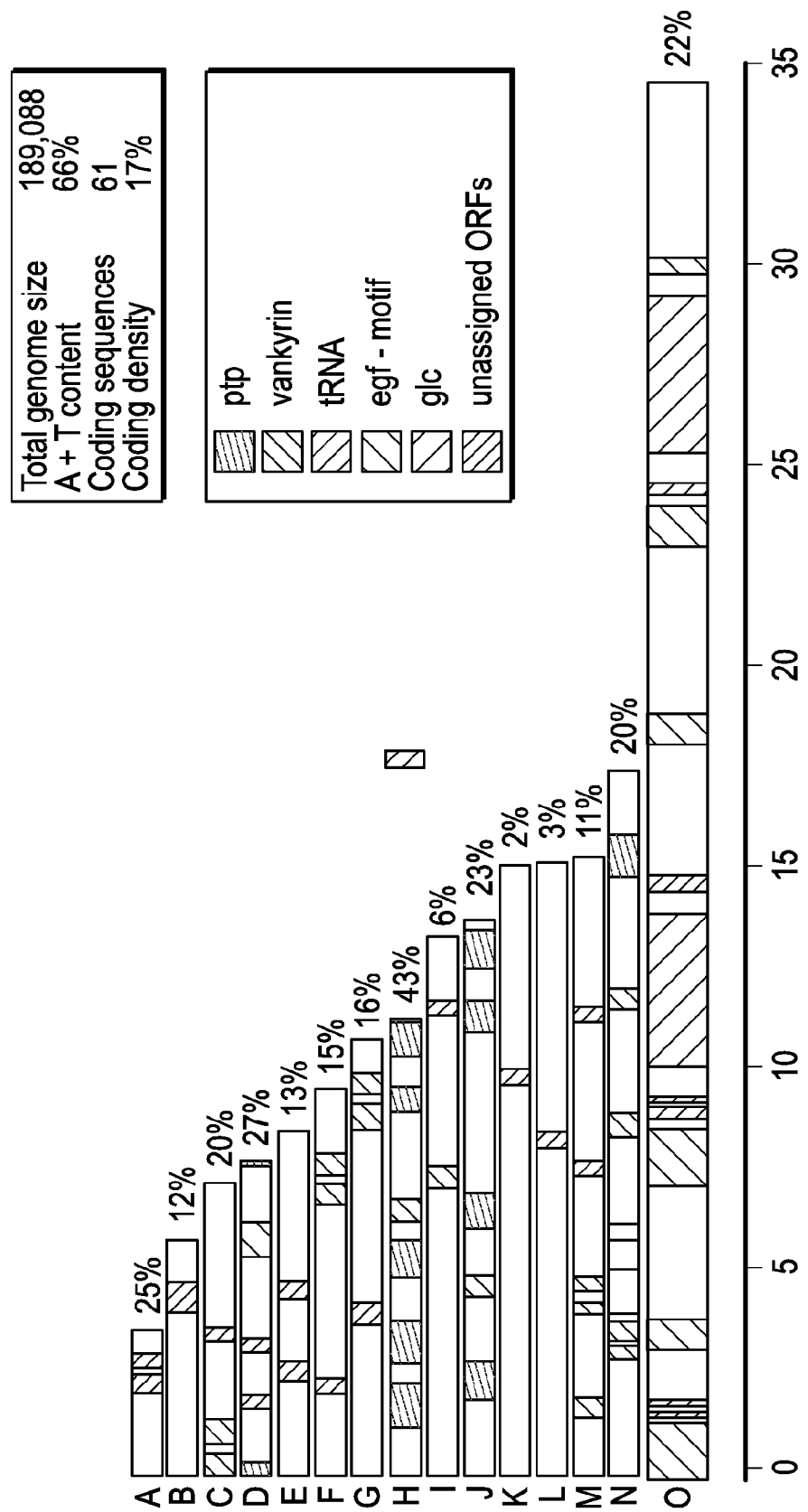
FIG. 10 shows a schematic of the MdBV genome. Genomic segments (A-O) are linearized. Size (kilobases (kb)) is indicated along the x axis and coding density is indicated to the right of each segment. The major gene families and their location in the genome are labeled.

Also provided are polydnavirus delivery constructs comprising an exogenous nucleic acid. The polydnavirus delivery construct can, for example, be derived from a virus selected from the genus of Bracovirus. Optionally, the polydnavirus delivery construct is derived from *Microplitis demolitor* bracovirus (MbDV). The polydnavirus delivery construct can, for example, further comprise at least one host integration motif as identified under GenBank accession numbers AY887894, AY875680 through AY875690, AY848690, AY842013, and DQ000240. The host integration motif can be selected from the group consisting of SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, and SEQ ID NO:43, as shown in FIG. 8B. Optionally, the host integration motif is comprised within an MdBV segment. The MdBV segment can be selected from the group consisting of segment A, segment B, segment C, segment D, segment E, segment F, segment G, segment H, segment I, segment J, segment K, segment L, segment M, segment N, and segment O as shown in FIG. 10.

The exogenous nucleic acid can, for example, encode a polypeptide of interest to be expressed in the genetically modified cell for production of recombinant proteins in cell culture or mature organisms. The polypeptide of interest can, for example, be selected to provide a desired function. The polypeptide can comprise a detectable tag. The detectable tag can be selected from the group consisting of a histidine tag, a FLAG™ tag, a GST tag, a hemagglutinin tag, and a fluorescent tag (e.g., GFP, YFP, RFP).

The exogenous nucleic acid can, for example, comprise a nucleotide sequence of about 50 to about 35,000 nucleotides. Optionally, the nucleotide sequence is about 1,000 to about 20,000 nucleotides. Thus, the nucleotide sequence can be about 50; 100, 1,000; 5,000; 10,000; 15,000; 20,000; 25,000, 30,000; or 35,000 nucleotides or any number in between. As used herein, an exogenous nucleic acid is a nucleic acid that is generally not present in a target cell. Thus, an exogenous or heterologous nucleic acid can be derived from a different species than the target cell and be introduced to the target cell through the polydnavirus delivery constructs described herein.

The disclosed polydnavirus delivery constructs can be delivered to cells by transfection, electroporation, or by use of polydnavirus virions. Assembly of polydnavirus virions requires multiple genes including subunits of a bracovirus RNA polymerase (p47, lef-4, lef-8, lef-9), nucleocapsid proteins (vlf-1b, integrase, 38K, vp91, vp39), and envelope proteins (p74, pif-1-3, 19 kDa, odv-e56, odv-e66).

Also provided are polydnavirus virions containing the disclosed polydnavirus delivery constructs encapsidated with polydnavirus capsid proteins. Also provided are cells containing polydnavirus delivery constructs and nucleic acids encoding polydnavirus capsid proteins operably linked to expression control sequences. In these embodiments, activation of the expression control sequence results in encapsidation of the polydnavirus delivery constructs.

The target cell can be a cell in or derived from an arthropod, a bird, a reptile, an amphibian, a fish, or a mammal. Preferably, the target cell is a cell from an arthropod, such as an insect, chelicerate, or crustacean. For example, the arthropod can be a production insect, such as a honey bee or silk moth. The arthropod may also be a farmed crutacea, such as a shrimp, lobster, or crab. Alternatively, the arthropod can be a pest, such as an arthropod that can cause disease or damage crops. For example, the arthropod can be an aphid, beetle, mealybug, caterpillar, mite, scale, fly, or mosquito. A target cell can be in or derived from an adult, a newborn, or an embryo. Thus, the target cell can, for example, be an embryonic or adult stem cell.

Also provided are cells comprising a polydnavirus delivery construct. The genetically modified cells can, for example, comprise any of the polydnavirus delivery constructs described herein.

Provided herein are in vitro methods of identifying a transformed cell. The methods comprise introducing a vector to an adherent cell. The vector can comprise a nucleotide sequence encoding a Glc polypeptide. The adherent cell is cultured under conditions allowing for the expression of the Glc polypeptide. Expression of the Glc polypeptide results in a transformed cell, wherein the transformed cell is identified by a loss of adherency.

Also provided herein are vectors comprising an exogenous nucleotide sequence encoding a Glc polypeptide. Optionally, the vector further comprises a second exogenous nucleic acid. Optionally, the vector further comprises an exogenous nucleic acid encoding an antibiotic resistance. Further provided herein are substrates (e.g., plates, wells, culture dishes, arrays) comprising any of the vectors described herein.

Optionally, the nucleotide sequence encoding the Glc polypeptide is selected from a virus from a Bracovirus genus. The virus can, for example, comprise the *Micropolitis demolitor* bracovirus (MdBV).

The Glc polypeptide functions as a selectable marker in transformed cells, as adherent cells transformed with the Glc polypeptide become non-adherent. The recombinant polypeptides described are produced for enhanced expression of a polypeptide of interest, which can be used for purification purposes.

As with all peptides, polypeptides, and proteins, including fragments thereof, it is understood that additional modifications in the amino acid sequence of Glc polypeptide or recombinant polypeptides can occur that do not alter the function of the peptides, polypeptides, or proteins. Such modifications include conservative amino acid substitutions and are discussed in greater detail below. Thus, the polypeptides described herein can be modified so long as the desired function is maintained. It is understood that one way to define any known modifications and derivatives or those that might arise, of the disclosed genes and proteins herein, is through defining the modifications and derivatives in terms of identity to specific known sequences. Specifically disclosed are polypeptides which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent identity to the Glc polypeptide or recombinant polypeptides provided herein. Those of skill in the art readily understand how to determine the identity of two polypeptides. For example, the identity can be calculated after aligning the two sequences so that the identity is at its highest level.

Another way of calculating identity can be performed by published algorithms. Optimal alignment of sequences for comparison may be conducted by the local identity algorithm of Smith and Waterman Adv. Appl. Math. 2:482 (1981), by the identity alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of identity can be obtained for nucleic acids by, for example, the algorithms disclosed in Zuker, Science 244:48-52 (1989); Jaeger et al., Proc. Natl. Acad. Sci. USA 86:7706-10 (1989); Jaeger et al. Methods Enzymol. 183:281-306 (1989), which are herein incorporated by reference for at least material related to nucleic acid alignment. It is understood that any of the methods typically can be used and that in certain instances the results of these various methods may differ, but the skilled artisan understands if identity is found with at least one of these methods, the sequences would be said to have the stated identity, and be disclosed herein.

Protein modifications include amino acid sequence modifications. Modifications in amino acid sequence may arise naturally as allelic variations (e.g., due to genetic polymorphism), may be produced by human intervention (e.g., by mutagenesis of cloned DNA sequences), or may arise due to environmental influence (e.g., exposure to ultraviolet light), such as induced point, deletion, insertion and substitution mutants. These modifications can result in changes in the amino acid sequence, provide silent mutations, modify a restriction site, or provide other specific mutations. Amino acid sequence modifications typically fall into one or more of three classes: substitutional, insertional, or deletional modifications. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional modifications are those in which at least one residue has been removed and a different residue inserted in its place. Such substitutions generally are made in accordance with the following Table 1 and are referred to as conservative substitutions.

TABLE 1

Amino Acid Substitutions

| Amino Acid | Substitutions (others are known in the art) |
|---|---|
| Ala | Ser, Gly, Cys |
| Arg | Lys, Gln, Met, Ile |
| Asn | Gln, His, Glu, Asp |
| Asp | Glu, Asn, Gln |
| Cys | Ser, Met, Thr |
| Gln | Asn, Lys, Glu, Asp |
| Glu | Asp, Asn, Gln |
| Gly | Pro, Ala |
| His | Asn, Gln |
| Ile | Leu, Val, Met |
| Leu | Ile, Val, Met |
| Lys | Arg, Gln, Met, Ile |
| Met | Leu, Ile, Val |
| Phe | Met, Leu, Tyr, Trp, His |
| Ser | Thr, Met, Cys |
| Thr | Ser, Met, Val |
| Trp | Tyr, Phe |

TABLE 1-continued

Amino Acid Substitutions

| Amino Acid | Substitutions (others are known in the art) |
|---|---|
| Tyr | Trp, Phe, His |
| Val | Ile, Leu, Met |

Modifications, including the specific amino acid substitutions, are made by known methods including the methods described in the Examples below. By way of example, modifications are made by site-specific mutagenesis of nucleotides in the DNA encoding the protein, thereby producing DNA encoding the modification, and thereafter expressing the DNA in recombinant cell culture. Techniques for making substitution mutations at predetermined sites in DNA having a known sequence are well known, for example, M13 primer mutagenesis and PCR mutagenesis.

Nucleic acids that encode the polypeptide sequences, variants, and fragments thereof are disclosed. These sequences include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequences.

Thus, provided herein are polydnavirus delivery constructs comprising an exogenous nucleic acid. As used herein a polydnavirus delivery construct is defined as a construct which contains at least a portion of a polydnavirus. Thus, the polydnavirus delivery constructs can, for example, be comprise a vector backbone derived largely from two classes of vectors: viral based delivery vectors and non-viral based delivery vectors. Such vectors are well known in the art and readily adaptable for use with the methods described herein.

As used herein, plasmid or viral vectors are agents that transport the disclosed exogenous nucleic acids into the cell without degradation and include a promoter yielding expression of the nucleic acid molecule and/or polypeptide in the cells into which it is delivered. Viral vectors are, for example, Adenovirus, Adeno-associated virus, herpes virus, Vaccinia virus, Polio virus, Sindbis, and other RNA viruses, including these viruses with the HIV backbone. Also preferred are any viral families which share the properties of these viruses which make them suitable for use as vectors. Retroviral vectors, in general are described by Coffin et al., *Retorviruses*, Cold Spring Harbor Laboratory Press (1997), which is incorporated by reference herein for the vectors and methods of making them. The construction of replication-defective adenoviruses has been described (Berkner et al., J. Virol. 61:1213-20 (1987); Massie et al., Mol. Cell. Biol. 6:2872-83 (1986); Haj-Ahmad et al., J. Virol. 57:267-74 (1986); Davidson et al., J. Virol. 61:1226-39 (1987); Zhang et al., BioTechniques 15:868-72 (1993)). The benefit and the use of these viruses as vectors is that they are limited in the extent to which they can spread to other cell types, since they can replicate within an initial infected cell, but are unable to form new infections viral particles. Recombinant adenoviruses have been shown to achieve high efficiency after direct, in vivo delivery to airway epithelium, hepatocytes, vascular endothelium, CNS parenchyma, and a number of other tissue sites. Other useful systems include, for example, replicating and host-restricted non-replicating vaccinia virus vectors.

Non-viral based vectors can include expression vectors comprising the exogenous nucleic acid molecules, wherein the nucleic acids are operably linked to an expression control sequence. Suitable vector backbones include, for example, those routinely used in the art such as plasmids, artificial chromosomes, BACs, YACs, or PACs. Numerous vectors and expression systems are commercially available from such corporations as Novagen (Madison, Wis.), Clonetech (Palo Alto, Calif.), Stratagene (La Jolla, Calif.), and Invitrogen/Life Technologies (Carlsbad, Calif.). Vectors typically contain one or more regulatory regions. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, and introns.

Preferred promoters controlling transcription from vectors in mammalian host cells may be obtained from various sources, for example, the genomes of viruses such as polyoma, Simian Virus 40 (SV40), adenovirus, retroviruses, hepatitis B virus, and most preferably cytomegalovirus (CMV), or from heterologous mammalian promoters, e.g. β-actin promoter or EF1α promoter, or from hybrid or chimeric promoters (e.g., CMV promoter fused to the β-actin promoter). Preferred promoters for insect cells derived from Lepdioptera (moths and butterflies) include the early promoters IE1 and IE2 from the baculovirus AcMNPV, as well as the late promoters P10 and pol from AcMNPV. Preferred promoters for cells derived from other insects like Diptera (mosquitoes and flies) include the heat shock promoter from *Drosophila*. Of course, other promoters from the host cell or related species are also useful herein.

Enhancer generally refers to a sequence of DNA that functions at no fixed distance from the transcription start site and can be either 5' or 3' to the transcription unit. Furthermore, enhancers can be within an intron as well as within the coding sequence itself. They are usually between 10 and 300 base pairs (bp) in length, and they function in cis. Enhancers usually function to increase transcription from nearby promoters. Enhancers can also contain response elements that mediate the regulation of transcription. While many enhancer sequences are known from mammalian genes (globin, elastase, albumin, fetoprotein, and insulin), typically one will use an enhancer from a eukaryotic cell virus for general expression. Preferred examples are the SV40 enhancer on the late side of the replication origin, the cytomegalovirus early promoter enhancer, the polyoma enhancer on the late side of the replication origin, and adenovirus enhancers.

The promoter and/or the enhancer can be inducible (e.g. chemically or physically regulated). A chemically regulated promoter and/or enhancer can, for example, be regulated by the presence of alcohol, tetracycline, a steroid, or a metal. A physically regulated promoter and/or enhancer can, for example, be regulated by environmental factors, such as temperature and light. Optionally, the promoter and/or enhancer region can act as a constitutive promoter and/or enhancer to maximize the expression of the region of the transcription unit to be transcribed. In certain vectors, the promoter and/or enhancer region can be active in a cell type specific manner. Optionally, in certain vectors, the promoter and/or enhancer region can be active in all eukaryotic cells, independent of cell type. Preferred promoters of this type are the CMV promoter, the SV40 promoter, the β-actin promoter, the EF1α promoter, and the retroviral long terminal repeat (LTR).

The vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the E. coli lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Example 1

MdBV Genomic Integration into Naturally Parasitized P. includens

Materials and Methods
Insects and Cell Lines.
M. demolitor and P. includens were reared at 27° C. with a 16 hour light, 8 hour dark photoperiod as previously described (Strand, Ann. Entomol. Soc. Am. 83:538-44 (1990); Strand, "Polydnaviruses," in Insect Virology, Caister Academic Press, Norwich, UK, p. 171-197 (2010)). Hosts used in the study were parasitized as third instars. A single wasp offspring emerges from the host's body on day 7 or 8 to pupate within a silken cocoon followed by emergence into an adult four days later (Pruijssers and Strand, J. Exp. Biol. 212:2998-3006 (2009)). CiE1 cells were cultured in Sf-900 medium (Gibco®; Invitrogen; Carlsbad, Calif.) supplemented with 5% fetal calf serum (Hyclone; Thermo Scientific; Rockford, Ill.) (Johnson et al., Insect Biochem. Mol. Biol. 40:394-404 (2010)). Non-infected cells were maintained and passaged weekly as strongly adherent cells in Corning 75 cm$^2$ tissue-culture flasks. MdBV-infected cells became non-adherent but were maintained and passaged identically to non-infected cells.

MdBV Collection and Nomenclature.
MdBV virions were collected from the reproductive tract of adult female wasps in calyx fluid as previously described (Beck and Strand, Virology 314:521-35 (2003); Strand et al., J. Gen. Virol. 73:1627-35 (1992)). As is convention in the PDV literature, the amount of MdBV collected from the reproductive tract of a single adult female is defined as one wasp equivalent, which for MdBV contains on average $1 \times 10^{10}$ virions (Beck et al., Virology 359:179-89 (2007)). The encapsidated genome of MdBV was previously deposited in Genbank as individual genomic segments under the accession numbers AY887894, AY875680-AY875690, AY848690, AY842013 and DQ000240 (Webb et al., Virology 347:160-74 (2006)). Each genomic segment is named by large case letter from smallest (genomic segment A, 3433 base pairs (bp)) to largest (genomic segment O, 34,355 bp) (Webb et al., Virology 347:160-74 (2006)). Nucleotide (nt) positions referred to in the study for a given segment correspond to the aforementioned Genbank submissions, while the abundance of each genomic segment in calyx fluid was previously determined (Beck et al., Virology 359:179-89 (2007)). Most predicted genes are named by their location on a given genomic segment (Bitra et al., J. gen. Virol. (2011)). Thus, members of the ptp gene family consist of one predicted gene located on genomic segment D (ptp-D1), five on segment H (ptp-H1, 2, 3, 4, 5), four on segment J (ptp-J1, 2, 3, 4), and three on segment N (ptp-N1, 2, 3) (Pruijssers and Strand, J. Virol. 81:1209-19 (2007); Webb et al., Virology 347:160-74 (2006)). Members of the ank gene family are named similarly (ank-C1, C2, F4, F5, G3, G4, H4, I1, J4, N1, N4, N5), whereas all egf (egf0.4, egf1.0, egf1.5) and glc genes (glc1.8, glc3.2) reside on genomic segment O and are named by the size of their corresponding cDNAs (Beck and Strand, Proc. Natl. Acad. Sci. USA 104:19267-72 (2007); Strand et al., J. Virol. 71:2146-56 (1997); Trudeau et al., J. Gen. Vriol. 81:3049-58 (2000); Webb et al., Virology 347: 160-74 (2006)).

Total RNA Isolation and RT-PCR Assays.
MdBV-infected CiE1 cells were collected by centrifugation at 200×g, followed by isolation of total RNA using the High Pure RNA Isolation kit (Roche; Indianapolis, Ind.) according to the manufacturer's instructions. Quantification of RNA was done using a Nanodrop spectrometer (NanoDrop Products; Wilmington Del.). For first-strand cDNA synthesis, 100 ng of total RNA was reverse transcribed in 20 µl reactions using random hexamers and Superscript III (Invitrogen). RT-PCR reactions were run using a Biorad thermocycler and 25 µl reaction volumes containing 1 µl of cDNA and 0.2 µM of appropriate gene-specific primers. Primers used to amplify selected ptp family members were described by Pruijssers and Strand (Pruijssers and Strand, J. Virol. 81:1209-19 (2007)), primers used to amplify glc1.8/

3.2 and egf1.0/1.5 were described by Beck et al. (Beck and Strand, Proc. Natl. Acad. Sci. USA 104:19267-72 (2007)), and primers used to amplify selected ank family members were described by Bitra et al. (Bitra et al., J. Gen Virol. (2011)). Cycling conditions were as follows: initial denaturation at 94° C. for 2 minutes followed by 35 cycles at 94° C. for 20 seconds, annealing at 50° C. (ptp, glc, egf and single copy genes) or 55° C. (all ank family members) for 10 seconds, extension at 65° C. for 30 seconds, and a final extension at 72° C. for 7 minutes. Resulting products were visualized on 1% agarose gels stained with ethidium bromide (EtBr).

Immunoblotting and Immunocytochemistry.

MdBV-infected CiE1 cells were placed in lysis buffer and stored at −80° C. (Lu, J. Biol. Chem. 283:21325-33 (2008)). After determining protein concentrations using the Micro BCA Protein Assay Kit (Pierce; Rockford, Ill.), samples were resolved on 4-20% gradient SDS-PAGE gels (Lonza; Basel, Switzerland), immunoblotted onto PVDF membrane (Immobilon-P; Millipore; Billerica, Mass.), and blocked (Lu, J. Biol. Chem. 283:21325-33 (2008)). The membrane was probed with a murine monoclonal antibody (55F2E7) specific for Glc1.8 and Glc3.2 (1:10,000) (Beck and Strand, Virology 314:521-35 (2003); Trudeau et al., J. Gen. Virol. 81:3049-58 (2000)). The primary antibody was detected using a goat anti-mouse horseradish peroxidase-conjugated secondary antibody (1:20,000) (Jackson Labs; Bar Harbor, Me.), followed by visualization using a chemiluminescent substrate (ECL Advance kit, GE Healthcare) (Lu, J. Biol. Chem. 283:21325-33 (2008)). MdBV-infected CiE1 cells were processed for immunofluorescence microscopy as previously outlined (Beck and Strand, J. Virol. 79:1861-70 (2005)) by labeling with anti-Glc1.8/3.2 and an anti-mouse Alexafluor 564-conjugated secondary antibody. Samples were examined using a Leica IRE2 inverted epifluorscent microscope interfaced (Compix; Cranberry, Pa.) with SimplePCI software (Hamamatsu Corporation; Sewickly, Pa.) and a Hamamatsu digital camera (Hamamatsu Corporation) for image acquisition. Final images were assembled using Adobe Photoshop (Adobe, Inc.; San Jose, Calif.).

DNA Isolation and PCR-Based Detection of MdBV Genomic Segments.

Genomic DNA from adult male M. demolitor, MdBV-infected CiE1 cells, whole parasitized P. includens larvae (7 days post-oviposition), or hemocytes from parasitized P. includens larvae (2 hours-8 days post-parasitism) was isolated using the QIAMP DNA mini kit (Qiagen; Valencia, Calif.). For whole parasitized larvae, no M. demolitor offspring were present in the sample. MdBV genomic DNA was isolated from virions as previously described (Strand et al., J. Gen. Virol. 73:1627-35 (1992)). Genomic DNA isolated from non-infected CiE1 cells or non-parasitized P. includens also served as controls for some experiments. Detection by PCR of each MdBV segment in infected CiE1 cells was conducted using segment specific primers as previously described (Beck et al., Virology 359:179-89 (2007)). A PCR-based integration assay (Annaheim and Lanzrein, J. Gen. Virol. 8:450-7 (2007)) was used to locate domains of MdBV genomic segments B, C, and J that contained the proviral excision/integration site in M. demolitor and the site of integration into CiE1 cells and P. includens larvae. Briefly, segments B and C were divided into 4 domains and segment J was divided into 5 domains by designing overlapping primer pairs that specifically amplified each region (Table 2). PCR reactions were then run in 25 µl reactions containing 0.2 µM of each domain specific primer, 10 ng of MdBV, M. demolitor, CiE1 or P. includens DNA, 1 and 1.25 units of Hotmaster Taq polymerase (5 Prime). Cycling conditions were as follows: initial denaturation at 94° C. for 2 minutes, followed by 35 cycles of denaturation at 94° C. for 20 seconds, annealing at 50° C. for 20 seconds and extension at 65° C. for 4 minutes with final extension at 72° C. for 7 minutes.

TABLE 2

Primers used to amplify specific domains of MdBV genomic segments B, C, J.

| Domain | Forward primers (5'-3') | Reverse primers (5'-3') | Location |
|---|---|---|---|
| Segment B | | | |
| B-1 | TCGGAAAAGG CATAAGGTAA AATAAACATC (SEQ ID NO: 48) | ACGCCGCAGA ACAGCCGAGT C (SEQ ID NO: 52) | 1299-2476 |
| B-2 | CGTCGACGGG CTCTATTTCT TCAACACA (SEQ ID NO: 49) | ACCAACGAGG GATTCAAACC GCTTACTTAT (SEQ ID NO: 53) | 2318-5009 |
| B-3 | ATCTATTTCC GCTTAAAATG AGAGTATC (SEQ ID NO: 50) | CATAAAACGC AGCTGAGTAT TAGAAAG (SEQ ID NO: 54) | 4399-5687 |
| B-4 | AGTGCCAGCG ATTTTATATT CTTTTT (SEQ ID NO: 51) | AGTTCCGATG TTTATTTTAC CTTATGC (SEQ ID NO: 55) | 5040-1334 |
| Segment C | | | |
| C-1 | TGCCTGCGAC CGTGCCAATA CC (SEQ ID NO: 56) | TCCGGAACCA CAAACAATCG AAGAAATC (SEQ ID NO: 60) | 1262-3511 |
| C-2 | GTGCGGCAAT AAAAACGTAC TCGGTCATAA (SEQ ID NO: 57) | AGTGTCGCAT CAGCCTTCTC CAAAATC (SEQ ID NO: 61) | 3161-5216 |
| C-3 | GTAAAAGCC GGAACTGAAG GAATA (SEQ ID NO: 58) | AATCTGGGCG ATAGAAACGA TAGC (SEQ ID NO: 62) | 4077-5866 |
| C-4 | GTATCAGTGC GACGAGTTAA TCTGGTTGGT (SEQ ID NO: 59) | TCGCGGAGAG TATGCTTCCC TGAAC (SEQ ID NO: 63) | 5485-1637 |

TABLE 2-continued

Primers used to amplify specific domains of MdBV genomic segments B, C, J.

| Domain | Forward primers (5'-3') | Reverse primers (5'-3') | Location |
|---|---|---|---|
| Segment J | | | |
| J-1 | AATTCGGTAC TTTGCGGGTT GG (SEQ ID NO: 64) | TTGTTTGTAA ATCGTGCGTA TCAT (SEQ ID NO: 69) | 651-3538 |
| J-2 | AATTATGTCA GCAGCAGGTT CGT (SEQ ID NO: 65) | CGGGTCGTTG TGTTAATGGA TGTC (SEQ ID NO: 70) | 3118-5775 |
| J-3 | ACTTTGCGCT ATTTTCAGGG TCAG (SEQ ID NO: 66) | ATTATTTATA TTTGCGGGTT TCAC (SEQ ID NO: 71) | 5409-8215 |
| J-4 | TGTCTTCATC TTCAGGTGTT TTTGG (SEQ ID NO: 67) | ATTGTAGAGC GTGCGTATTC (SEQ ID NO: 72) | 8043-12000 |
| J-5 | TCGTTCATGG TCTGGTTGGA GG (SEQ ID NO: 68) | ATTGGCCATG AGTTGATACT (SEQ ID NO: 73) | 11603-1261 |

Inverse PCR.

Inverse PCR (Ochman et al., Methods Enzymol. 218:309-21 (1993)) was used to amplify, clone, and sequence DNA junctions where a given MdBV segment had integrated and joined with flanking *M. demolitor*, CiE1 or *P. includens* chromosomal DNA. On the basis of the integration assay data, nested inverse PCR primer sets for MdBV segments C and J (Table 3) were designed based on the domains identified as the site of integration into *M. demolitor*, CiE1 cells, or parasitized *P. includens*. 5 μg of *M. demolitor*, CiE1, or *P. includens* genomic DNA was digested with MfeI and XbaI for cloning right and left virus junctions of segment B from *M. demolitor*, CiE1 cells and *P. includens* for segment C, and PciI for the left junctions for segment J. Following phenol extraction and ethanol precipitation, precipitated DNAs were resuspended in 10 mM Tris-HCl pH 8.5, diluted to 2 ng/μl, and used for ligation reactions with T4 DNA ligase (Roche) at 10° C. overnight. After ligation, the T4 DNA ligase was heat inactivated at 65° C. for 10 minutes and 1 μl of the reaction mixture was used as template DNA for the first of three consecutive rounds of 50 μl standard PCR amplifications employing HotMaster Taq DNA Polymerase (5 Prime). After ligation, the T4 DNA ligase was heat-inactivated at 65° C. for 10 minutes and 1 μl of the reaction mixture was used as template DNA for the first of three consecutive rounds of 50 μl standard PCR amplifications employing HotMaster Taq DNA Polymerase (5 Prime) and 0.4 μM segment-specific primers (Table 3). Cycling conditions were as follows: initial denaturation at 94° C. for 2 minutes, followed by 35 cycles of denaturation at 94° C. for 20 seconds, annealing at 50° C. for 20 seconds and extension at 65° C. for 3 minutes. After the first round of amplification employing the outer primer set, 1 μl of the PCR reaction was used to set up a second round of amplification with the same primers. One μl from this reaction was then used for a third round of amplification with the nested primer pair. The resulting PCR products from the final amplification were cloned with the StrataClone PCR Cloning Kit (Agilent Technologies; Santa Clara, Calif.) and sequenced using M13 forward and reverse primers (Macrogen; Rockville, Md.). Sequences were analyzed using DNA Star (Madison, Wis.) and BLAST (NCBI).

TABLE 3

Primers used in inverse PCR reactions for MdBV genomic segments C and J.

| Primer Name | Primer Sequence | |
|---|---|---|
| SegJ-F1 (2330-2359) | TGCTACCCCT ATTGGATGAC TCACGAAAGA | SEQ ID NO: 74 |
| SegJ-R1 (2126-2101) | TGTAATCAAA GCAGGGCGCA TCAGGA | SEQ ID NO: 75 |
| SegJ-F2 (2506-2527) | GGGTGGCGTT CCTTCAGATG TG | SEQ ID NO: 76 |
| Seg.J-R2 (1226-1202) | AAATGGGCTT ACCGTGTTCG TGCTC | SEQ ID NO: 77 |
| Seg.J-F3 (3090-3113) | GTTCGACTCG TTAATTCAGC ACAC | SEQ ID NO: 78 |
| Seg.J-R3 (1279-1257) | TTTTTAGGCG TCATTTTCAT TGG | SEQ ID NO: 79 |
| Seg.J-F4 (4510-4531) | TGCGCCATGG GTTTCAAGTA TC | SEQ ID NO: 80 |
| Seg.J-R4 (3890-3872) | TTCGGGAGGT CGCCACAAG | SEQ ID NO: 81 |
| Seg.J-F5 (5073-5098) | TTTTGGGTGG GAGTGTTATG AATGTC | SEQ ID NO: 82 |
| Seg.J-R5 (3601-3573) | ATACTGCAAC CCGCTAATAA TAATAACTC | SEQ ID NO: 83 |
| Seg.C-F8 (1104-1129) | TGGGGCGCGG ATATCAATAG TAAGGA | SEQ ID NO: 84 |
| Seg.C-R8 (6563-6538) | TTTGCGCATG CGTAATTTGG TATCGT | SEQ ID NO: 85 |
| Seg.C-F9 (2251-2272) | ATTTTATACG CCGAACTCTT TG | SEQ ID NO: 86 |
| Seg.C-R9 (6510-6490) | GATCCGCGAT CATTTACCTT T | SEQ ID NO: 87 |
| Seg.C-F10 (3841-3870) | GAGCCATATT CGTGTGAGAG CATTAGTGTC | SEQ ID NO: 88 |

TABLE 3-continued

Primers used in inverse PCR reactions
for MdBV genomic segments C and J.

| Primer Name | Primer Sequence | |
|---|---|---|
| Seg.C-R10 (2867-2838) | TCTGGATGAT ATGATTCTGT TTGCGGTTTC | SEQ ID NO: 89 |
| Seg.C-F11 (4274-4294) | CAAGCATAGC CTTGCGGACA T | SEQ ID NO: 90 |
| Seg.C-R11 (2757-2735) | ACGAAATTTT CTGCCTGACG ACT | SEQ ID NO: 91 | qPCR and Southern Blotting.

To measure the copy number of MdBV segments C and J per infected CiE1 cell, total genomic DNA was isolated from $1 \times 10^6$ cells as described above followed by qPCR analysis using segment C (5'-TATGATGATTT GCCG-TAAGGGTAA-3' (SEQ ID NO:1) (forward) and 5'-AG-TAGGCCATGTGG TAAGCAGTAT-3' (SEQ ID NO:2) (reverse)) and J (5'CCAATTCGGAAGGGTCTCG-3' (SEQ ID NO:3) (forward) and 5'-GGGGTAGCACTTTTGTTTGT-TATCT-3' (SEQ ID NO:4) (reverse)) specific primers as previously described (Beck et al., Virology 359:179-89 (2007)). For Southern blotting, digoxigenin labeled probes corresponding to nt 4077-5866 on segment C and nt 5409-8215 on segment J were synthesized using digoxygenin-dUTP and the DIG High Prime DNA Labeling and Detection Start kit II (Roche). MdBV genomic DNA isolated from virions and CiE1 genomic DNA were digested with XbaI (segment C) or BspHI (segment J), followed by size fractionation on 0.8% agarose gels and transfer to nylon in 20×SSC. Blots were then prehybridized for 30 minutes at 40° C. in DIG Easy Hyb Buffer (Roche) followed by overnight hybridization at 40° C. with each probe (30 ng/ml). Blots were washed under high stringency (0.5×SSC, 0.1% SDS) at 65° C., followed by incubation with anti-digoxigenin antibody (Roche) (1:10,000) and visualization using the CSP-Star ready-to-use chemiluminescent substrate (Roche).

Results

MdBV Persists and Functionally Transforms CiE1 Cells.

Figure 1D:
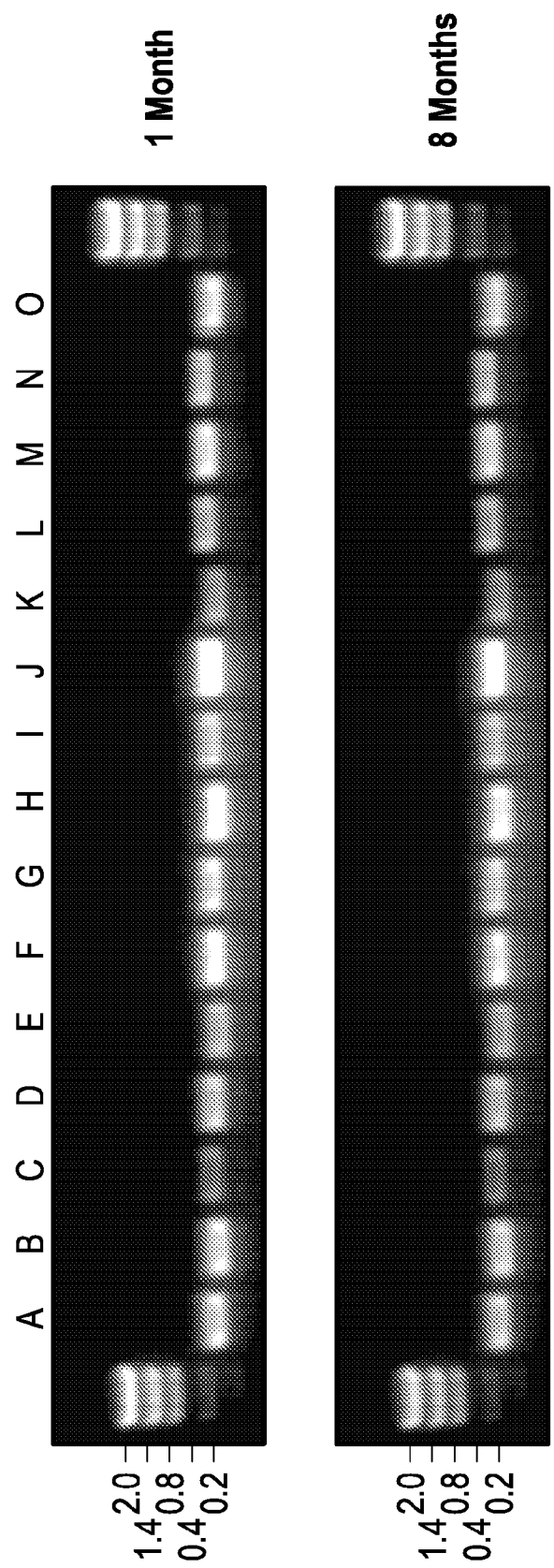
FIG. 1D shows an agarose gel of PCR products generated using DNA from infected CiE1 cells as template and primers specific for each MdBV genomic segment (A-O). The upper gel shows product produced from CiE1 cells 1 month post-infection while the lower gel shows products generated from CiE1 cells 8 months post-infection. Size markers (kb) are shown to the left.

A key function of PDVs in parasitism is to prevent the host's immune system from killing the offspring of parasitoids by a cellular defense response called encapsulation. MdBV disables encapsulation by preventing hemocytes called granulocytes and plasmatocytes from adhering to wasp offspring and causing some granulocytes to apoptose. Loss of adhesion is due primarily to expression of the glc genes in infected hemocytes, which encode very similar cell surface glycoproteins, while apoptosis is associated with expression of ptp-H2. MdBV infection blocks adhesion and causes some CiE1 cells to apoptose, while RNAi knockdown of Glc gene expression rescues adhesion. CiE1 cells were infected with MdBV at an multiplicity of infection (MOI) of 10, which resulted in most cells becoming non-adhesive and some cells apoptosing between 24 and 72 hours as previously reported (FIGS. 1A and 1B). However, apoptosis thereafter declined with surviving cells remaining non-adhesive but also proliferating at rates comparable to uninfected cells. These cells were maintained by passaging weekly. Cells remained non-adhesive after 1 month and 4 passages as well as after 8 months and 39 passages (FIG. 1C). PCR assays using DNA isolated from CiE1 cells as template and primers specific for each MdBV genomic segment further indicated that each persisted over the same period (FIG. 1D).

Multiple MdBV Genes are Persistently Expressed in CiE1 Cells.

Figures 1, 2A:
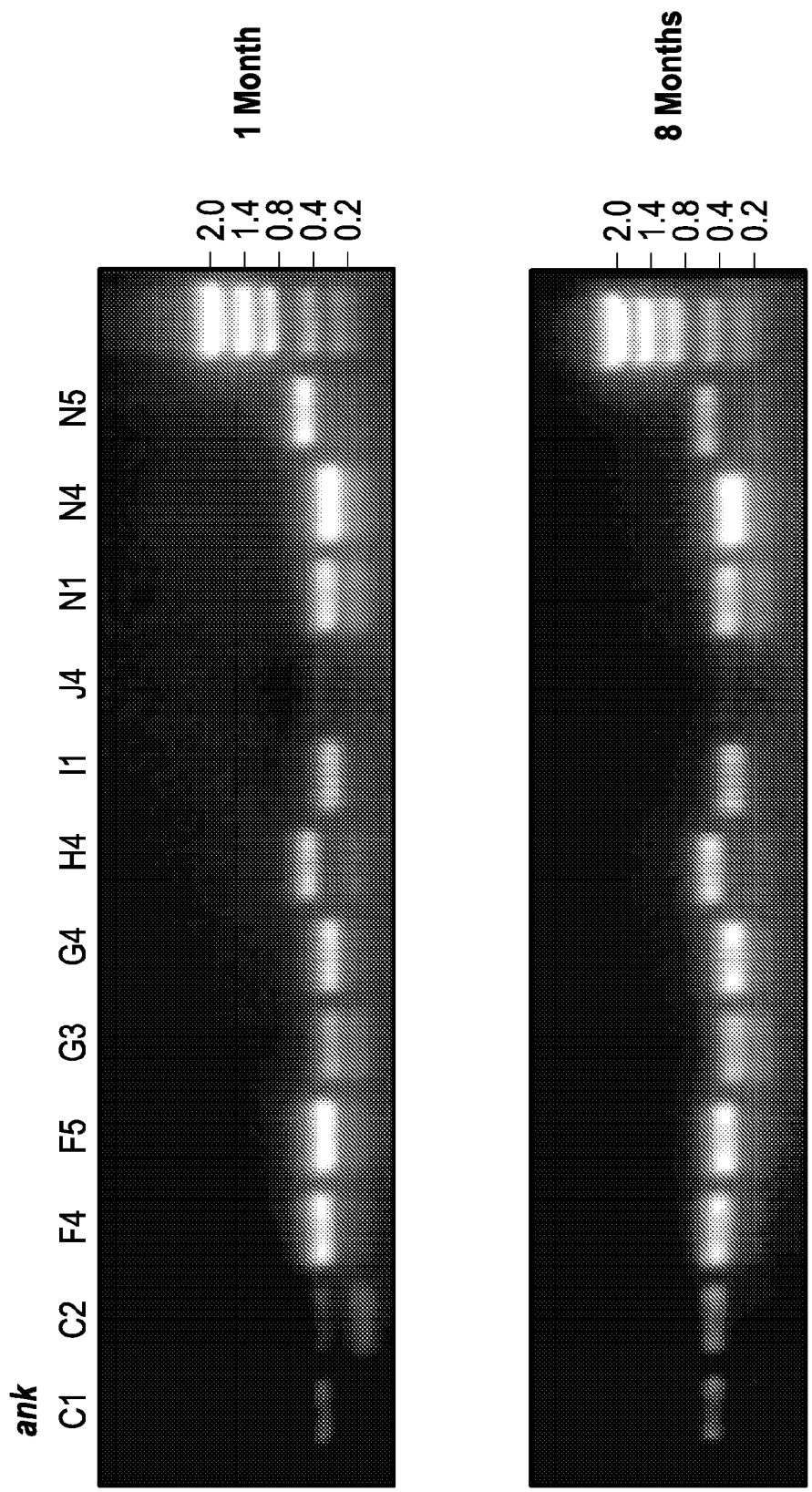
FIG. 1 shows that MdBV persists in and transforms CiE1 cells.
FIG. 2A shows an RT-PCR analysis of total RNA isolated from CiE1 cells 1 and 8 months post-infection. The RT-PCR analysis involved primers specific for selected ank and ptp gene family members. Primers that amplify both glc1.8/3.2 and egf1.0/1.5 were also used. Amplicons for most genes are detected at both 1 and 8 months post-infection. Size markers (kb) are indicated to the right or left of gels.
Figures 2, 2A:
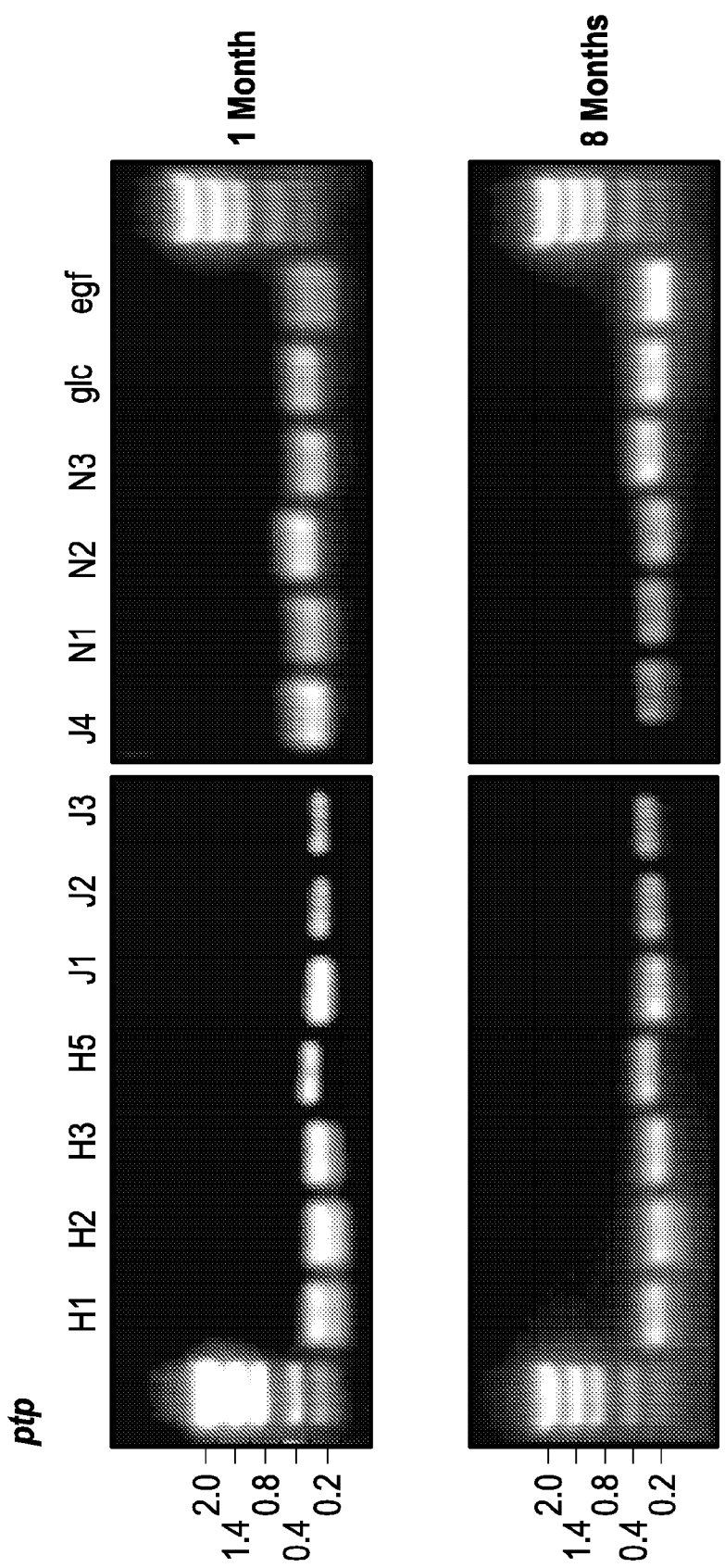
FIG. 2 shows MdBV transcripts are persistently detected in infected CiE1 cells.
Figure 2B:
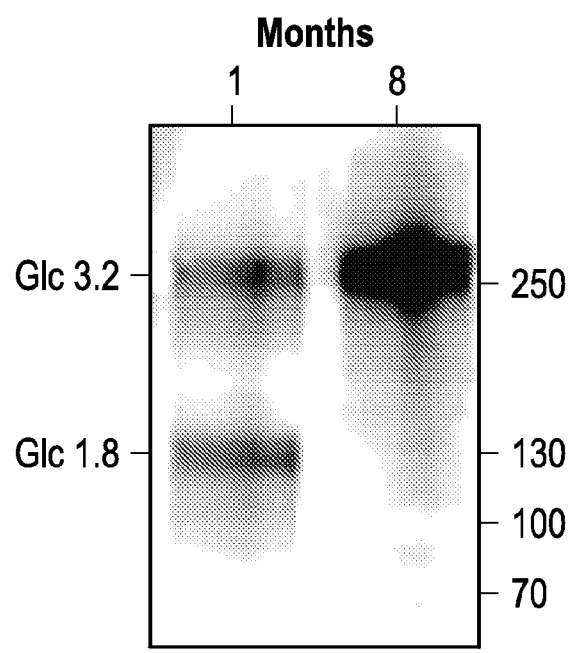
FIG. 2B shows an image of an immunoblot demonstrating the presence of Glc1.8 and 3.2 in CiE1 cell extracts 1 month post infection, and the presence of only Glc3.2 in cells at 8 months post-infection. Size markers (kDa) are indicated to the right.
Figure 2C:
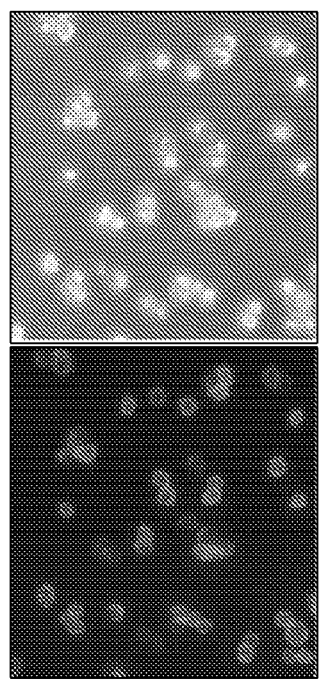
FIG. 2C shows a phase-contrast (upper) and epifluorescent micrograph (lower) of CiE1 cells 8 months post-infection labeled with anti-Glc1.8/3.2 and visualized using an Alexa 564 secondary antibody. Scale bar in the lower image equals 180 µm.

Transcriptome analysis previously showed that a majority of the MdBV ptp, ank, glc, and egf gene family members are expressed in P. includens hemocytes. Given that CiE1 cells were transformed from an adhesive to a non-adhesive state after infection and all MdBV genomic segments persisted, RT-PCR was used to determine whether persistent expression of MdBV genes also occurred. The results demonstrated that most viral gene family members expressed in P. includens hemocytes, including the glc genes responsible for adhesion loss, continued to be expressed in CiE1 cells after 1 and 8 months (FIG. 2A). In contrast, no amplicons for these gene products were detected in non-infected CiE1 cells. Immunoblot analysis using an anti-Glc1.8/3.2 antibody detected the presence of both Glc1.8 and 3.2 in cell extracts prepared at 1 month post-infection but only detected Glc3.2 at 8 months post-infection (FIG. 2B). Immunocytochemical analysis also showed that virtually all CiE1 cells at 8 months post infection expressed Glc3.2 on their surface (FIG. 2C).

MdBV Genomic Segments B, C, and J Persist in CiE1 Cells by Integrating.

Figure 3A:
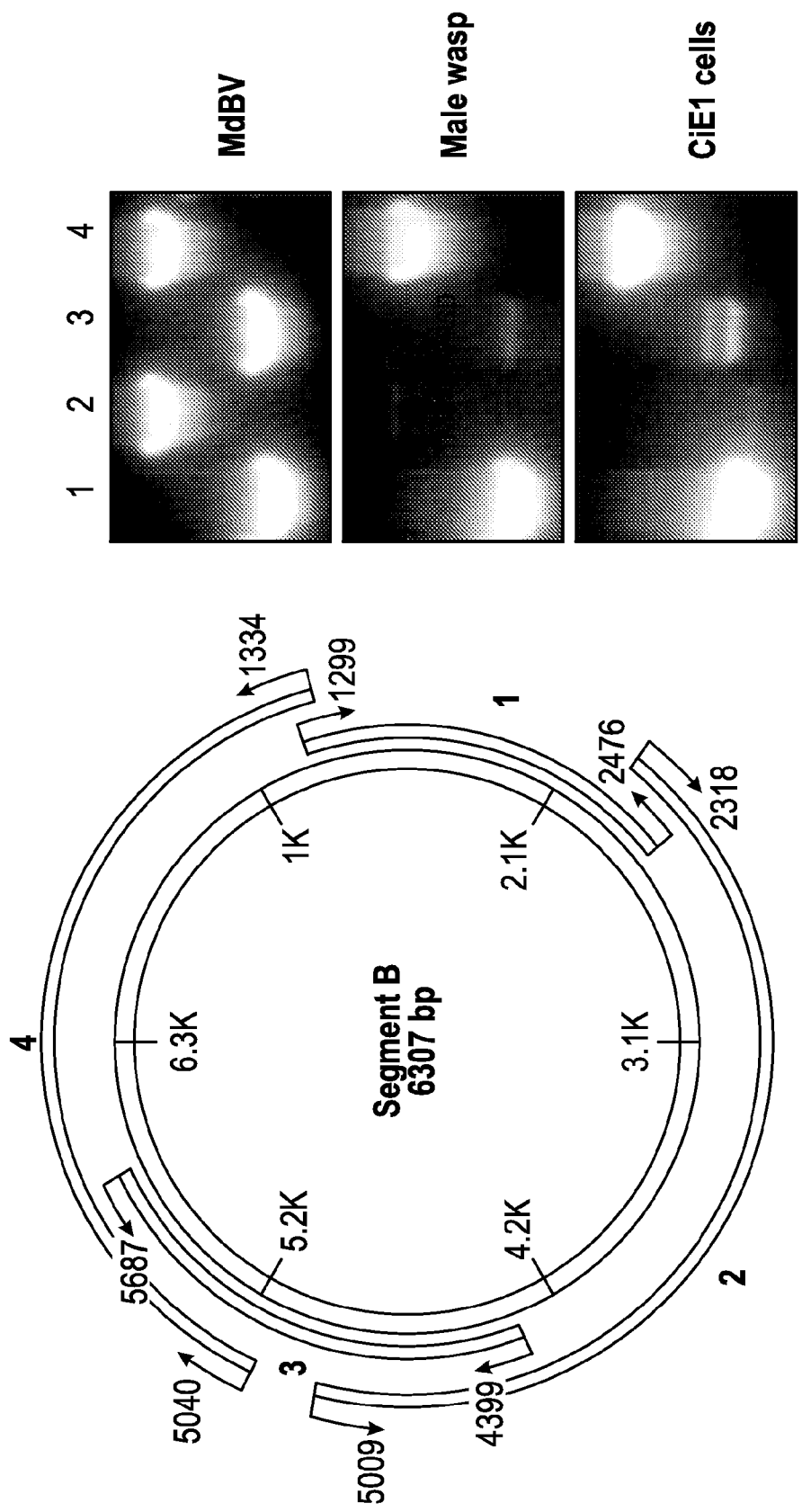
FIGS. 3A-3C show the design and outcome of PCR-based integration assays for segments B, C, and J respectively. Schematics to the left show each genomic segment with the inner circles indicating segment size (bp) and the outer bands indicating the location of primers used to amplify different domains of each segment. To the right of each schematic, the PCR products generated using the domain-specific primers and DNA from MdBV, adult male *M. demolitor*, or 21 day post-infection CiE1 cells are shown. Numbers above each lane correspond to the domains shown in each schematic.
Figure 3B:
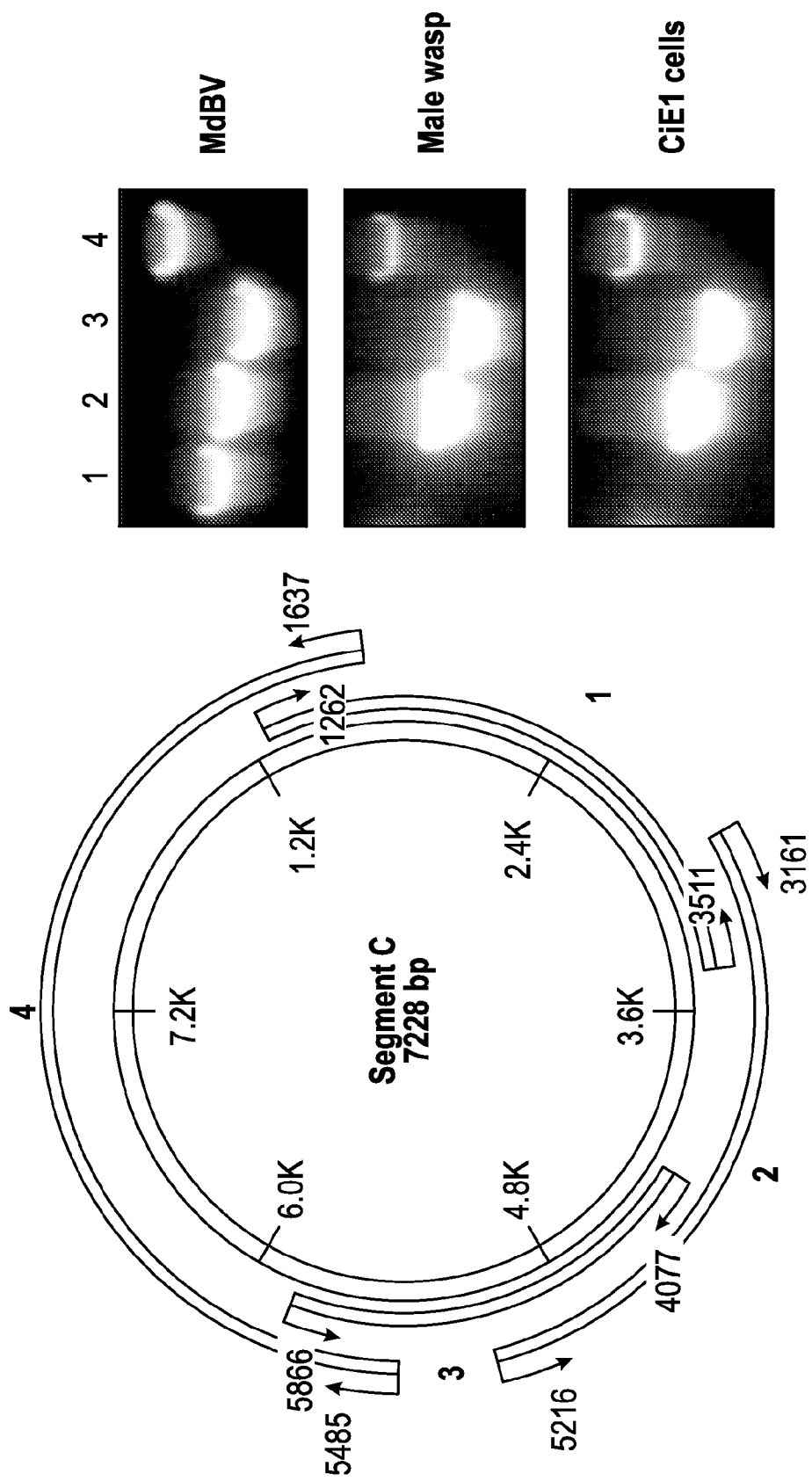
Figure 3C:
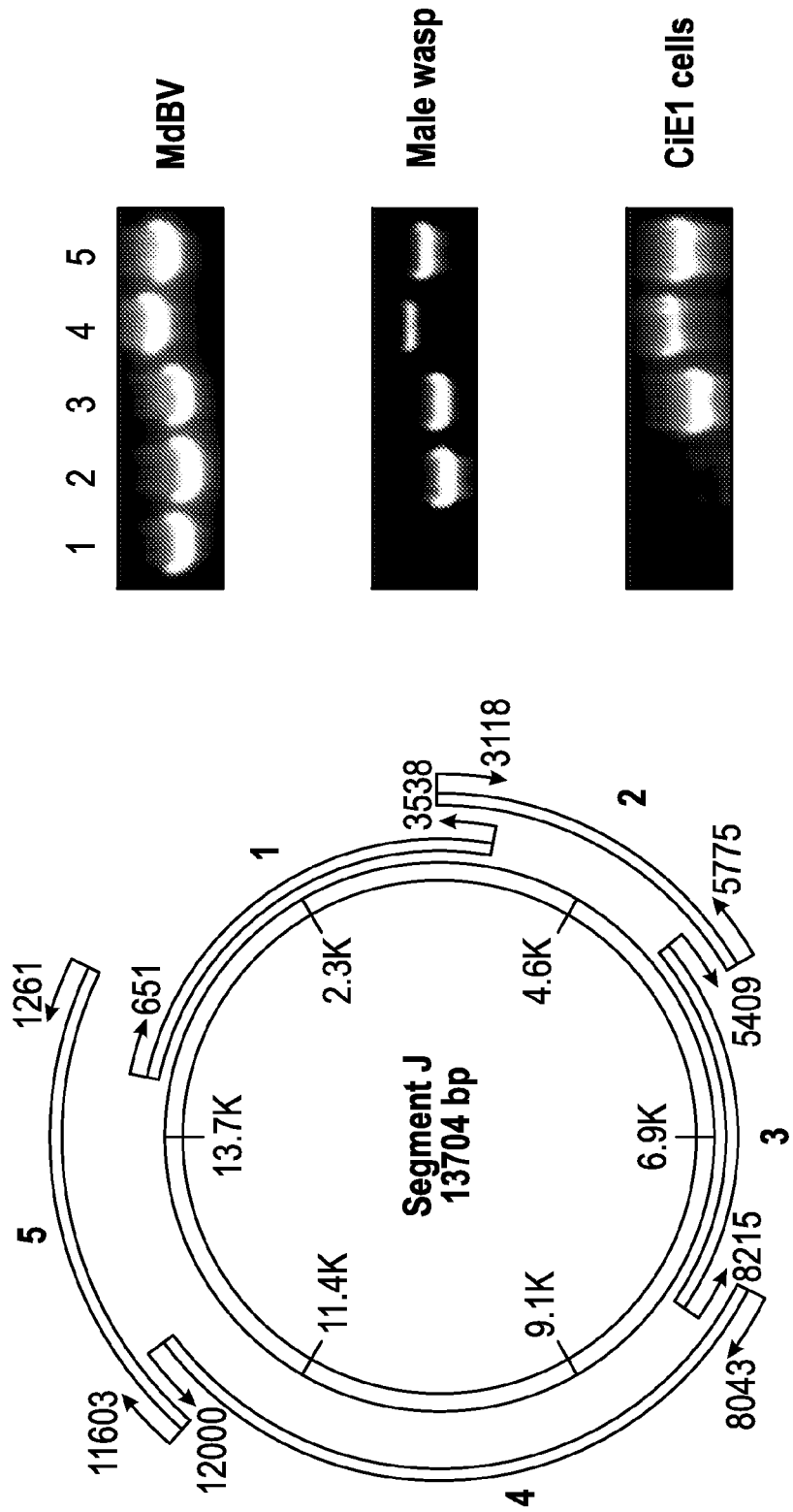

Since the encapsidated form of MdBV cannot replicate, whether MdBV genomic segments persisted in CiE1 cells as episomes or by integrating was sought to be determined. The most (J) and least (C) abundant segments as well as a segment of intermediate abundance (B) of the genome were selected for further study by designing overlapping primer pairs to amplify specific domains of each unless linearized and integrated (FIGS. 3A-3C). Amplification products were then compared using the following primers and templates: 1) episomal viral DNA isolated from virions, 2) genomic DNA from male M. demolitor wasps, which contain only the proviral (integrated) form of MdBV, and 3) genomic DNA from CiE1 cells infected 21 days earlier by MdBV. Each domain of segments B, C, and J was amplified using episomal viral DNA as template (FIGS. 3A-3C). In contrast, no amplicons were generated for domains 2 and 3 of segment B from male wasp DNA and MdBV-infected CiE1 DNA (FIG. 3A). For segment C, no amplicon was generated for domain 1 from male wasp and CiE1 DNA (FIG. 3B), while for segment J no amplicon was generated for domain 1 from male wasp DNA, and no amplicons were generated for domains 1 or 2 from CiE1 DNA (FIG. 3C). Identical results were generated using DNA isolated from CiE1 cells 8 months and 12 months post-infection. Taken together, these data showed that segments B, C, and J persisted in CiE1 cells by integrating within 21 days of infection, and that integration occurred in domains on each segment that also contained the site of integration of proviral segments B, C, and J in M. demolitor.

A Proviral Excision/Integration Motif Identifies the Site of Integration of MdBV Genomic DNAs into M. demolitor but not CiE1 Cells.

Figure 4A:
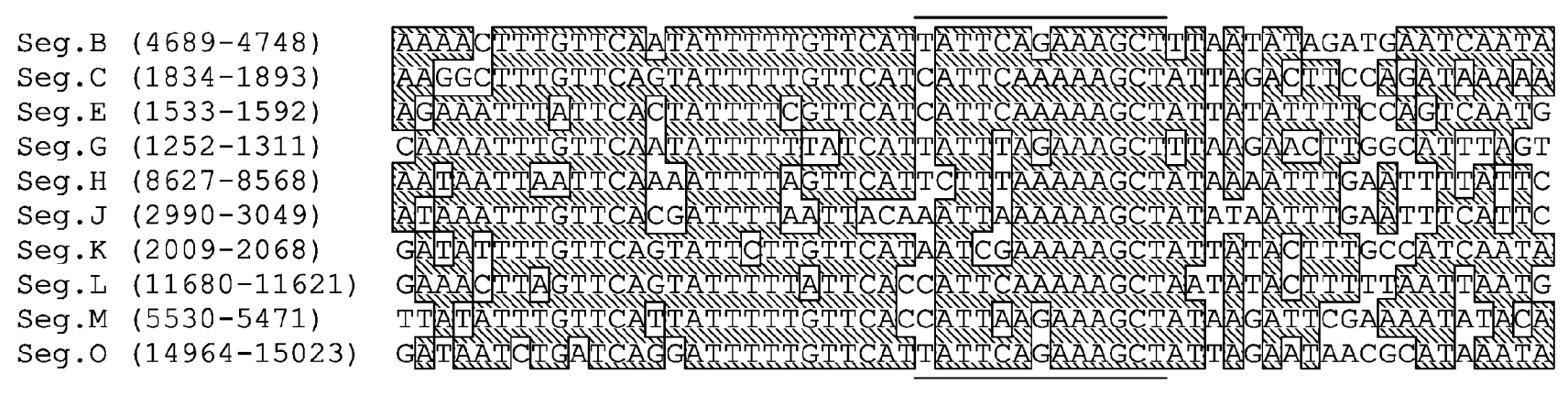

The tetramer AGCT embedded within a larger motif was previously identified as the site of excision for proviral genomic segments of GiBV and Glyptapanteles flavicoxis bracovirus (GfBV) from their associated wasps. Similar sequences have also been identified in some proviral genomic segments from Chelonus inanitus bracovirus (CiBV). Here, these domains are referred to as the predicted wasp excision/integration motif (WIM). Since all BVs evolved from a common ancestor, whether such motifs existed within the larger domains on MdBV segments B, C and J where integration into the genome of *M. demolitor* and CiE1 cells occurred was assessed. The analysis confirmed the presence of a predicted WIM in each of these genomic segments as well as in several others (FIG. 4A). Sequences to 36 nt upstream of the AGCT tetramer were AT rich and highly conserved among segments, whereas sequence conservation was weaker downstream of the AGCT tetramer (FIG. 4A).

Figure 4B:
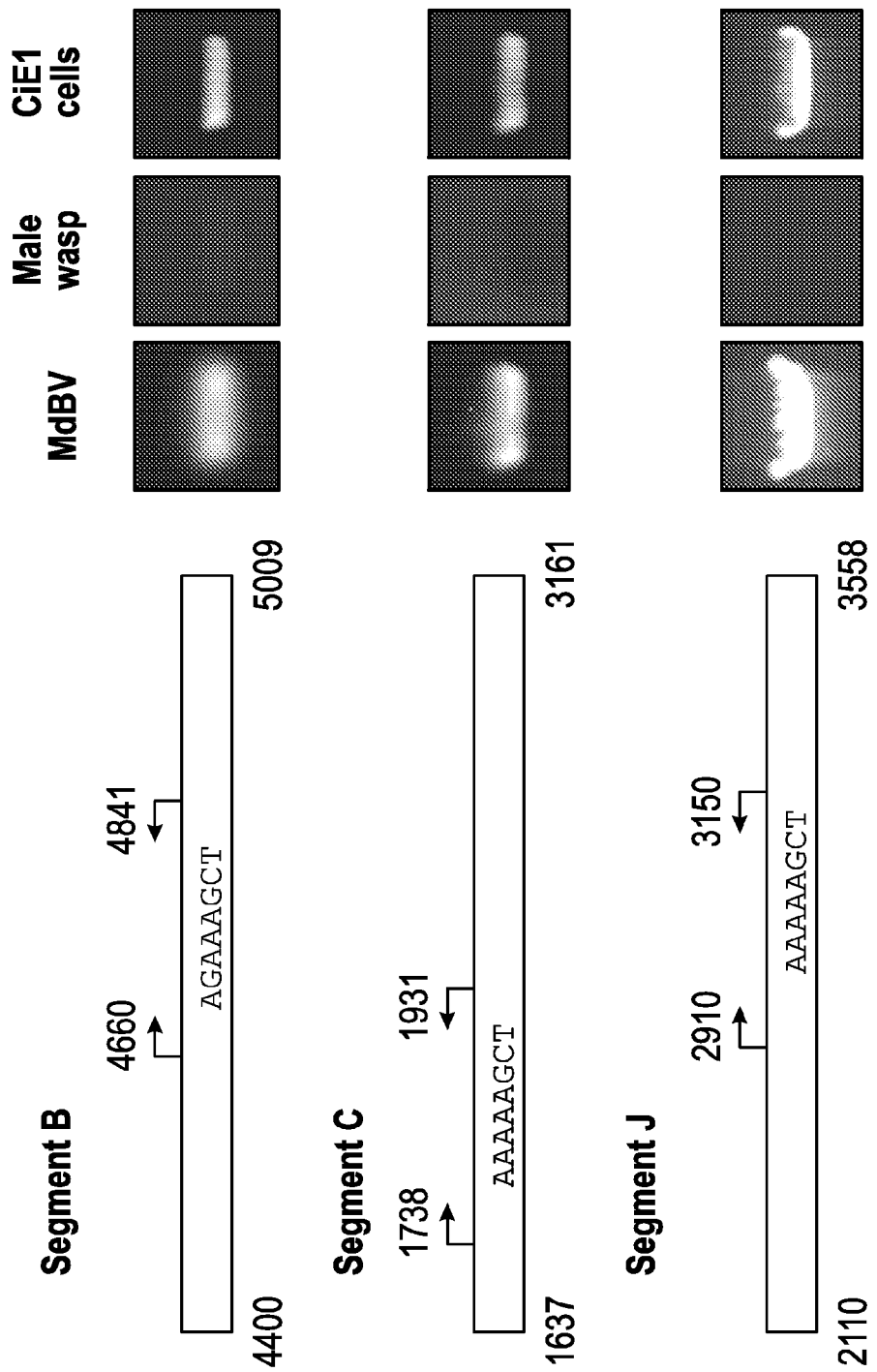
FIG. 4B shows the results of PCR-based integration assays. To the left are schematics showing larger domains on segments B, C, and J where the predicted WIM is located. Arrows and corresponding nucleotide (nt) (Seg. B; Seg. C; Seg. J) identify the location of flanking primers used in PCR-based integration assays. To the right of the schematic are images of gels showing the PCR products generated using these primers and DNA from MdBV, adult male *M. demolitor*, or CiE1 cells infected 21 days earlier with MdBV as template.

To assess whether these motifs identified the site of integration into *M. demolitor* and CiE1 cells, PCR-based integration assays were conducted using primers that flanked the WIMs on segments B, C, and J (FIG. 4B). In control assays, PCR products of expected size were amplified using episomal MdBV DNA as template (FIG. 4B). In the treatment assays, no products were generated from male wasp DNA, whereas products were generated for each segment using CiE1 cell DNA as template (FIG. 4B). Together, these data indicated the predicted WIM on these MdBV segments identified the site of integration in *M. demolitor* but did not identify the site of integration into host cells. To confirm that integration into *M. demolitor* corresponded precisely with the WIM, nested primers, MfeI, XbaI, or PciI-digested *M. demolitor* DNA, and inverse PCR were used to amplify, clone, and sequence wasp-proviral junction sequences for segments B and J. Sequencing of the clone MdB1R identified the right junction for proviral segment B (FIG. 4C). The AGCT tetramer identified the boundary for proviral segment B, which was then followed by 132 bp of *M. demolitor* genomic sequence (FIG. 4C). Reciprocally, sequencing of the clone MdJ1L identified the left junction for proviral segment J where the tetramer AATT (SEQ ID NO:45) formed the boundary followed by 426 base pairs of *M. demolitor* genomic sequence (FIG. 4C).

Sequencing of Host-Viral DNA Junctions Confirm that Segments J and C Integrate into CiE1 Cells and Parasitized *P. includens*

Figures 5B, 6A:
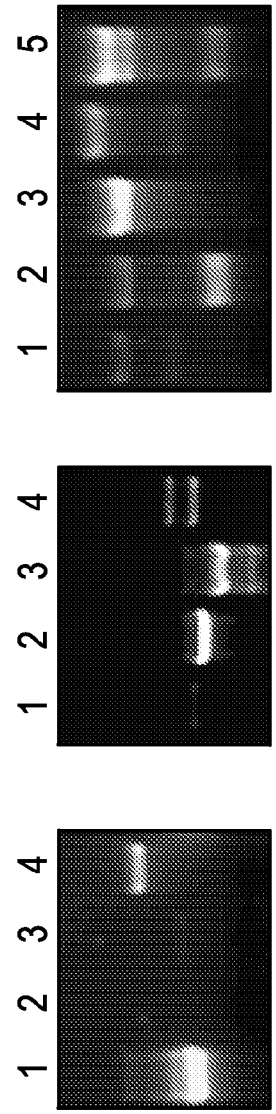
FIG. 5B shows a schematic illustrating the one right (CiC1R) segment C-CiE1 junction sequence (SEQ ID NO:22) cloned by inverse PCR. The schematic is organized as described in FIG. 5A. The CiE1 sequence for the clone is 990 bp.
FIG. 6A shows images of gels of PCR products amplified using domain specific primers for segments B, C, and J and hemocyte genomic DNA collected from parasitized *P. includens* larvae (day 7 post-parasitism). Domains correspond to the domains shown in FIG. 3.

To narrow the location on segments B, C and J where integration into CiE1 cells occurred, primer pairs within the domains identified in FIG. 3 were used and additional PCR-based integration assays were conducted. The results indicated that segment B integrated into CiE1 cells at a region between nucleotide (nt) 4440 and 4660, segment C integrated between nt 1931 and 3161, and segment J integrated between nt 3050 and 3558. These results were then used to design nested primer sets for use in inverse PCR reactions to clone and sequence CiE1-viral DNA junction sequences. Two left junction clones (COIL, CiJ2L) and one right junction clone (CiJ1R) were identified that corresponded to CiE1-segment J integration sequences (FIG. 5A). The boundaries of both left junction clones corresponded to nt 3262 on segment J and the tetramer ACCA, while the right boundary of the right junction clone corresponded to nt 3211 and the tetramer TAGT. These data also indicated that integration was associated with a ca. 50 bp deletion of segment J. BLAST analysis of the CiE1 flanking sequences for both the left and right junction clones revealed no significant homology with other sequences in current databases. One right junction clone (CiC1R) was also identified for a CiE1-segment C integration event (FIG. 5B). The boundary of this junction corresponded to nt 2673 on segment C and the tetramer TAGT, which was identical to the boundary identified for the right junction of segment J. CiE1 flanking sequences associated with segment C shared no homology with known sequences in current databases and also differed from the flanking sequences associated with integration of segment J.

Figure 6B:
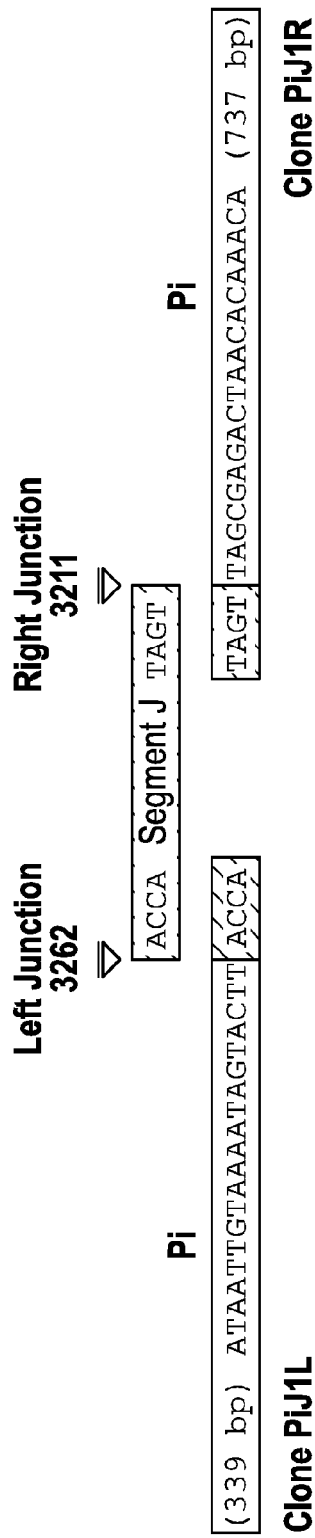
FIG. 6B shows a schematic illustrating the one left (PiJ1L) (SEQ ID NO:23) and one right (PiJ1R) (SEQ ID NO:24) segment J *P. includens* junction sequences cloned by inverse PCR. The schematic is organized as described in FIG. 5. The *P. includens* sequence for the left junction clone is 339 bp long while the *P. includens* sequence for the right junction clone is 737 bp.
Figure 6C:
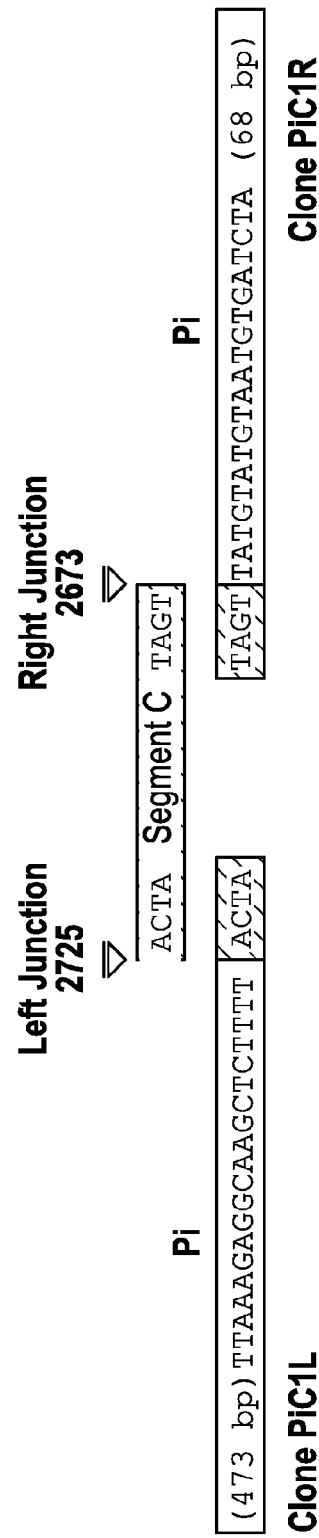
FIG. 6C shows a schematic illustrating the one left (PiC1L) (SEQ ID NO:25) and one right (PiC1R) (SEQ ID NO:26) segment C-*P. includens* junction sequences cloned by inverse PCR. The *P. includens* sequence for the left junction clone is 473 bp long while the *P. includens* sequence for the right junction clone is 68 bp.

Whether MdBV genomic segments integrated into naturally parasitized *P. includens* was assessed by first isolating genomic DNA from host hemocytes at day 7 post-parasitism and conducting PCR-based integration assays with segments B, C, and J as previously described for CiE1 cells. The results suggested that segments B and C had integrated due to the absence of amplicons for domains 2 and 3 with segment B and an absence of domain 1 for segment C (FIG. 6A). In contrast, detection of amplicons for each domain of segment J suggested that episomal DNA remained present (FIG. 6A). However, the reduced band intensity for domains 1 and 2 also suggested that some copies of J had potentially integrated (FIG. 6A). Additional assays conducted with segment B and DNA isolated from host hemocytes at earlier time points post parasitism suggested that integration had begun by 36 hours, as evidenced by reduced band intensities for domains 2 and 3. By 120 hours (5 days) post-infection, however, all copies of segment B appeared to be integrated as evidenced by a failure to amplify domains 2 and 3 as shown in FIG. 6A. Genomic DNA from whole host larvae was isolated at day 7 post-parasitism followed by cloning and sequencing of inverse PCR products under reaction conditions that were identical to those used with CiE1 cells. Note that no wasp offspring were present in these samples. One left (clones PiJ1L and PiC1L) and one right junction sequence (clones PiJ1R and PiC1R) were identified for both segment J and C (FIGS. 6B and 6C). As with CiE1 cells, the left and right boundaries for segment J corresponded to nt 3262 and 3211, while the left and right boundaries for segment C corresponded to nt 2725 and 2673. Host flanking sequence data also shared no homology with known sequences in databases.

Figure 7A:
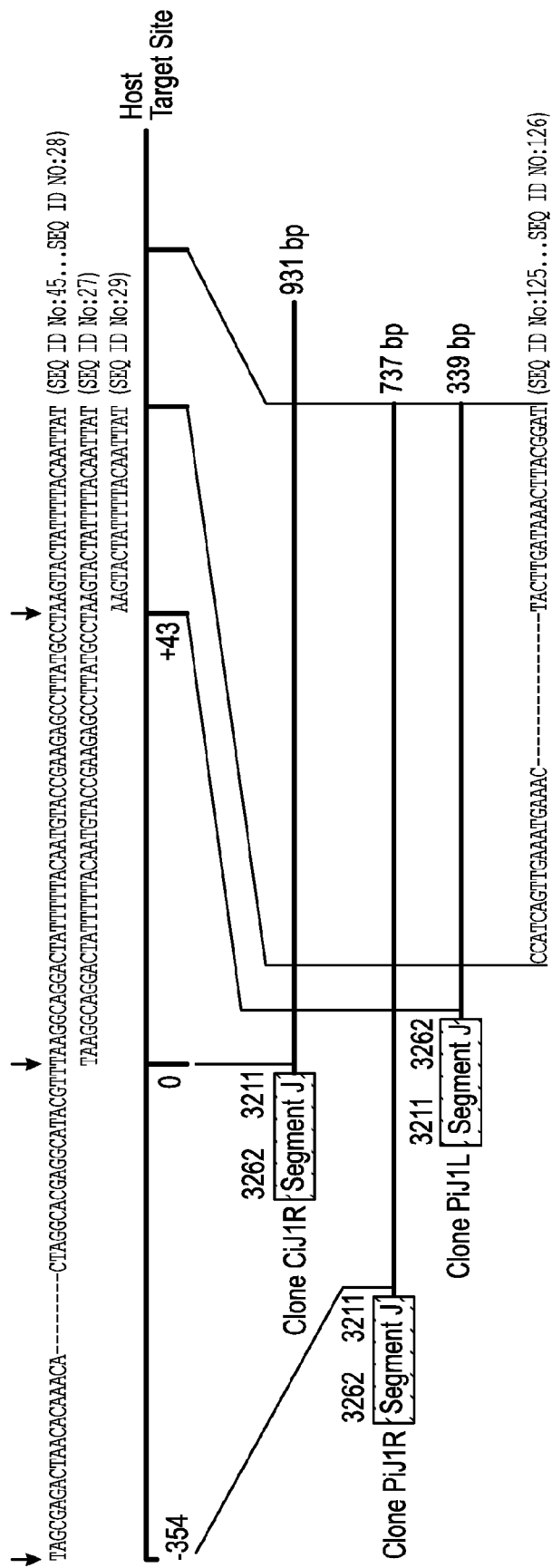
FIG. 7A shows a schematic demonstrating that segment J-host junction clones CiJ1R (931 bp), PiJ1R (737 bp), and PiJ1L (339 bp) integrate into the same target site in CiE1 cells and *P. includens*. Integration of segment J from Clone CiJ1R is shown at position 0 in the host target site. Segment J from Clone PiJ1R is inserted at position −354 while segment J from Clone PiJ1L is inserted at +43. Above each clone is shown the sequence of the deduced host target site with arrows indicating where each copy of segment J integrated. Below shows the region in each clone that was fully identical.
Figure 7B:
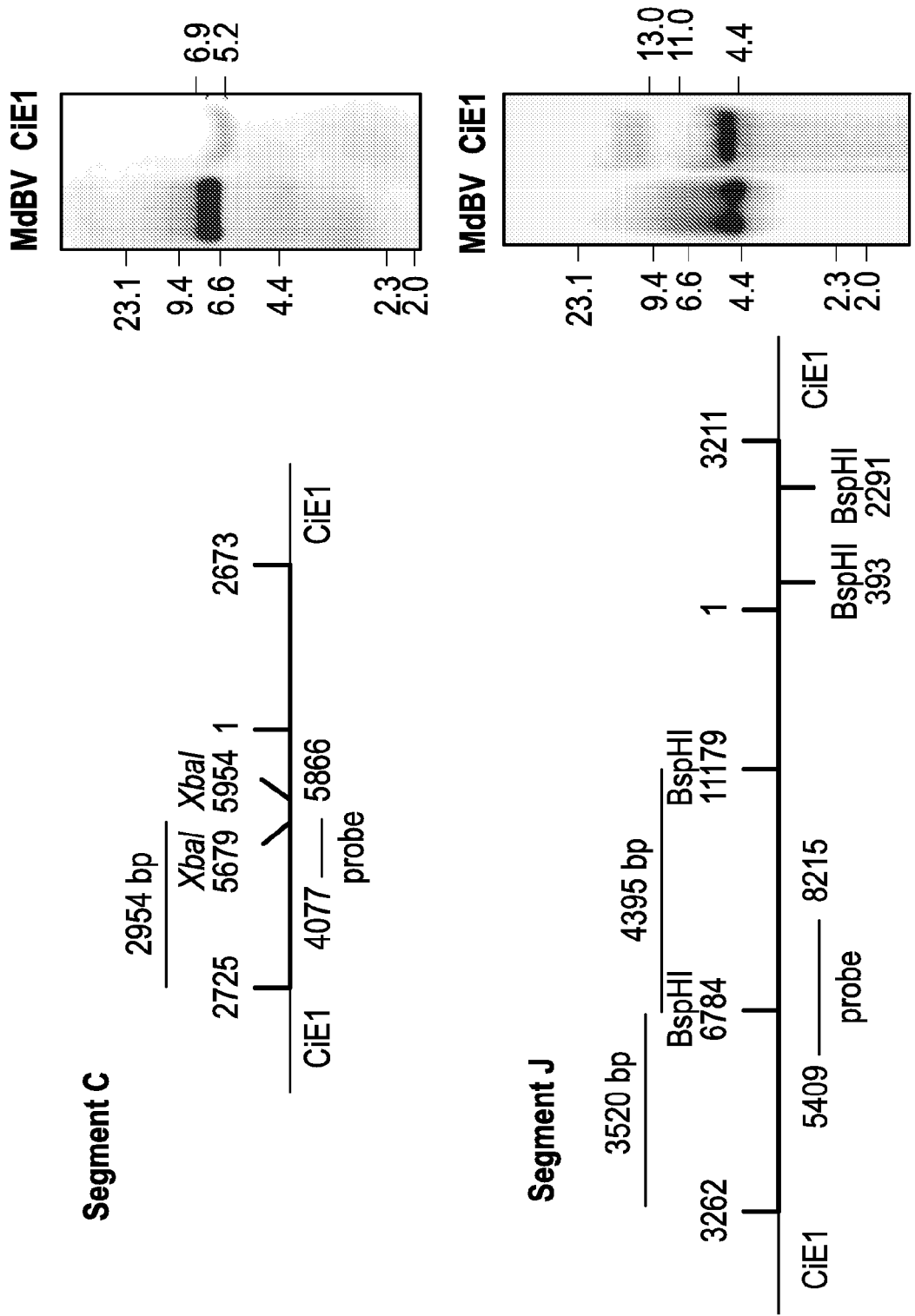
FIG. 7B shows Southern blot analysis of MdBV and CiE1 genomic DNA probed with a segment C (above) or segment J (below) specific probe. Schematics to the left show segments C and J integrated into CiE1 genomic DNA as determined by sequencing of junction clones (see FIGS. 5 and 6). XbaI (segment C) and BspH1 (segment J) sites are indicated, as is the site within each segment that corresponds to the synthesized probes. To the right shows Southern blots of XbaI digested MdBV and CiE1 genomic DNA hybridized with the segment C probe (above) or BspH1 digested MdBV and CiE1 genomic DNA hybridized with the segment J probe (below). Size markers (kb) are indicated to the left of each blot, while the estimated size (kb) of the fragments recognized by each probe are indicated to the right.

However, by comparing the cloned junctions for segment J to one another we determined that a portion of Clone CiJ1R from CiE1 cells was identical to clones PiJ1R, and PiJ1L from parasitized *P. includens*. These clones were aligned with one another in FIG. 7A, which shows that three copies of segment J integrated within a 1285 bp domain in the genome of CiE1 cells and parasitized *P. includens* that is identified as a putative host target site. By arbitrarily designating as position 0 the site of insertion for segment J in the right junction clone from CiE1 cells (CiJ1R), FIG. 7A shows that segment J for the right junction clone (PiJ1R) from *P. includens* was integrated 354 bp upstream, while segment J for the left junction clone (PiJ1L) from *P. includens* was integrated 43 bp downstream. FIG. 7A also shows that segment J was integrated in one orientation (flip) for the right junction clones from CiE1 cells and *P. includens*, but was integrated in the opposite orientation (flop) for the left junction clone from *P. includens*. The sequence of the presumptive host target site was assembled from the flanking sequence data of the three clones. The region overall exhibited a high A+T content (64%) and showed that each copy of segment J was inserted at sites identified by the sequence TA or TTA but shared no obvious homology with the boundary sequences for segment J (FIG. 7A). Examination of the host sequences for the two left junction clones (COIL and CiJ2L, see FIG. 5) for segment J from CiE1 cells indicated they shared no sequence homology with one another or the host target site shown in FIG. 7A. The host sequences from the two junction clones for segment C (PiC1L and PiC1R, FIG. 5) from *P. includens* also shared no homology with one another or the putative host target site for segment J.

To further characterize integration into CiE1 cells, qPCR assays were conducted to estimate the average copy number per cell for segments C and J and Southern blotting experiments were conducted to determine whether integration occurred in one or more locations in the genome. The qPCR results indicated that 1.03±0.13 SE copies of segment C were present on average per CiE1 cell at 8 months post-infection, while 21.03±0.1 copies of segment J were present. If these segments randomly integrated in the genome of CiE1 cells, a large number of bands or a smear on Southern blots would be expected. MdBV and CiE1 genomic DNA was digested with XbaI for which there are two predicted cut sites in segment C (FIG. 7B). In turn, the segment C probe generated should hybridize to a 6.9 kb fragment of segment C if not integrated, but should recognize a 2.95 kb region of segment C plus an unknown length of flanking CiE1 genomic DNA if integrated as shown in FIGS. 5 and 6. The results indicated this probe recognized the predicted 6.9 kb fragment of non-integrated segment C when hybridized to MdBV genomic DNA and a single 5.2 kb fragment when hybridized to CiE1 genomic DNA (FIG. 7B). CiE1 and MdBV genomic DNA was then digested with BspH1 for which there are four predicted cut sites in segment J (FIG. 7B). The segment J probe generated should hybridize to two 4.4 kb fragments of MdBV segment J if not integrated, but should recognize a 4.4 kb fragment and a 3.5 kb region of segment J plus an unknown length of flanking CiE1 genomic DNA. The results demonstrated that this probe recognized the predicted 4.4 kb fragment of non integrated segment J when hybridized to MdBV genomic DNA (FIG. 7B). When hybridized to CiE1 genomic DNA, the probe also recognized the predicted 4.4 kb fragment plus two other bands of approximately 13.0 and 11.0 kb (FIG. 7B).

MdBV Segments Share a Common Host Integration Motif.

The identical boundary sequences associated with segments J and C integration into host cells obviously suggested similarities in terms of where on each segment integration occurred. Indeed, the site of integration on each segment corresponded to a 110 or 111 nt domain consisting of two imperfect inverted repeats, which formed predicted stem-loop structures using Mfold 3.2 to optimize base pairing (FIG. 8A). Comparing these stem-loop structures to our junction sequence data further showed that the integration boundary for each segment corresponded with deletion of the 50 (segment J) or 51 nt loop (segment C). This deletion in turn resulted in the tetramers ACCA or ACTA forming the left border with the host genome and TAGT forming the right. Examination of other MdBV genomic segments revealed the presence of similar domains comprised of conserved inverted repeats and a more variable loop region (FIG. 8B). This domain was named the MdBV host integration motif (HIM). Consistent with the PCR based integration assay data (see FIG. 3), the HIM and WIM were located in close proximity (109-168 nt) to one another on segments B and J, as well as most other MdBV genomic DNAs (Table 4). However, these motifs were 770 and 836 nt apart respectively in segments C and G, while segment O contained two predicted WIMs that were separated by more than 7 kb from the predicted HIM (Table 4).

TABLE 4

Location of the predicted host integration motif to the predicted wasp excision/intergration motif on selected MdBV genomic segments.*

| Segment (size, nts) | Host integration Motif | Wasp excision/ integration motif | Proximity |
|---|---|---|---|
| B (6307) | 4586-4476 | 4699-4728 | 112 |
| C (7228) | 2644-2755 | 1844-1873 | 770 |
| E (8443) | 1323-1431 | 1543-157 | 111 |

TABLE 4-continued

Location of the predicted host integration motif to the predicted wasp excision/intergration motif on selected MdBV genomic segments.*

| Segment (size, nts) | Host integration Motif | Wasp excision/ integration motif | Proximity |
|---|---|---|---|
| G (10,790) | 2238-2128 | 1262-1291 | 836 |
| H (11,238) | 8284-8393 | 8562-8591 | 168 |
| J (13,704) | 3182-3291 | 3055-3026 | 126 |
| K (15,058) | 1909-1799 | 2019-2048 | 109 |
| L (15,096) | 11781-11891 | 11670-11641 | 110 |
| M (15,218) | 5697-5798 | 5520-5491 | 176 |
| O (34,334) | 22429-22540 | 14974-15003 | 7426 |
| | | 30126-30155 | 7568 |

*Positions of the host and wasp motifs on each segment correspond to sequences submitted to GenBank (see Materials and Methods for accession numbers).

MdBV Integrates into Non-Host Species.

MdBV infection usually results in the developmental arrest of *P. includens* larvae, which cannot pupate and ultimately die due to the expression of various MdBV gene products. To assess the fate of MdBV genomic DNAs in semi- and nonpermissive hosts, showing transient expression or absence of expression of viral gene products, respectively, cell lines from different species of insects including two lepidopterans that are semipermissive hosts (Sf21 cells from *Spodoptera frugiperda*, High Five cells from *Trichoplusia ni*), and two dipterans that are nonpermissive hosts (AaG2 cells from mosquito *Aedes aegypti* and mbn2 cells from *Drosophila melanogaster*) were tested. Conducting assays as outlined above, it was determined that most MdBV genomic DNAs stably integrated into each cell line except mbn2 cells where only 3 of the 15 genomic segments consistently integrated. Examination of segment J integrants in AaG2 cells by inverse PCR and sequencing showed that the insertion site junctions were identical to those characterized from CiE1 cells (FIG. 9). Because the *A. aegypti* genome is fully sequenced, although not well annotated, the site of integration for the inverse PCR products was identified as the 3' UTR of the steroid hormone receptor homolog gene AaHR3-1. Comparing the sequence of AaHR3-1 to the sequence obtained from the inverse PCR products, it was found that the insertion site junction shows an AT duplication immediately adjacent to the segment J inverted terminal repeats. In turn, segment J integration occurred at the stem of the palindrome (right junction ACCA, left junction TAGT with the intervening 50 bp loop being deleted just as found in CiE1 cells. Taken together, these results show that integration of MdBV genomic segments is not restricted to only insect species that are permissive hosts for *M. demolitor*. The results also suggest that the process of integration is similar among species given the features of the insertion site junctions between CiE1 cells, *P. includens* larvae and AaG2 cells.

Example 2

Viral and Wasp Genes with Potential Roles in Replication of *M. demolitor* and Integration in to Host Insects Materials and Methods Insects and Staging of Wasp Pupae.

Like most BV-carrying wasps, *M. demolitor* parasitizes the larval stage of certain species of Lepidoptera, including the moth *Pseudoplusia includens* (Strand M R, et al. 1988. Ann. Entomol. Soc. Am. 81:822-830). Both species were reared as previously described at 27° C. with a 16-h-light:

8-h-dark photoperiod (Strand M R, et al. 1991. J. Insect Physiol. 37:839-850). The different developmental stages of *M. demolitor* can be precisely monitored under these conditions using time and morphological characteristics (Strand M R, et al. 1988. Ann. Entomol. Soc. Am. 81:822-830). In brief, *M. demolitor* takes a total of 11 days to develop from an egg to an adult. After parasitism of a host larva, the *M. demolitor* egg hatches and the wasp larva feeds for 6 days. The last-stage wasp larva then emerges from the host's body on the morning of day 7, spins a silken cocoon around itself in 4 h, and pupates between 9 and 12 h postemergence. Newly pupated wasps (stage 1 pupae) are entirely white with light red compound eyes. On day 8, pupae enter stage 2, which is distinguished by wasps having dark red eyes, 3 or 4 black stripes on the dorsal side of the thorax, and a white abdomen. On day 9, stage 3 pupae have an entirely black thorax, black eyes, and a partially darkened abdomen, while on day 10, stage 4 pupae have a fully black thorax and abdomen with brown accents present on each leg. On day 11, pupae emerge from the cocoon as day 1 adults, which in the current study were thereafter fed ad libitum 10% sucrose in water and maintained at 18° C. in continuous dark. Females are easily distinguished from males as pupae and adults, because they have much shorter antennae.

PCR-Based Replication Assays and Transmission Electron Microscopy (TEM).

Figure 12:
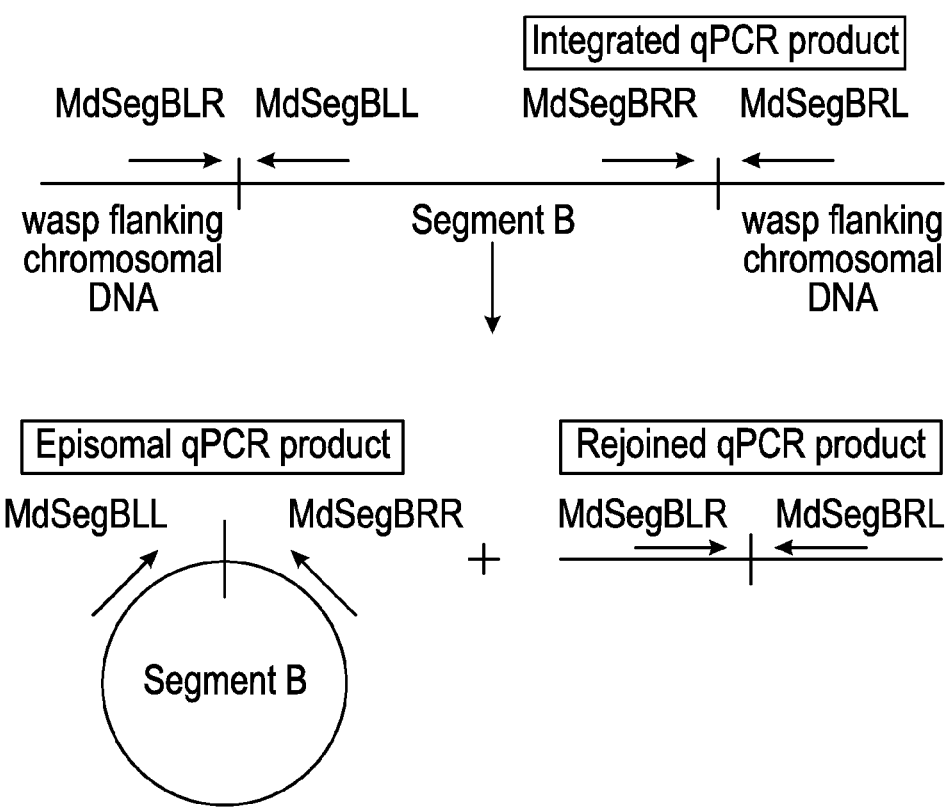
FIG. 12 is a diagram showing the qPCR primers and products used to differentiate between integrated, episomal, and rejoined DNAs from the *M. demolitor* encapsidated Segment B. The upper part of the panel shows Segment B integrated into the wasp chromosome. When excision occurs, Segment B circularizes, creating the episomal form of the segment. The DNA previously flanking the integrated form of Segment B is rejoined at the sites of Segment B excision.

Quantitative PCR (qPCR) and previously developed methods (Beck M H, et al. 2007. Virology 359:179-189) were used to determine the abundance of episomal MdBV segment B, integrated (proviral) segment B, and rejoined flanking DNA following segment B excision in ovaries from different wasp stages (FIG. 12). Briefly, ovaries from stage 1 to 4 female pupae and adult female wasps were prepared by homogenizing them in 1× DNase buffer (0.5 mM $CaCl_2$, 2.5 mM $MgCl_2$, 10 mM Tris-HCl, pH 7.5). Following filtration through a 0.45-μm filter, 1 μl of AMBION®TURBO DNase (Life Technologies, Grand Island, N.Y.) was added to some samples for 1 h at 37° C., while others were not DNase treated. After the addition of EDTA (10 mM) to inactivate the DNase, 25 μg of proteinase K (Roche, Basel, Switzerland) and 2% sarcosyl were added to samples, followed by incubation at 62° C. for 1 h and by phenolchloroform extraction and ethanol precipitation in the presence of 0.3M sodium acetate, pH 5.2. DNA pellets were resuspended in 30 μl of $H_2O$ and diluted 1:50 with water for use as the template.

After quantifying DNA concentrations, PCRs were run using a Bio-Rad thermocycler (Hercules, Calif.) and 25-μl reaction volumes containing DNA (10 ng) from day 5 adults as the template, DNA primers (6.25 pmol), and 1.25 units of HOTMASTER Taq polymerase (5 Prime, Gaithersburg, Md.) under the following cycling conditions: initial denaturation at 94° for 2 min, followed by 35 cycles of denaturation at 94° C. for 20 s, annealing for 20 s at the specified temperature for the primers used, and extension at 65° C. for 30 s with a final extension at 65° C. for 7 min. Primer sequences can be found in Table 7. Products were cloned into pSC-A-amp/kan (Stratagene, Santa Clara, Calif.) and propagated in *Escherichia coli*. Following overnight culture, plasmid DNA was then isolated using the FERMENTAS GENEJET plasmid miniprep kit (Thermo Scientific, Glen Burnie, Md.) and quantified, and their identity confirmed by sequencing. As a control, primers were also designed for *M. demolitor* elongation factor 1α (EF1α) (Table 7), which was similarly amplified and cloned, and its corresponding plasmid purified. Each of these plasmids was then used to make absolute standard curves to determine the abundance of integrated genomic DNA B, episomal genomic B, the empty B locus, and EF1α in ovary DNA. Ten microliter qPCR mixtures containing 1 μl of DNA template (wasp DNA or serially diluted amounts [$10^2$ to $10^7$ copies] of each plasmid standard) and specific primers were then run using a Rotor-Gene 3000 cycler (QIAGEN/Corbett, Valencia, Calif.) and previously described reaction conditions (Beck M H, et al. 2007. Virology 359:179-189). Melting curves of products were checked for amplification specificity, and threshold cycle (CT) values for each sample were fit to the standard curve generated from the plasmid DNA template dilutions. Per-ovary copy numbers were calculated by multiplying the qPCR estimate of copy number by the dilution factor and elution volume and dividing by the number of ovaries used in each sample. Two or 3 independently acquired biological replicates were performed for each wasp developmental stage with each sample internally replicated 4 times. For transmission electron microscopy (TEM), ovaries were collected, processed, and examined as previously described (Strand M R, et al. 1992. J. Gen. Virol. 73:1627-1635).

RNA Isolation, Library Preparation, and Transcriptome Sequencing.

Total RNA was isolated from 6 ovary samples collected from *M. demolitor* stage 1 pupae and day 1 adult females. Each ovary sample consisted of 15 to 20 ovary pairs with total RNA extracted using the Roche high pureRNA isolation kit followed by a second DNase treatment using AMBION® TURBO DNA-FREE reagents (Life Technologies, Grand Island, N.Y.). Sequencing libraries were prepared by the University of Georgia Genomics Facility using the ILLUMINA® TRUSEQ DNA sample preparation kit (Illumina, San Diego, Calif.) and the standard low-throughput protocol. RNA was fragmented thermally by ramping up to 94° C. followed by immediate cooling to 4° C. Each biological replicate was labeled with an individual indexed adapter. Libraries were then pooled to equal concentrations using quantitative PCR data and size selected by gel extraction for an average library size of 441 bp. Libraries were clustered on one lane at 6 μM followed by 100 cycles of paired-end sequencing on the ILLUMINA® HISEQ system (Illumina, San Diego, Calif.) housed at the HudsonAlpha Institute for Biotechnology (Huntsville, Ala.).

Sequence Read Processing, Assembly, and Analyses.

Sequence data were demultiplexed using CASAVA v1.8 software (Illumina, San Diego, Calif.). Reads were filtered for quality by removing those that had <90% of bases with >Q10 quality scores (based upon the ILLUMINA® TRUSEQ quality scoring system). High-quality reads were assembled using velvet v1.1.04 and Oases v0.2.21 (Zerbino D R, et al. 2008. Genome Res. 18:821-829), with k-mer length 51, and parameters cov_cutoff=3, min_trans-_length=200, ins_length=441. Sequence reads were mapped to transcripts using the Burrows-Wheeler Aligner bwa-sw algorithm and samtools (Li H, et al. 2009. Bioinformatics 25:1754-1760; Li H, et al. 2009. Bioinformatics 25:2078-2079). Use of the longer-read algorithm improved the percentage of mapped reads over short-read algorithms. If multiple matches were found for a single read, bwa-sw chose the reported mapping location at random. Counts of aligned reads could therefore be summed for all possible alternative transcripts of a single locus to give the raw number of reads mapping to a locus for each sample. Raw counts were converted to reads per kilobase per million reads mapped (RPKM) to normalize for average transcript length and the total number of reads for a sample (Mortazavi A, et al. 2008. Nat. Methods 5:621-628). Many loci had low RPKM values that did not allow meaningful statistical analyses for differences in expression. Loci with a cumulative RPKM value for all samples of <10 were considered unsuitable for further analyses due to their low transcriptional abundance and were removed from the data set. The difference between RPKM values for high-abundance loci in adult and pupal samples was tested by the t test function in R.

Some transcripts with homology to baculovirus or nudivirus genes (pif-1, p74, lef-8, HzNVorf9-1 and -2, and HzNVorf64) were fragmented in assembly into two or more different contigs, while others had frameshift mutations which suggested that they were inactivated. To assess whether these alterations reflected sequencing or assembly errors, we synthesized gene-specific primers that spanned an assembly gap or potential mutation site. Standard 25-μl reaction volumes containing DNA (10 ng) from stage 1 pupae and the appropriate primer pair were then run using a Bio-Rad thermocycler. Products diluted 1:2 in H$_2$O were sequenced by the Sanger method followed by assembly of the resulting sequence reads with DNASTAR SEQMAN software (DNASTAR, Madison, Wis.). Resequencing showed that each of these genes was intact in the *M. demolitor* genome. Thus, the fragmented transcript sequences were merged into one locus. Two ultra-high-abundance genes (vp39 and 17a) were fragmented during assembly due to excessive read coverage and were identified by reassembling 8.3% of all reads using the same assembly parameters described above.

Orthologous genes among the *M. demolitor* transcripts were identified by tblastn (orthologous protein candidates against translated transcripts) followed by reciprocal BLAST, using blastx to identify orthologs of translated transcripts in the NCBI nonredundant database of 3 Jun. 2011 (Altschul S F, et al. 1990. J. Mol. Biol. 215:403-410). Percent identity was calculated by tblastn alignment of the best query protein to the *M. demolitor* transcript. Coordinates for alignment boundaries of *M. demolitor* transcripts to protein orthologs to identify gene duplicates were gleaned from tblastn alignment results. The longest translated open reading frames (ORFs) were then aligned with orthologous protein-coding sequences from the NCBI protein database using Multiple Sequence Alignment (MUSCLE) (EMBL-EBI) (Edgar R C. 2004. Nucleic Acids Res. 32:1792-1797). Phylogenetic reconstruction of the evolution of these sequences was performed by maximum likelihood analysis using RAxML (Randomized Axelerated Maximum Likelihood) PROTCATLG (with the LG substitution matrix) and 1,000 bootstrap replicates, with the CIPRES online resource (Stamatakis A. 2006. Bioinformatics 22:2688-2690).

Nucleotide Sequence Accession Numbers.

A total of 66,425 transcripts were deposited in GenBank with accession numbers JO913492 through JO979916 and JR139425 through JR139430.

Results

MdBV replication begins in stage 2 pupae. BV replication in calyx cells of the wasp ovary consists of three major events: (i) amplification of viral DNA, (ii) virion formation and packaging of DNAs that have been excised and circularized from amplified segments, and (iii) lysis of calyx cells and accumulation of virions in the calyx lumen to form calyx fluid (Albrecht U, et al. 1994. J. Gen. Virol. 75:3353-3363; Annaheim M, et al. 2007. J. Gen. Virol. 88:450-457; Marti D, et al. 2003. J. Gen. Virol. 84:1141-1150; Savary S, et al. 1997. J. Gen. Virol. 78:3125-3134; Savary S, et al. 1999. Insect Mol. Biol. 8:319-327; Wyler T, et al. 2003. J. Gen. Virol. 84:1151-1163). The encapsidated genome of MdBV consists of 15 segments (A to O), which are individually packaged into virions that consist of a single nucleocapsid enveloped by a unit membrane (Beck M H, et al. 2007. Virology 359:179-189; Strand M R, et al. 1992. J. Gen. Virol. 73:1627-1635; Webb B A, et al. 2006. Virology 347:160-174). Prior results also report the complete sequence of each packaged segment and describe the wasp-viral boundary sequences for selected proviral segments including B (Beck M H, et al. 2007. Virology 359:179-189; Beck M H, et al. 2011. J. Virol. 85:11685-11696). Timing of MdBV proviral DNA amplification, segment excision/circulation, and packaging was thus characterized by conducting qPCR assays using genomic segment B as a marker (FIG. 12). The copy number of each product was determined in ovaries from stage 1 to 4 pupae and adults, while the copy number of EF1α served as a genetically unlinked control gene in the wasp genome.

Figure 11A:
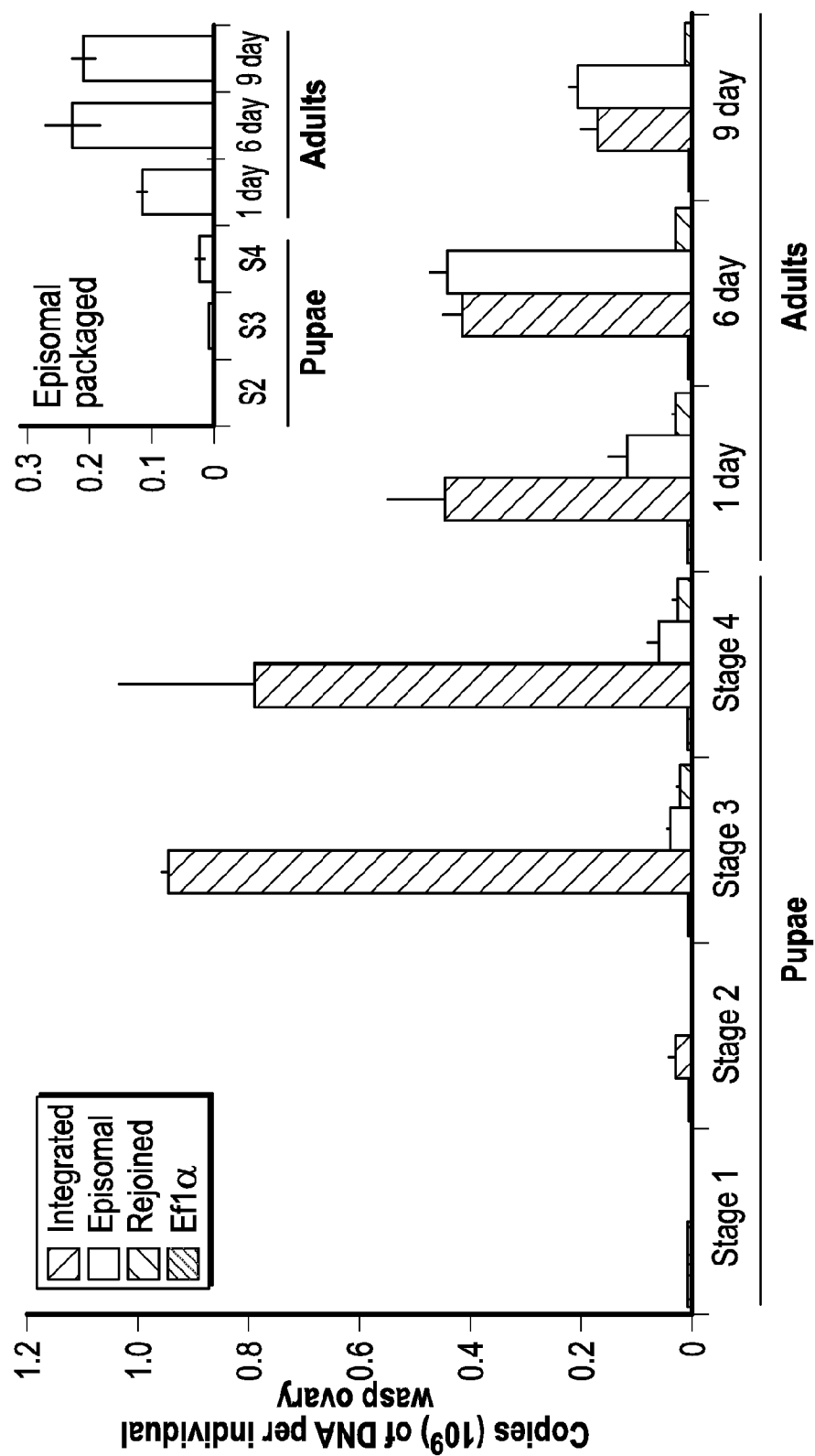
FIG. 11A is a bar graph showing mean copy number±standard error (SE) of qPCR products corresponding to integrated segment B (second bar), episomal segment B (third bar), the empty segment B locus (fourth bar), and EF1α (first bar). The total number of copies of each DNA in an individual wasp ovary is presented along the y axis, while the stages of wasp development are presented along the x axis. The inset shows mean copy number±SE of episomal segment B at each wasp stage that is packaged into virions. The data for each wasp stage derived from two or three independently collected ovary samples.
Figure 11B:
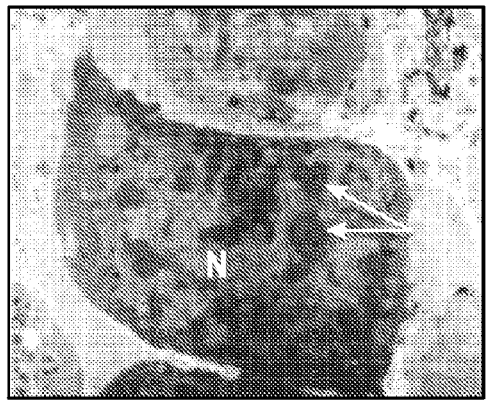
FIGS. 11B to 11E are TEM micrographs of MdBV nucleocapsids and virions during particular phases of replication.
Figure 11C:
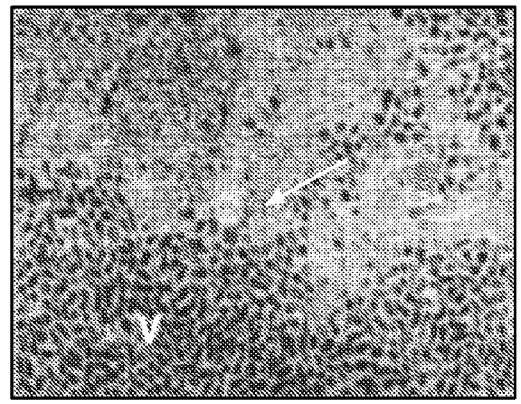
Figure 11D:
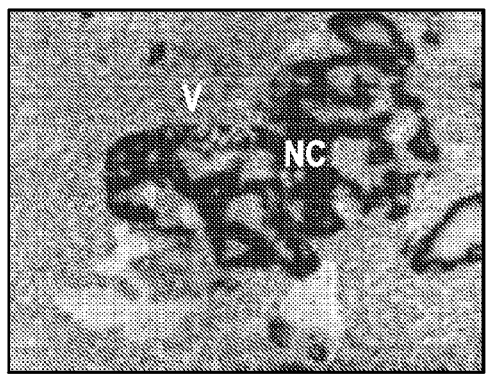
Figure 11E:
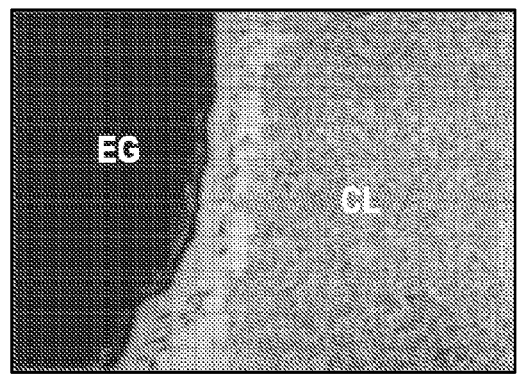

In stage 1 pupae, approximately equal copy numbers of integrated segment B and EF1α were detected, but no circularized segment B or empty B locus were detected (FIG. 11A). No circularized segment B or empty B locus was detected in stage 2 pupae, but the copy number of integrated segment B was nearly an order of magnitude higher than that of EF1α, indicating specific amplification of the number of DNA copies of the region of the genome containing segment B (FIG. 11A). The copy number of integrated segment B then dramatically increased in stage 3 pupae, which was followed by a progressive decline during subsequent stages of wasp development (FIG. 11A). Reciprocally, the abundance of episomal segment B began to rise in stage 3 pupae but did not reach a maximum until adult wasps were 6 days old (FIG. 11A). Products for the segment B "empty locus" (FIG. 11A, Rejoined) was first detected in stage 3 pupae, but its abundance did not change thereafter (FIG. 11A). Including a DNase step before isolating DNA from ovary homogenates (Beck M H, et al. 2007. Virology 359:179-189) further allowed determination of the copy number of episomal segment B in virions, which protect packaged DNAs from DNase degradation. Packaged episomal segment B was first detectable in stage 3 pupae and reached a maximum in 6-day-old adult wasps (FIG. 11A, inset). Comparison of these data to the total amount of episomal segment B indicated that less than half was packaged in ovaries from stage 3 and 4 pupae and day 6 adults. However, in day 9 adults, most copies of episomal segment B were packaged into virions.

qPCR data was linked to the timing of virion formation by conducting TEM studies. These observations showed that no capsids were visible in calyx cell nuclei from stage 1 and 2 pupae, whereas calyx cells from stage 3 pupae had enlarged nuclei that contained MdBV virions (FIG. 11B). At higher magnification, MdBV particles at different stages of assembly were readily visible within these calyx cells (FIG. 11C). In stage 4 pupae and day 1 adults, calyx cells were observed where MdBV particles were in the process of being assembled and also calyx cells that were in the process of lysing (FIG. 11D). Calyx cell lysis in turn resulted in the accumulation of a high density of virions in the calyx lumen (FIG. 11E). Overall, these data showed that amplification of DNA containing proviral segment B began in stage 2 pupae, while virion formation and packaging of episomal segment B began in stage 3 pupae. Replication then continued into adulthood.

Illumina Sequencing Generated a Rich Catalog of Transcripts for *M. demolitor* Ovaries.

The preceding results were used to select stage 1 pupae as a source of prereplication ovary RNAs and day 1 adults as a source of ovary RNAs during active MdBV replication.

While replication in stage 3 and 4 pupae was higher than that in day 1 adults, the latter was selected as a source of RNAs during active replication because replication remained high at this period and adults are easier to collect than pupae. 6 libraries were produced for each stage and sequenced in a single reaction using the ILLUMINA® HISEQ system (Illumina, San Diego, Calif.). The results yielded a total 371 million paired 100-bp reads, of which 330 million had an identifiable index tag. The number of reads in each index group ranged from 19 to 41 million. After quality filtering, 94 million read pairs and 33 million single-end reads remained, for a total of 222 million reads representing 22 Gb of sequence. From this data set, 197 million reads assembled into 32,711 loci that were 200 bp in length or greater. Alternative splicing was also predicted for 9,973 loci for a total of 66,425 transcripts. These were deposited in GEN-BANK with accession numbers JO913492 through JO979916 and JR139425 through JR139430. BLASTN identified 66 loci (0.2% of total) that corresponded to known intergenic regions or ORFs in MdBV genomic DNAs that are packaged into virions, many of which were misassembled.

Since mean RPKM values for these loci were much higher in adult than in pupal libraries, it was reasoned that most of these reads arose from low-level contamination by MdBV genomic segments that were massively amplified during replication and removed them from further analyses. However, recent results do indicate that some genes in the MdBV encapsidated genome are expressed in *M. demolitor* adults (Bitra K, et al. 2011. J. Gen. Virol. 92:2060-2071). While DNA contamination was not distinguish from transcripts in the data set, Bitra et al. (Bitra K, et al. 2011. J. Gen. Virol. 92:2060-2071) identified viral transcripts that potentially were not contaminants in this data set. In contrast, the low RPKM values for these loci in the stage 1 pupal samples argued that little or no contamination of the libraries by cellular genomic DNA occurred generally.

As the *M. demolitor* genome is not sequenced, the breadth of gene sampling in the transcriptional data set was evaluated by comparing it to the sequenced genomes of two other hymenopterans: *Nasonia vitripennis* and *Apis mellifera* (Honeybee Genome Sequencing Consortium. 2006. Nature 443:931-949; Werren J H, et al. 2010. Science 327:343-348). Orthologs between genome/transcriptome pairs were determined using BLAST, and shared genes as those with reciprocal hits between the data sets were counted. Using this method, the *N. vitripennis* and *A. mellifera* genomes shared 3531 of 9252 and 10560 genes respectively, while the *M. demolitor* data set shared 2428 orthologs with *N. vitripennis* and 2697 with *A. mellifera*. Assuming each species pairing shares the same number of genes (approximately 3,500), these data suggested that 69-77% of genes shared among species were present in the data set generated, and that a large percentage of genes in the *M. demolitor* genome were sequenced. This analysis also suggested that all of the highly expressed genes in ovaries were sampled, because random transcript sequencing results in highly expressed genes being sequenced more often by chance than genes expressed at low levels (Mortazavi A, et al. 2008. Nat. Methods 5:621-628).

*M. demolitor* Ovaries Express Several Nudivirus/Baculoviruslike Genes.

Given prior results with *C. congregate* and *C. inanitus* (Bézier A, et al. 2009. Science 323:926-930), the first priority was to screen the *M. demolitor* transcriptome for genes with similarity to known nudivirus and/or baculovirus genes. A total of 41 such transcripts were identified (partial list in Tables 5 and Table 6), whose known functions from studies of baculoviruses include RNA transcription, oral infectivity, and virion formation (Rohrmann G F. 2008. Baculovirus molecular biology. National Library of Medicine, National Center for Biotechnology Information, Bethesda, Md.). Of particular note was the presence of all 4 genes (p47, lef-4, lef-8, and lef-9) for the subunits of the unique RNA polymerase that baculoviruses and nudiviruses contain, and two genes similar to lef-5 and vlf-1, which regulate the hyperexpression of baculovirus very-late genes. Homologs were also identified of all six per os infectivity factors (i.e., pif genes p74, pif-1, pif-2, pif-3, 19K, odv-e56), which are envelope proteins, and odv-e66, which functions as both an envelope protein and hyaluronidase in baculoviruses that infect Lepidoptera (Rohrmann G F. 2008. Baculovirus molecular biology. National Library of Medicine, National Center for Biotechnology Information, Bethesda, Md.). Last, three genes were detected similar to vp39, vp91, and 38K, which together with vlf-1 encode capsid proteins conserved between nudiviruses and baculoviruses. Four other nucleocapsid proteins present in all baculovirus genomes (gp41, vp1054, p6.9, and odvec27) but unknown in nudiviruses were absent from the *M. demolitor* ovary transcriptome. However, homologs were identified of the predicted structural genes HzNVorf9, HzNVorf106, HzNVorf140, and PmV hypothetical protein, identified from *Helicoverpa zea* nudivirus 1 (Hz-1) (Cheng C H, et al. 2002. J. Virol. 76:9024-9034) and *Penaeus monodon* baculovirus (MBV), which is in actuality a nudivirus recently renamed *P. monodon* nudivirus (PmNV) (Jehle J A. 2010. Nudiviruses, p 153-170. In Asgari S, Johnson K N (ed), Insect virology. Caister Academic Press, Norwich, United Kingdom; Wang Y, et al. 2009. J. Invertebr. Pathol. 101:187-193). Homologs of these genes were also identified by proteomic analysis of CiBV particles from the wasp *Chelonus inanitus* (Wetterwald C, et al. 2010. J. Gen. Virol. 91:2610-2619).

Figure 13:
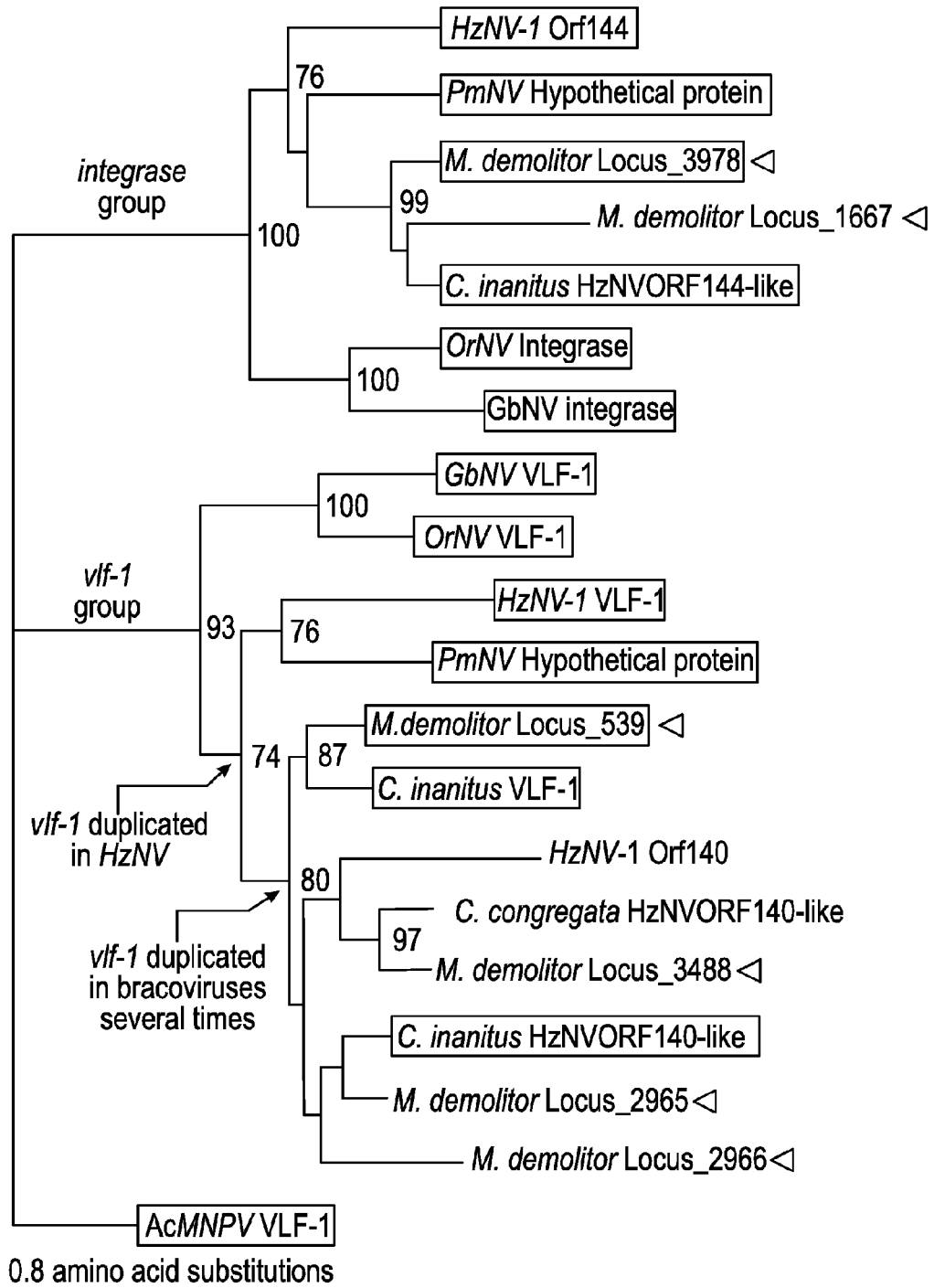
FIG. 13 is a maximum likelihood tree based upon the vlf-1, integrase (HzNVorf144), and HzNVorf140 genes in other BVs and nudiviruses. Genes within boxes have intact phage integrase (PF00589.16) domains. Numbers at nodes represent bootstrap replicates (nodes without bootstrap support >75 are not shown). The loci identified from the *M. demolitor* transcriptome are from this study and indicated with arrow head while orthologs from other BV-carrying wasps or nudiviruses are unmarked. Nudivirus taxa are *Heliothis zea* Nudivirus 1 (HzNV-1), *Gryllus bimaculatus* Nudivirus (GbNV), *Oryctes rhinocerus* Nudivirus (OrNV), *Penaeus monodon* Nudivirus (PmNV) and *Autographa californica* Multiple Nucleopolyhedrosis Virus (AcMNPV). HP from the baculovirus AcMNPV served as the outgroup.

Two other important features were noted about the data set in relation to nudiviruses and baculoviruses. First, with the exception of a nudivirus/baculovirus-like helicase and integrase (also known as HzNVorf144), other genes considered essential for DNA replication (Rohrmann GF. 2008. Baculovirus molecular biology. National Library of Medicine, National Center for Biotechnology Information, Bethesda, Md.) including a DNA polymerase (dnapol), DNA primases (lef-1, lef-2), DNA ligase, and the single-stranded binding (SSB) protein (lef-3) were absent from the *M. demolitor* transcriptome. Second, several nudivirus/baculovirus-like homologs (vlf-1, integrase, odv-e56, ac92, odv-e66, and HzNVorf9) were present in more than one contig and derive from duplicated genes (partial list in Tables 5 and 7). In most instances, 2 or 3 distinct gene duplicates were identified, but odv-e66 was represented in many different contigs (Table 7). Although they were fragmented during assembly, it was estimated that 8 or 9 paralogs of odv-e66 exist in the *M. demolitor* genome by counting the number of unique amino (9 peptide sequences) and carboxy (8 peptides) terminal ends present in the data set. 5 full-length transcripts were assembled (partial list in Tables 5 and 7). During the BLAST analyses, homology were noticed between vlf-1 and integrase (also known as vlf-1a and vlf-1b, respectively) and HzNVorf140 (Drezen J M, et al. 2012. Evolutionary progenitors of bracoviruses, p 15-32. In Beckage N E, Drezen, J-M (ed), Parasitoid viruses: symbionts and pathogens. Academic Press, London, United Kingdom). To examine the evolution of BV integrase and vlf-1 duplicates in relation to nudivirus/baculovirus homologs, a phylogenetic analysis of these genes was conducted to assess whether the homologs identified in *M. demolitor* more likely arose prior to or after acquisition by the wasp. These results strongly suggested that vlf-1 and integrase arose from an older duplication of vlf-1 in the nudivirus ancestor of BVs and that they have duplicated several times subsequently in *M. demolitor* (FIG. 13).

Sequence analysis further suggests that MdBV vlf-1 and integrase are functional enzymes with likely roles in regulating excision of MdBV proviral DNAs from the *M. demolitor* genome and/or integration of MdBV episomal genomic segments into host insects like *Pseudoplusia includens* and other arthropods.

TABLE 5

Nudivirus-like transcripts from female stage 1 pupae and day 1 adult *M. demolitor*[a]

| Gene name | Locus | Adult mean RPKM (n = 6) | Pupal mean RPKM (n = 6) | P value[b] | Putative functional role |
|---|---|---|---|---|---|
| helicase | 3891 | 29 | 0 | 1.1e−05 | DNA replication |
| integrase | 3978 | 53 | 1 | 1.9e−07 | DNA replication |
|  | 1667 | 48 | 0 | 6.7e−07 | DNA replication |
| p47 | 703 | 128 | 233 | 0.03 | RNA polymerase subunit |
| lef-4 | 2025 | 36 | 14 | 0.0002 | RNA polymerase subunit |
| lef-8 |  | 283 | 176 | NS | RNA polymerase subunit |
| lef-9 | 3218 | 72 | 54 | NS | RNA polymerase subunit |
| lef-5 | 539: transcripts 2, 7, 8, 9 | 159 | 231 | NS | Late gene expression |
| vlf-1 | 539: transcripts 1, 3, 4, 5, 6, 10 | 144 | 98 | NS | Late gene expression, capsid protein, DNA packaging |
| HzNVorf140 (vlf-1b) | 3488 | 88 | 0 | 6.4e−08 | Nucleocapsid protein, DNA packaging |
|  | 2966 | 197 | 0 | 1.9e−05 | Nucleocapsid protein, DNA packaging |
|  | 2965 | 519 | 0 | 2.2e−08 | Nucleocapsid protein, DNA packaging |
| 38K | 318 | 511 | 2 | 4.0e−05 | Nucleocapsid protein |
| vp91 | 4098 | 210 | 0 | 7.5e−08 | Nucleocapsid protein |
| vp39 |  | 4,109 | 3 | 6.2e−06 | Nucleocapsid protein |
| p74 |  | 1,320 | 2 | 1.1e−07 | Per os infectivity |
| pif-1 |  | 382 | 0 | 6.4e−09 | Per os infectivity |
| pif-2 | 226 | 448 | 0 | 9.4e−09 | Per os infectivity |
| pif-3 | 767 | 150 | 0 | 9.4e−08 | Per os infectivity |
| 19 kDa | 1791 | 597 | 2 | 1.7e−07 | Per os infectivity |
| odv-e56 | 13843 | 5 | 0 | 1.2e−08 | Per os infectivity |
|  | 1447 | 329 | 1 | 7.3e−06 | Per os infectivity |
|  | 1083 | 217 | 1 | 4.6e−07 | Per os infectivity |
| odv-e66 | 175 | 405 | 0 | 2.0e−09 | ODV envelope protein |
|  | 1139 | 91 | 0 | 4.7e−13 |  |
|  | 2331 | 197 | 0 | 3.1e−09 |  |
|  | 4186 | 207 | 0 | 1.0e−08 |  |
|  | 2730 | 244 | 0 | 1.0e−08 |  |
| HzNVorf9-1 |  | 864 | 2 | 1.0e−06 | Structural protein |
| HzNVorf9-2 |  | 761 | 0 | 1.7e−05 | Structural protein |
| HzNVorf106 | 332 | 508 | 1 | 8.2e−08 | Structural protein |
| PmV hypothetical protein | 756 | 546 | 0 | 1.5e−06 | Structural protein |
| ac92 5801 95 |  |  | 0 | 6.9e−08 | Structural protein |
|  | 2756 | 162 | 0 | 1.30e−08 | Sulfhydryl oxidase |
| HzNVorf64 |  | 1,043 | 12 | 7.9e−08 | Unknown |
| HzNVorf94 | 318 | 511 | 2 | 4.0e−05 | Unknown |
| HzNVorf128 | 1167 | 107 | 85 | NS | Unknown |

[a]Expression levels in pupae and adults are indicated by RPKM values (see Materials and Methods).
[b]NS, not significant.

TABLE 6

Similarity of MdBV transcripts to bracovirus, nudivirus and baculovirus genes

| Gene name | Protein domains (PFAM) | MdBV locus | HzNV-1 ORF name | HzNV-1 Identity* | Ci ortholog | Ci Identity* |
|---|---|---|---|---|---|---|
| integrase | Phage integrase (PF00589.16) | 3978 | 144 | 30% | CAR40240.1 | 53% |

*genes were fragmented in assembly

TABLE 7

Alignment of *M. demolitor* transcripts to orthologs shows that some genes have duplicated

| Gene name | MdBV locus | Alignment ortholog species | Alignment ortholog name | Alignment ortholog length (amino acids) | Alignment positions |
|---|---|---|---|---|---|
| integrase | 3978 | *C. inanitus* | CAR40240.1 | 228 | 1-215 |
| integrase | 1667 | *C. inanitus* | CAR40240.1 | 228 | 15-208 |

TABLE 7

Primers

| Gene | Primer name | Sequence 5'-3' | | Temp.* |
|---|---|---|---|---|
| | | Viral segment qPCR primers | | |
| | MdSegBRR | TTCTTAGCAG ATGATGTCAT CGC | SEQ ID NO: 92 | 55/65 |
| | MdSegBLL | CGTGGATTGA CAACGCGTTT | SEQ ID NO: 93 | 55/65 |
| | MdSegBRL | AGCTTATGTC GACAAGCGCT | SEQ ID NO: 94 | 55/65 |
| | MdSegBLR2 | TGATTAATTT GTGATACTTC CATGTT | SEQ ID NO: 95 | 55/65 |
| | PTP-J1F | CCAATTCGGA AGGGTCTCG | SEQ ID NO: 96 | 52/72 |
| | PTP-J1R | GGGGTAGCAC TTTTGTTTGT TATCT | SEQ ID NO: 97 | 52/72 |
| | | Gene specific qPCR primers | | |
| DNA pol δ | 4754_F | ATCGTCTACC CGACGTTCAC | SEQ ID NO: 98 | 55/65 |
| (Locus 4754) | 4754_R | GTGGGCTATG AACTGGTCGT | SEQ ID NO: 99 | 55/65 |
| DNA pol B2 | 4897_F | TATACTGCTC CGGGACTTGC | SEQ ID NO: 100 | 55/65 |
| (Locus 4897) | 4897_R | CAGCCCCGTA CAGATTGTTT | SEQ ID NO: 101 | 55/65 |
| helicase | helicaseF | TCTTCCAACA CACGATTCCA | SEQ ID NO: 102 | 55/65 |
| | helicaseR | AAGAACGCGT ACCACCAAAT | SEQ ID NO: 103 | 55/65 |
| lef-4 | lef4qPCRF | ACCCTTCACC AGGACAACTG | SEQ ID NO: 104 | 55/72 |
| | lef4qPCRR | AAATAGTACG CGCCACCTTG | SEQ ID NO: 105 | 55/72 |
| lef-9 | lef9qPCRF | CATCTTGATC AGCGTGCAAT | SEQ ID NO: 106 | 55/72 |
| | lef9qPCRR | ACGTCAGTAT TCCCCAGCAC | SEQ ID NO: 107 | 55/72 |
| p74 | p74F | TCGGTAATTG ATTGGGGAGA | SEQ ID NO: 108 | 55/72 |
| | p74R | TGCAGCACCA AACAAACAAT | SEQ ID NO: 109 | 55/72 |
| EF1-α | EF1aMdFqPCR | ATTGAAGGCC GAGCGTGAAC | SEQ ID NO: 110 | 52/72 |
| | EF1aMdRqPCR | CCGAGGGTGA AAGCAAGGAG | SEQ ID NO: 111 | 52/72 |
| | | Sequence correction primers | | |
| lef-8 | lef8span_F | CATGTGCTTT CCAATCATGC | SEQ ID NO: 112 | 55/65 |
| | lef8span_R | TTGACATTTT TGCTTTTGAA GG | SEQ ID NO: 113 | 55/65 |
| pif1 | pif1span_F | TGTGACCCAG CAGATAACGA | SEQ ID NO: 114 | 55/65 |
| | pif1span_R | TAATTGCCTT CTTGGGTTGG | SEQ ID NO: 115 | 55/65 |
| p47 | p47_F | TAAGAGCCGT GAATGGTGTG | SEQ ID NO: 116 | 55/65 |
| | p47_R | ATTTACGCCG GTGCATTACT | SEQ ID NO: 117 | 55/65 |
| 19kda | 19k_F | TCATATAATT TCCGACCGAC A | SEQ ID NO: 118 | 55/65 |
| | 19k_R | TCGGCTTGCA TTTAGACGTT | SEQ ID NO: 119 | 55/65 |
| p74 | p74span_F | TCAAAAGCAA TCATGAGTAT GACA | SEQ ID NO: 120 | 55/65 |
| | p74span_R | TCAGTAACGC GATGTTCAGG | SEQ ID NO: 121 | 55/65 |

TABLE 7-continued

Primers

| Gene | Primer name | Sequence 5'-3' | | Temp.* |
|---|---|---|---|---|
| HzNVorf9-1-like | orf9-1F<br>orf9-1R | AAAGCGGCGT TTGATAGAAA<br>TGCGATGCAT TCTCCTGTTA | SEQ ID NO: 122<br>SEQ ID NO: 123 | 55/65<br>55/65 |
| HzNVorf9-2-like | orf9-2F<br>orf9-2R | TGTTACGAAT GGCGACTGAA<br>TGGTGTATTC CGAATGTGTG A | SEQ ID NO: 124<br>SEQ ID NO: 15 | 55/65<br>55/65 |
| HzNVorf64 | orf64F<br>orf64R | ATCGCGACAA TACACCAACA<br>ACAAACCAAT GTGGGAAAAA | SEQ ID NO: 16<br>SEQ ID NO: 44 | 55/65<br>55/65 |

*Annealing/Extension temperature (° C.)

---

What is claimed is:

1. A method of integrating exogenous DNA into the genome of a cell thereby producing a genetically modified cell, comprising introducing a polydnavirus delivery construct comprising an exogenous nucleic acid to a target cell to form the genetically modified cell comprising the exogenous nucleic acid, wherein the polydnavirus delivery construct is derived from *Microplitis demolitor* bracovirus (MdBV).

2. The method of claim 1, further comprising introducing to the target cell an integrase or a nucleic acid encoding an integrase.

3. The method of claim 2, wherein the integrase is a proviral bracovirus integrase.

4. The method of claim 1, wherein the polydnavirus delivery construct is encapsidated with a polydnavirus virion, wherein the method comprises introducing the polydnavirus virion to the cell.

5. The method of claim 4, wherein the polydnavirus virion further comprises the nucleic acid encoding the integrase.

6. The method of claim 1, comprising introducing the polydnavirus delivery construct to the cell by transfection or electroporation.

7. The method of claim 1, wherein the polydnavirus comprises at least one host integration motif.

8. The method of claim 7, wherein the host integration motif is selected from the group consisting of SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, and SEQ ID NO:43.

9. The method of claim 7, wherein the host integration motif is comprised within an MdBV segment.

10. The method of claim 9, wherein the MdBV segment is selected from the group consisting of segment A, segment B, segment C, segment D, segment E, segment F, segment G, segment H, segment I, segment J, segment K, segment L, segment M, segment N, and segment O.

11. The method of claim 1, wherein the exogenous nucleic acid comprises a nucleotide sequence of about 50 to about 35,000 nucleotides.

12. The method of claim 11, wherein the nucleotide sequence is about 1,000 to about 20,000 nucleotides.

13. The method of claim 1, wherein the exogenous nucleic acid sequence encodes a recombinant polypeptide.

14. The method of claim 13, wherein the recombinant polypeptide comprises a detectable tag.

15. The method of claim 14, wherein the detectable tag is selected from the group consisting of a histidine tag, a FLAG tag, a GST tag, and a hemagglutinin tag.

* * * * *

SEQUENCE LISTING

<160> NUMBER OF SEQ ID NOS: 126

<210> SEQ ID NO 1
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1
tatgatgatt tgccgtaagg gtaa                                          24

<210> SEQ ID NO 2
<211> LENGTH: 24
<212> TYPE: DNA
<213> ORGANISM: Artificial Sequence
<220> FEATURE:
<223> OTHER INFORMATION: Synthetic Construct

<400> SEQUENCE: 2
agtaggccat gtggtaagca gtat                                          24

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct

<400> SEQUENCE: 3
ccaattcgga agggtctcg                                                19

<210> SEQ ID NO 4
<211> LENGTH: 25
<212> TYPE: DNA
<213> ORGANISM: Artificial Sequence
<220> FEATURE:
<223> OTHER INFORMATION: Synthetic Construct

<400> SEQUENCE: 4
ggggtagcac ttttgtttgt tatct                                         25

<210> SEQ ID NO 5
<211> LENGTH: 60
<212> TYPE: DNA
<213> ORGANISM: Artificial Sequence
<220> FEATURE:
<223> OTHER INFORMATION: Synthetic Construct

<400> SEQUENCE: 5
aaaactttgt tcaatatttt tgttcattat tcagaaagct ttaatataga tgaatcaata        60

<210> SEQ ID NO 6
<211> LENGTH: 60
<212> TYPE: DNA
<213> ORGANISM: Artificial Sequence
<220> FEATURE:
<223> OTHER INFORMATION: Synthetic Construct

<400> SEQUENCE: 6
aaggctttgt tcagtatttt tgttcatcat tcaaaaagct attagacttc cagataaaaa        60

<210> SEQ ID NO 7
<211> LENGTH: 60
<212> TYPE: DNA
<213> ORGANISM: Artificial Sequence
<220> FEATURE:
<223> OTHER INFORMATION: Synthetic Construct

<400> SEQUENCE: 7
agaaatttat tcactatttt cgttcatcat tcaaaaagct attatatttt ccagtcaatg        60

<210> SEQ ID NO 8
<211> LENGTH: 60
<212> TYPE: DNA
<213> ORGANISM: Artificial Sequence
<220> FEATURE:
<223> OTHER INFORMATION: Synthetic Construct

<400> SEQUENCE: 8
caaaatttgt tcaatatttt ttatcattat ttagaaagct ttaagaactt ggcatttagt        60

<210> SEQ ID NO 9
<211> LENGTH: 60
<212> TYPE: DNA
<213> ORGANISM: Artificial Sequence
<220> FEATURE:
<223> OTHER INFORMATION: Synthetic Construct

<400> SEQUENCE: 9
aataattaat tcaaaatttt agttcattct ttaaaaagct ataaaatttg aattttattc        60

<210> SEQ ID NO 10
<211> LENGTH: 60
<212> TYPE: DNA
<213> ORGANISM: Artificial Sequence
<220> FEATURE:
<223> OTHER INFORMATION: Synthetic Construct

<400> SEQUENCE: 10
ataaatttgt tcacgatttt aattacaaat taaaaaagct atataatttg aatttcattc        60

<210> SEQ ID NO 11
<211> LENGTH: 60
<212> TYPE: DNA
<213> ORGANISM: Artificial Sequence
<220> FEATURE:
<223> OTHER INFORMATION: Synthetic Construct

<400> SEQUENCE: 11
gatattttgt tcagtattct tgttcataat cgaaaaagct attatactttt gccatcaata        60

<210> SEQ ID NO 12
<211> LENGTH: 60
<212> TYPE: DNA

<213> ORGANISM: Artificial Sequence
<220> FEATURE:
<223> OTHER INFORMATION: Synthetic Construct

<400> SEQUENCE: 12
gaaacttagt tcagtatttt tattcaccat tcaaaaagct aatatacttt ttaattaatg    60

<210> SEQ ID NO 13
<211> LENGTH: 60
<212> TYPE: DNA
<213> ORGANISM: Artificial Sequence
<220> FEATURE:
<223> OTHER INFORMATION: Synthetic Construct

<400> SEQUENCE: 13
ttatatttgt tcattatttt tgttcaccat taagaaagct ataagattcg aaaatataca    60

<210> SEQ ID NO 14
<211> LENGTH: 60
<212> TYPE: DNA
<213> ORGANISM: Artificial Sequence
<220> FEATURE:
<223> OTHER INFORMATION: Synthetic Construct

<400> SEQUENCE: 14
gataatctga tcaggatttt tgttcattat tcagaaagct attagaataa cgcataaata    60

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct

<400> SEQUENCE: 15
tggtgtattc cgaatgtgtg a                                              21

<210> SEQ ID NO 16
<211> LENGTH: 20
<212> TYPE: DNA
<213> ORGANISM: Artificial Sequence
<220> FEATURE:
<223> OTHER INFORMATION: Synthetic Construct

<400> SEQUENCE: 16
atcgcgacaa tacaccaaca                                                20

<210> SEQ ID NO 17
<211> LENGTH: 60
<212> TYPE: DNA
<213> ORGANISM: Artificial Sequence
<220> FEATURE:
<223> OTHER INFORMATION: Synthetic Construct

<400> SEQUENCE: 17
aaaactttgt tcaatatttt tgttcattat tcagaaagct gtaagatttc acaagctgca    60

<210> SEQ ID NO 18
<211> LENGTH: 60
<212> TYPE: DNA
<213> ORGANISM: Artificial Sequence
<220> FEATURE:
<223> OTHER INFORMATION: Synthetic Construct

<400> SEQUENCE: 18
ttaataatat tatttttatca tactcgtaat taaaaaagct ataaatttg aatttcattc    60

```
<210> SEQ ID NO 19
<211> LENGTH: 24
<212> TYPE: DNA
<213> ORGANISM: Artificial Sequence
<220> FEATURE:
<223> OTHER INFORMATION: Synthetic Construct

<400> SEQUENCE: 19
ataccagtca aatatcatta acca                                              24

<210> SEQ ID NO 20
<211> LENGTH: 24
<212> TYPE: DNA
<213> ORGANISM: Artificial Sequence
<220> FEATURE:
<223> OTHER INFORMATION: Synthetic Construct

<400> SEQUENCE: 20
aaatctattt attaatatat acca                                              24

<210> SEQ ID NO 21
<211> LENGTH: 24
<212> TYPE: DNA
<213> ORGANISM: Artificial Sequence
<220> FEATURE:
<223> OTHER INFORMATION: Synthetic Construct

<400> SEQUENCE: 21
tagttaaggc aggactattt ttac                                              24

<210> SEQ ID NO 22
<211> LENGTH: 24
<212> TYPE: DNA
<213> ORGANISM: Artificial Sequence
<220> FEATURE:
<223> OTHER INFORMATION: Synthetic Construct

<400> SEQUENCE: 22
tagtaactgg acttttggg catt                                               24

<210> SEQ ID NO 23
<211> LENGTH: 24
<212> TYPE: DNA
<213> ORGANISM: Artificial Sequence
<220> FEATURE:
<223> OTHER INFORMATION: Synthetic Construct

<400> SEQUENCE: 23
ataattgtaa aatagtactt acca                                              24

<210> SEQ ID NO 24
<211> LENGTH: 24
<212> TYPE: DNA
<213> ORGANISM: Artificial Sequence
<220> FEATURE:
<223> OTHER INFORMATION: Synthetic Construct

<400> SEQUENCE: 24
tagttagcga gactaacaca aaca                                              24

<210> SEQ ID NO 25
<211> LENGTH: 24
<212> TYPE: DNA
<213> ORGANISM: Artificial Sequence
<220> FEATURE:
```

<223> OTHER INFORMATION: Synthetic Construct

<400> SEQUENCE: 25
ttaaagaggc aagctctttt acta    24

<210> SEQ ID NO 26
<211> LENGTH: 24
<212> TYPE: DNA
<213> ORGANISM: Artificial Sequence
<220> FEATURE:
<223> OTHER INFORMATION: Synthetic Construct

<400> SEQUENCE: 26
tagttatgta tgtaatgtga tcta    24

<210> SEQ ID NO 27
<211> LENGTH: 64
<212> TYPE: DNA
<213> ORGANISM: Artificial Sequence
<220> FEATURE:
<223> OTHER INFORMATION: Synthetic Construct

<400> SEQUENCE: 27
taaggcagga ctattttac aatgtaccga agagccttat gcctaagtac tattttacaa    60
ttat    64

<210> SEQ ID NO 28
<211> LENGTH: 84
<212> TYPE: DNA
<213> ORGANISM: Artificial Sequence
<220> FEATURE:
<223> OTHER INFORMATION: Synthetic Construct

<400> SEQUENCE: 28
ctaggcacga ggcatacgtt taaggcagga ctattttac aatgtaccga agagccttat    60
gcctaagtac tattttacaa ttat    84

<210> SEQ ID NO 29
<211> LENGTH: 20
<212> TYPE: DNA
<213> ORGANISM: Artificial Sequence
<220> FEATURE:
<223> OTHER INFORMATION: Synthetic Construct

<400> SEQUENCE: 29
aagtactatt ttacaattat    20

<210> SEQ ID NO 30
<211> LENGTH: 110
<212> TYPE: DNA
<213> ORGANISM: Artificial Sequence
<220> FEATURE:
<223> OTHER INFORMATION: Synthetic Construct

<400> SEQUENCE: 30
gaaaatttct tgatgggttg caatcctagt aaacgattct cagttttgta tgagatcccc    60
atacaaatta actaaggtcg accaggattg gactccatca agaaattgtc    110

<210> SEQ ID NO 31
<211> LENGTH: 112
<212> TYPE: DNA
<213> ORGANISM: Artificial Sequence
<220> FEATURE:
<223> OTHER INFORMATION: Synthetic Construct

```
<400> SEQUENCE: 31 gaaatttttcg acctgacgat cgcccctagt acgagccaga acagtttgtt cgaagattcc      60
atacattact tgttaaagcc tactaggcat agtcgtctag gcagaaaatt tc              112

<210> SEQ ID NO 32
<211> LENGTH: 111
<212> TYPE: DNA
<213> ORGANISM: Artificial Sequence
<220> FEATURE:
<223> OTHER INFORMATION: Synthetic Construct

<400> SEQUENCE: 32 gaaatttttcg acctgacgat cgcccctagt acgagccaga acagtttgtt cgaagattcc      60
atacattact tgttaaagcc tactaggcat agtcgtcagg cagaaaattt c               111

<210> SEQ ID NO 33
<211> LENGTH: 111
<212> TYPE: DNA
<213> ORGANISM: Artificial Sequence
<220> FEATURE:
<223> OTHER INFORMATION: Synthetic Construct

<400> SEQUENCE: 33 gaaatttttcg acttgacgaa cattactagt accctatagc tggaaatgta tgaagattcc      60
atacatatat tgtcaagccc tactaggaat ggttgccagg cagaaatttt c               111

<210> SEQ ID NO 34
<211> LENGTH: 111
<212> TYPE: DNA
<213> ORGANISM: Artificial Sequence
<220> FEATURE:
<223> OTHER INFORMATION: Synthetic Construct

<400> SEQUENCE: 34 gaaatttttct cgatcgcgac cctccctagt acggccaaga gcattttgtt cggagattcc      60
atacaaaatc tctcagtggc tactaggagc actcgtcatc gtgaaatttt c               111

<210> SEQ ID NO 35
<211> LENGTH: 111
<212> TYPE: DNA
<213> ORGANISM: Artificial Sequence
<220> FEATURE:
<223> OTHER INFORMATION: Synthetic Construct

<400> SEQUENCE: 35 gaaatttttct tgttgacgat cactcctagt acgtacttaa gcattttgta agaaaatccc      60
atactgaatt cagtttagtc gactagggat ggtcgtcatg tcgaaatttt c               111

<210> SEQ ID NO 36
<211> LENGTH: 111
<212> TYPE: DNA
<213> ORGANISM: Artificial Sequence
<220> FEATURE:
<223> OTHER INFORMATION: Synthetic Construct

<400> SEQUENCE: 36 gaaatttttcg taatgacgaa cgctcctagt agctgaagac agaaatcgta tgaagatttc      60
atacaaactt caaaaaacgg tactaggagt gatcgtgatt aagaaaattt c               111

<210> SEQ ID NO 37
```

```
<211> LENGTH: 110
<212> TYPE: DNA
<213> ORGANISM: Artificial Sequence
<220> FEATURE:
<223> OTHER INFORMATION: Synthetic Construct

<400> SEQUENCE: 37
gaaaatttct tgatgggttg caatcctagt aaacgattct cagttttgta tgagatcccc      60
atacaaatta actaaggtcg accaggattg gactccatca agaaattgtc               110

<210> SEQ ID NO 38
<211> LENGTH: 111
<212> TYPE: DNA
<213> ORGANISM: Artificial Sequence
<220> FEATURE:
<223> OTHER INFORMATION: Synthetic Construct

<400> SEQUENCE: 38
gaaaatttct tgatggaatg cgatcctagt cgaccgttgt caattttata cgagattttc      60
atacaaatgg actagggtcg accaggggtt ggacttcatc aagaaatttt c             111

<210> SEQ ID NO 39
<211> LENGTH: 111
<212> TYPE: DNA
<213> ORGANISM: Artificial Sequence
<220> FEATURE:
<223> OTHER INFORMATION: Synthetic Construct

<400> SEQUENCE: 39
gaaaatttca acatagcgat cgtccctagt acgaacttca catggctcta tacaaattgc      60
aaagcttttg ttaaaatact taccaggagt catttcttag tagaaatttt c             111

<210> SEQ ID NO 40
<211> LENGTH: 111
<212> TYPE: DNA
<213> ORGANISM: Artificial Sequence
<220> FEATURE:
<223> OTHER INFORMATION: Synthetic Construct

<400> SEQUENCE: 40
gaaaatttca gtttggagat cactactagt acgcaaaagc gcagtttcta tgaaaaactc      60
catactatcg ttaaaacccc caccaggaac acactctagg tcgaaaattt c             111

<210> SEQ ID NO 41
<211> LENGTH: 111
<212> TYPE: DNA
<213> ORGANISM: Artificial Sequence
<220> FEATURE:
<223> OTHER INFORMATION: Synthetic Construct

<400> SEQUENCE: 41
gaaaatttct tgctgacaat catacctagt gcgattatg atcatcagta tgaaacctcc       60
atacaatcgc tatctatgcc tactaggacg ggccttgtaa tcgaaaattt c             111

<210> SEQ ID NO 42
<211> LENGTH: 110
<212> TYPE: DNA
<213> ORGANISM: Artificial Sequence
<220> FEATURE:
<223> OTHER INFORMATION: Synthetic Construct

<400> SEQUENCE: 42
gaaattttct actaggcaat cgtccctagt cgtatcaaac acagattcta tggagatatc      60
```
aaacaaaatc gagagagcct actagcaatg cacttcaaaa agaaattttc         110

<210> SEQ ID NO 43
<211> LENGTH: 111
<212> TYPE: DNA
<213> ORGANISM: Artificial Sequence
<220> FEATURE:
<223> OTHER INFORMATION: Synthetic Construct

<400> SEQUENCE: 43
gaaattttcc ggttggcaaa cactactagt aggagtttgc cgaagttcta tgtatttgt   60 atcggatttt gaatgatgcc tacttggaac gtttgttatc aggaaatttt c          111

<210> SEQ ID NO 44
<211> LENGTH: 20
<212> TYPE: DNA
<213> ORGANISM: Artificial Sequence
<220> FEATURE:
<223> OTHER INFORMATION: Synthetic Construct

<400> SEQUENCE: 44
acaaaccaat gtgggaaaaa                                              20

<210> SEQ ID NO 45
<211> LENGTH: 20
<212> TYPE: DNA
<213> ORGANISM: Artificial Sequence
<220> FEATURE:
<223> OTHER INFORMATION: Synthetic Construct

<400> SEQUENCE: 45
tagcgagact aacacaaaca                                              20

<210> SEQ ID NO 46
<211> LENGTH: 10
<212> TYPE: DNA
<213> ORGANISM: Artificial Sequence
<220> FEATURE:
<223> OTHER INFORMATION: Synthetic Construct

<400> SEQUENCE: 46
gttaatacca                                                         10

<210> SEQ ID NO 47
<211> LENGTH: 10
<212> TYPE: DNA
<213> ORGANISM: Artificial Sequence
<220> FEATURE:
<223> OTHER INFORMATION: Synthetic Construct

<400> SEQUENCE: 47
tagtataaag                                                         10

<210> SEQ ID NO 48
<211> LENGTH: 30
<212> TYPE: DNA
<213> ORGANISM: Artificial Sequence
<220> FEATURE:
<223> OTHER INFORMATION: Synthetic Construct

<400> SEQUENCE: 48
tcggaaaagg cataaggtaa aataaacatc                                   30

<210> SEQ ID NO 49

<211> LENGTH: 28
<212> TYPE: DNA
<213> ORGANISM: Artificial Sequence
<220> FEATURE:
<223> OTHER INFORMATION: Synthetic Construct

<400> SEQUENCE: 49
cgtcgacggg ctctatttct tcaacaca					28

<210> SEQ ID NO 50
<211> LENGTH: 28
<212> TYPE: DNA
<213> ORGANISM: Artificial Sequence
<220> FEATURE:
<223> OTHER INFORMATION: Synthetic Construct

<400> SEQUENCE: 50
atctatttcc gcttaaaatg agagtatc					28

<210> SEQ ID NO 51
<211> LENGTH: 26
<212> TYPE: DNA
<213> ORGANISM: Artificial Sequence
<220> FEATURE:
<223> OTHER INFORMATION: Synthetic Construct

<400> SEQUENCE: 51
agtgccagcg attttatatt cttttt					26

<210> SEQ ID NO 52
<211> LENGTH: 21
<212> TYPE: DNA
<213> ORGANISM: Artificial Sequence
<220> FEATURE:
<223> OTHER INFORMATION: Synthetic Construct

<400> SEQUENCE: 52
acgccgcaga acagccgagt c						21

<210> SEQ ID NO 53
<211> LENGTH: 30
<212> TYPE: DNA
<213> ORGANISM: Artificial Sequence
<220> FEATURE:
<223> OTHER INFORMATION: Synthetic Construct

<400> SEQUENCE: 53
accaacgagg gattcaaacc gcttacttat				30

<210> SEQ ID NO 54
<211> LENGTH: 27
<212> TYPE: DNA
<213> ORGANISM: Artificial Sequence
<220> FEATURE:
<223> OTHER INFORMATION: Synthetic Construct

<400> SEQUENCE: 54
cataaaacgc agctgagtat tagaaag					27

<210> SEQ ID NO 55
<211> LENGTH: 27
<212> TYPE: DNA
<213> ORGANISM: Artificial Sequence
<220> FEATURE:
<223> OTHER INFORMATION: Synthetic Construct

<400> SEQUENCE: 55

```
agttccgatg tttattttac cttatgc                                       27

<210> SEQ ID NO 56
<211> LENGTH: 22
<212> TYPE: DNA
<213> ORGANISM: Artificial Sequence
<220> FEATURE:
<223> OTHER INFORMATION: Synthetic Construct

<400> SEQUENCE: 56
tgcctgcgac cgtgccaata cc                                            22

<210> SEQ ID NO 57
<211> LENGTH: 30
<212> TYPE: DNA
<213> ORGANISM: Artificial Sequence
<220> FEATURE:
<223> OTHER INFORMATION: Synthetic Construct

<400> SEQUENCE: 57
gtgcggcaat aaaaacgtac tcggtcataa                                    30

<210> SEQ ID NO 58
<211> LENGTH: 25
<212> TYPE: DNA
<213> ORGANISM: Artificial Sequence
<220> FEATURE:
<223> OTHER INFORMATION: Synthetic Construct

<400> SEQUENCE: 58
gtaaaaagcc ggaactgaag gaata                                         25

<210> SEQ ID NO 59
<211> LENGTH: 30
<212> TYPE: DNA
<213> ORGANISM: Artificial Sequence
<220> FEATURE:
<223> OTHER INFORMATION: Synthetic Construct

<400> SEQUENCE: 59
gtatcagtgc gacgagttaa tctggttggt                                    30

<210> SEQ ID NO 60
<211> LENGTH: 28
<212> TYPE: DNA
<213> ORGANISM: Artificial Sequence
<220> FEATURE:
<223> OTHER INFORMATION: Synthetic Construct

<400> SEQUENCE: 60
tccggaacca caaacaatcg aagaaatc                                      28

<210> SEQ ID NO 61
<211> LENGTH: 27
<212> TYPE: DNA
<213> ORGANISM: Artificial Sequence
<220> FEATURE:
<223> OTHER INFORMATION: Synthetic Construct

<400> SEQUENCE: 61
agtgtcgcat cagccttctc caaaatc                                       27

<210> SEQ ID NO 62
<211> LENGTH: 24
<212> TYPE: DNA
```

```
<213> ORGANISM: Artificial Sequence
<220> FEATURE:
<223> OTHER INFORMATION: Synthetic Construct

<400> SEQUENCE: 62
aatctgggcg atagaaacga tagc                                          24

<210> SEQ ID NO 63
<211> LENGTH: 25
<212> TYPE: DNA
<213> ORGANISM: Artificial Sequence
<220> FEATURE:
<223> OTHER INFORMATION: Synthetic Construct

<400> SEQUENCE: 63
tcgcggagag tatgcttccc tgaac                                         25

<210> SEQ ID NO 64
<211> LENGTH: 22
<212> TYPE: DNA
<213> ORGANISM: Artificial Sequence
<220> FEATURE:
<223> OTHER INFORMATION: Synthetic Construct

<400> SEQUENCE: 64
aattcggtac ttttcaggtt gg                                            22

<210> SEQ ID NO 65
<211> LENGTH: 23
<212> TYPE: DNA
<213> ORGANISM: Artificial Sequence
<220> FEATURE:
<223> OTHER INFORMATION: Synthetic Construct

<400> SEQUENCE: 65
aattatgtca gcagcaggtt cgt                                           23

<210> SEQ ID NO 66
<211> LENGTH: 24
<212> TYPE: DNA
<213> ORGANISM: Artificial Sequence
<220> FEATURE:
<223> OTHER INFORMATION: Synthetic Construct

<400> SEQUENCE: 66
actttgcgct attttcaggg tcag                                          24

<210> SEQ ID NO 67
<211> LENGTH: 25
<212> TYPE: DNA
<213> ORGANISM: Artificial Sequence
<220> FEATURE:
<223> OTHER INFORMATION: Synthetic Construct

<400> SEQUENCE: 67
tgtcttcatc ttcaggtgtt tttgg                                         25

<210> SEQ ID NO 68
<211> LENGTH: 22
<212> TYPE: DNA
<213> ORGANISM: Artificial Sequence
<220> FEATURE:
<223> OTHER INFORMATION: Synthetic Construct

<400> SEQUENCE: 68
tcgttcatgg tctggttgga gg                                            22
```

<210> SEQ ID NO 69
<211> LENGTH: 24
<212> TYPE: DNA
<213> ORGANISM: Artificial Sequence
<220> FEATURE:
<223> OTHER INFORMATION: Synthetic Construct

<400> SEQUENCE: 69
ttgtttgtaa atcgtgcgta tcat                                      24

<210> SEQ ID NO 70
<211> LENGTH: 24
<212> TYPE: DNA
<213> ORGANISM: Artificial Sequence
<220> FEATURE:
<223> OTHER INFORMATION: Synthetic Construct

<400> SEQUENCE: 70
cgggtcgttg tgttaatgga tgtc                                      24

<210> SEQ ID NO 71
<211> LENGTH: 24
<212> TYPE: DNA
<213> ORGANISM: Artificial Sequence
<220> FEATURE:
<223> OTHER INFORMATION: Synthetic Construct

<400> SEQUENCE: 71
attatttata tttgcgggtt tcac                                      24

<210> SEQ ID NO 72
<211> LENGTH: 20
<212> TYPE: DNA
<213> ORGANISM: Artificial Sequence
<220> FEATURE:
<223> OTHER INFORMATION: Synthetic Construct

<400> SEQUENCE: 72
attgtagagc gtgcgtattc                                           20

<210> SEQ ID NO 73
<211> LENGTH: 20
<212> TYPE: DNA
<213> ORGANISM: Artificial Sequence
<220> FEATURE:
<223> OTHER INFORMATION: Synthetic Construct

<400> SEQUENCE: 73
attggccatg agttgatact                                           20

<210> SEQ ID NO 74
<211> LENGTH: 30
<212> TYPE: DNA
<213> ORGANISM: Artificial Sequence
<220> FEATURE:
<223> OTHER INFORMATION: Synthetic Construct

<400> SEQUENCE: 74
tgctacccct attggatgac tcacgaaaga                                30

<210> SEQ ID NO 75
<211> LENGTH: 26
<212> TYPE: DNA
<213> ORGANISM: Artificial Sequence
<220> FEATURE:

```
<223> OTHER INFORMATION: Synthetic Construct

<400> SEQUENCE: 75
tgtaatcaaa gcagggcgca tcagga                                            26

<210> SEQ ID NO 76
<211> LENGTH: 22
<212> TYPE: DNA
<213> ORGANISM: Artificial Sequence
<220> FEATURE:
<223> OTHER INFORMATION: Synthetic Construct

<400> SEQUENCE: 76
gggtggcgtt ccttcagatg tg                                                22

<210> SEQ ID NO 77
<211> LENGTH: 25
<212> TYPE: DNA
<213> ORGANISM: Artificial Sequence
<220> FEATURE:
<223> OTHER INFORMATION: Synthetic Construct

<400> SEQUENCE: 77
aaatgggctt accgtgttcg tgctc                                             25

<210> SEQ ID NO 78
<211> LENGTH: 24
<212> TYPE: DNA
<213> ORGANISM: Artificial Sequence
<220> FEATURE:
<223> OTHER INFORMATION: Synthetic Construct

<400> SEQUENCE: 78
gttcgactcg ttaattcagc acac                                              24

<210> SEQ ID NO 79
<211> LENGTH: 23
<212> TYPE: DNA
<213> ORGANISM: Artificial Sequence
<220> FEATURE:
<223> OTHER INFORMATION: Synthetic Construct

<400> SEQUENCE: 79
tttttaggcg tcattttcat tgg                                               23

<210> SEQ ID NO 80
<211> LENGTH: 22
<212> TYPE: DNA
<213> ORGANISM: Artificial Sequence
<220> FEATURE:
<223> OTHER INFORMATION: Synthetic Construct

<400> SEQUENCE: 80
tgcgccatgg gtttcaagta tc                                                22

<210> SEQ ID NO 81
<211> LENGTH: 19
<212> TYPE: DNA
<213> ORGANISM: Artificial Sequence
<220> FEATURE:
<223> OTHER INFORMATION: Synthetic Construct

<400> SEQUENCE: 81
ttcgggaggt cgccacaag                                                    19
```

```
<210> SEQ ID NO 82
<211> LENGTH: 26
<212> TYPE: DNA
<213> ORGANISM: Artificial Sequence
<220> FEATURE:
<223> OTHER INFORMATION: Synthetic Construct

<400> SEQUENCE: 82
ttttgggtgg gagtgttatg aatgtc                                           26

<210> SEQ ID NO 83
<211> LENGTH: 29
<212> TYPE: DNA
<213> ORGANISM: Artificial Sequence
<220> FEATURE:
<223> OTHER INFORMATION: Synthetic Construct

<400> SEQUENCE: 83
atactgcaac ccgctaataa taataactc                                        29

<210> SEQ ID NO 84
<211> LENGTH: 26
<212> TYPE: DNA
<213> ORGANISM: Artificial Sequence
<220> FEATURE:
<223> OTHER INFORMATION: Synthetic Construct

<400> SEQUENCE: 84
tggggcgcgg atatcaatag taagga                                           26

<210> SEQ ID NO 85
<211> LENGTH: 26
<212> TYPE: DNA
<213> ORGANISM: Artificial Sequence
<220> FEATURE:
<223> OTHER INFORMATION: Synthetic Construct

<400> SEQUENCE: 85
tttgcgcatg cgtaatttgg tatcgt                                           26

<210> SEQ ID NO 86
<211> LENGTH: 22
<212> TYPE: DNA
<213> ORGANISM: Artificial Sequence
<220> FEATURE:
<223> OTHER INFORMATION: Synthetic Construct

<400> SEQUENCE: 86
attttatacg ccgaactctt tg                                               22

<210> SEQ ID NO 87
<211> LENGTH: 21
<212> TYPE: DNA
<213> ORGANISM: Artificial Sequence
<220> FEATURE:
<223> OTHER INFORMATION: Synthetic Construct

<400> SEQUENCE: 87
gatccgcgat catttacctt t                                                21

<210> SEQ ID NO 88
<211> LENGTH: 30
<212> TYPE: DNA
<213> ORGANISM: Artificial Sequence
<220> FEATURE:
<223> OTHER INFORMATION: Synthetic Construct
```

```
<400> SEQUENCE: 88
gagccatatt cgtgtgagag cattagtgtc                              30

<210> SEQ ID NO 89
<211> LENGTH: 30
<212> TYPE: DNA
<213> ORGANISM: Artificial Sequence
<220> FEATURE:
<223> OTHER INFORMATION: Synthetic Construct

<400> SEQUENCE: 89
tctggatgat atgattctgt ttgcggtttc                              30

<210> SEQ ID NO 90
<211> LENGTH: 21
<212> TYPE: DNA
<213> ORGANISM: Artificial Sequence
<220> FEATURE:
<223> OTHER INFORMATION: Synthetic Construct

<400> SEQUENCE: 90
caagcatagc cttgcggaca t                                       21

<210> SEQ ID NO 91
<211> LENGTH: 23
<212> TYPE: DNA
<213> ORGANISM: Artificial Sequence
<220> FEATURE:
<223> OTHER INFORMATION: Synthetic Construct

<400> SEQUENCE: 91
acgaaatttt ctgcctgacg act                                     23

<210> SEQ ID NO 92
<211> LENGTH: 23
<212> TYPE: DNA
<213> ORGANISM: Artificial Sequence
<220> FEATURE:
<223> OTHER INFORMATION: Synthetic Construct

<400> SEQUENCE: 92
ttcttagcag atgatgtcat cgc                                     23

<210> SEQ ID NO 93
<211> LENGTH: 20
<212> TYPE: DNA
<213> ORGANISM: Artificial Sequence
<220> FEATURE:
<223> OTHER INFORMATION: Synthetic Construct

<400> SEQUENCE: 93
cgtggattga caacgcgttt                                         20

<210> SEQ ID NO 94
<211> LENGTH: 20
<212> TYPE: DNA
<213> ORGANISM: Artificial Sequence
<220> FEATURE:
<223> OTHER INFORMATION: Synthetic Construct

<400> SEQUENCE: 94
agcttatgtc gacaagcgct                                         20

<210> SEQ ID NO 95
<211> LENGTH: 26
```

```
<212> TYPE: DNA
<213> ORGANISM: Artificial Sequence
<220> FEATURE:
<223> OTHER INFORMATION: Synthetic Construct

<400> SEQUENCE: 95
tgattaattt gtgatacttc catgtt                                          26

<210> SEQ ID NO 96
<211> LENGTH: 19
<212> TYPE: DNA
<213> ORGANISM: Artificial Sequence
<220> FEATURE:
<223> OTHER INFORMATION: Synthetic Construct

<400> SEQUENCE: 96
ccaattcgga agggtctcg                                                  19

<210> SEQ ID NO 97
<211> LENGTH: 25
<212> TYPE: DNA
<213> ORGANISM: Artificial Sequence
<220> FEATURE:
<223> OTHER INFORMATION: Synthetic Construct

<400> SEQUENCE: 97
ggggtagcac ttttgtttgt tatct                                           25

<210> SEQ ID NO 98
<211> LENGTH: 20
<212> TYPE: DNA
<213> ORGANISM: Artificial Sequence
<220> FEATURE:
<223> OTHER INFORMATION: Synthetic Construct

<400> SEQUENCE: 98
atcgtctacc cgacgttcac                                                 20

<210> SEQ ID NO 99
<211> LENGTH: 20
<212> TYPE: DNA
<213> ORGANISM: Artificial Sequence
<220> FEATURE:
<223> OTHER INFORMATION: Synthetic Construct

<400> SEQUENCE: 99
gtgggctatg aactggtcgt                                                 20

<210> SEQ ID NO 100
<211> LENGTH: 20
<212> TYPE: DNA
<213> ORGANISM: Artificial Sequence
<220> FEATURE:
<223> OTHER INFORMATION: Synthetic Construct

<400> SEQUENCE: 100
tatactgctc cgggacttgc                                                 20

<210> SEQ ID NO 101
<211> LENGTH: 20
<212> TYPE: DNA
<213> ORGANISM: Artificial Sequence
<220> FEATURE:
<223> OTHER INFORMATION: Synthetic Construct

<400> SEQUENCE: 101
```

```
cagccccgta cagattgttt                                          20

<210> SEQ ID NO 102
<211> LENGTH: 20
<212> TYPE: DNA
<213> ORGANISM: Artificial Sequence
<220> FEATURE:
<223> OTHER INFORMATION: Synthetic Construct

<400> SEQUENCE: 102
tcttccaaca cacgattcca                                          20

<210> SEQ ID NO 103
<211> LENGTH: 20
<212> TYPE: DNA
<213> ORGANISM: Artificial Sequence
<220> FEATURE:
<223> OTHER INFORMATION: Synthetic Construct

<400> SEQUENCE: 103
aagaacgcgt accaccaaat                                          20

<210> SEQ ID NO 104
<211> LENGTH: 20
<212> TYPE: DNA
<213> ORGANISM: Artificial Sequence
<220> FEATURE:
<223> OTHER INFORMATION: Synthetic Construct

<400> SEQUENCE: 104
acccttcacc aggacaactg                                          20

<210> SEQ ID NO 105
<211> LENGTH: 20
<212> TYPE: DNA
<213> ORGANISM: Artificial Sequence
<220> FEATURE:
<223> OTHER INFORMATION: Synthetic Construct

<400> SEQUENCE: 105
aaatagtacg cgccaccttg                                          20

<210> SEQ ID NO 106
<211> LENGTH: 20
<212> TYPE: DNA
<213> ORGANISM: Artificial Sequence
<220> FEATURE:
<223> OTHER INFORMATION: Synthetic Construct

<400> SEQUENCE: 106
catcttgatc agcgtgcaat                                          20

<210> SEQ ID NO 107
<211> LENGTH: 20
<212> TYPE: DNA
<213> ORGANISM: Artificial Sequence
<220> FEATURE:
<223> OTHER INFORMATION: Synthetic Construct

<400> SEQUENCE: 107
acgtcagtat tccccagcac                                          20

<210> SEQ ID NO 108
<211> LENGTH: 20
<212> TYPE: DNA
<213> ORGANISM: Artificial Sequence
```

```
<220> FEATURE:
<223> OTHER INFORMATION: Synthetic Construct

<400> SEQUENCE: 108
tcggtaattg attggggaga                                              20

<210> SEQ ID NO 109
<211> LENGTH: 20
<212> TYPE: DNA
<213> ORGANISM: Artificial Sequence
<220> FEATURE:
<223> OTHER INFORMATION: Synthetic Construct

<400> SEQUENCE: 109
tgcagcacca aacaaacaat                                              20

<210> SEQ ID NO 110
<211> LENGTH: 20
<212> TYPE: DNA
<213> ORGANISM: Artificial Sequence
<220> FEATURE:
<223> OTHER INFORMATION: Synthetic Construct

<400> SEQUENCE: 110
attgaaggcc gagcgtgaac                                              20

<210> SEQ ID NO 111
<211> LENGTH: 20
<212> TYPE: DNA
<213> ORGANISM: Artificial Sequence
<220> FEATURE:
<223> OTHER INFORMATION: Synthetic Construct

<400> SEQUENCE: 111
ccgagggtga aagcaaggag                                              20

<210> SEQ ID NO 112
<211> LENGTH: 20
<212> TYPE: DNA
<213> ORGANISM: Artificial Sequence
<220> FEATURE:
<223> OTHER INFORMATION: Synthetic Construct

<400> SEQUENCE: 112
catgtgcttt ccaatcatgc                                              20

<210> SEQ ID NO 113
<211> LENGTH: 22
<212> TYPE: DNA
<213> ORGANISM: Artificial Sequence
<220> FEATURE:
<223> OTHER INFORMATION: Synthetic Construct

<400> SEQUENCE: 113
ttgacatttt tgcttttgaa gg                                           22

<210> SEQ ID NO 114
<211> LENGTH: 20
<212> TYPE: DNA
<213> ORGANISM: Artificial Sequence
<220> FEATURE:
<223> OTHER INFORMATION: Synthetic Construct

<400> SEQUENCE: 114
tgtgacccag cagataacga                                              20
```

<210> SEQ ID NO 115
<211> LENGTH: 20
<212> TYPE: DNA
<213> ORGANISM: Artificial Sequence
<220> FEATURE:
<223> OTHER INFORMATION: Synthetic Construct

<400> SEQUENCE: 115
taattgcctt cttgggttgg                                               20

<210> SEQ ID NO 116
<211> LENGTH: 20
<212> TYPE: DNA
<213> ORGANISM: Artificial Sequence
<220> FEATURE:
<223> OTHER INFORMATION: Synthetic Construct

<400> SEQUENCE: 116
taagagccgt gaatggtgtg                                               20

<210> SEQ ID NO 117
<211> LENGTH: 20
<212> TYPE: DNA
<213> ORGANISM: Artificial Sequence
<220> FEATURE:
<223> OTHER INFORMATION: Synthetic Construct

<400> SEQUENCE: 117
atttacgccg gtgcattact                                               20

<210> SEQ ID NO 118
<211> LENGTH: 21
<212> TYPE: DNA
<213> ORGANISM: Artificial Sequence
<220> FEATURE:
<223> OTHER INFORMATION: Synthetic Construct

<400> SEQUENCE: 118
tcatataatt tccgaccgac a                                             21

<210> SEQ ID NO 119
<211> LENGTH: 20
<212> TYPE: DNA
<213> ORGANISM: Artificial Sequence
<220> FEATURE:
<223> OTHER INFORMATION: Synthetic Construct

<400> SEQUENCE: 119
tcggcttgca tttagacgtt                                               20

<210> SEQ ID NO 120
<211> LENGTH: 24
<212> TYPE: DNA
<213> ORGANISM: Artificial Sequence
<220> FEATURE:
<223> OTHER INFORMATION: Synthetic Construct

<400> SEQUENCE: 120
tcaaaagcaa tcatgagtat gaca                                          24

<210> SEQ ID NO 121
<211> LENGTH: 20
<212> TYPE: DNA

```
<213> ORGANISM: Artificial Sequence
<220> FEATURE:
<223> OTHER INFORMATION: Synthetic Construct

<400> SEQUENCE: 121
tcagtaacgc gatgttcagg                                              20

<210> SEQ ID NO 122
<211> LENGTH: 20
<212> TYPE: DNA
<213> ORGANISM: Artificial Sequence
<220> FEATURE:
<223> OTHER INFORMATION: Synthetic Construct

<400> SEQUENCE: 122
aaagcggcgt ttgatagaaa                                              20

<210> SEQ ID NO 123
<211> LENGTH: 20
<212> TYPE: DNA
<213> ORGANISM: Artificial Sequence
<220> FEATURE:
<223> OTHER INFORMATION: Synthetic Construct

<400> SEQUENCE: 123
tgcgatgcat tctcctgtta                                              20

<210> SEQ ID NO 124
<211> LENGTH: 20
<212> TYPE: DNA
<213> ORGANISM: Artificial Sequence
<220> FEATURE:
<223> OTHER INFORMATION: Synthetic Construct

<400> SEQUENCE: 124
tgttacgaat ggcgactgaa                                              20

<210> SEQ ID NO 125
<211> LENGTH: 19
<212> TYPE: DNA
<213> ORGANISM: Artificial Sequence
<220> FEATURE:
<223> OTHER INFORMATION: Synthetic Construct

<400> SEQUENCE: 125
ccatcagttg aaatgaaac                                               19

<210> SEQ ID NO 126
<211> LENGTH: 20
<212> TYPE: DNA
<213> ORGANISM: Artificial Sequence
<220> FEATURE:
<223> OTHER INFORMATION: Synthetic Construct

<400> SEQUENCE: 126
tacttgataa acttacggat                                              20
```